(12) United States Patent
Shiflett et al.

(10) Patent No.: US 8,628,644 B2
(45) Date of Patent: Jan. 14, 2014

(54) UTILIZING IONIC LIQUIDS FOR HYDROFLUOROCARBON SEPARATION

(75) Inventors: Mark B. Shiflett, New Castle, DE (US);
Akimichi Yokozeki, New Castle (JP)

(73) Assignee: E I du Pont Nemours and Company, Wilmington, DE (US)

( * ) Notice: Subject to any disclaimer, the term of this patent is extended or adjusted under 35 U.S.C. 154(b) by 898 days.

(21) Appl. No.: 11/525,466

(22) Filed: Sep. 22, 2006

(65) Prior Publication Data

US 2007/0131535 A1    Jun. 14, 2007

Related U.S. Application Data

(60) Provisional application No. 60/719,735, filed on Sep. 22, 2005.

(51) Int. Cl.
| | | |
|---|---|---|
| *B01D 3/40* | (2006.01) | |
| *B01D 3/34* | (2006.01) | |
| *B01D 3/36* | (2006.01) | |
| *C07C 17/386* | (2006.01) | |
| *C07C 19/08* | (2006.01) | |
| *C07B 63/00* | (2006.01) | |

(52) U.S. Cl.
USPC ............... 203/50; 62/238.5; 203/52; 203/57; 203/67; 203/51; 210/656; 423/293; 423/489; 570/177; 570/178; 570/180; 570/262; 570/263

(58) Field of Classification Search
USPC .......... 62/238.5; 203/51, 52, 57, 67; 570/177, 570/178, 180, 262, 263; 210/656; 252/67; 423/293, 464, 489
See application file for complete search history.

(56) References Cited

U.S. PATENT DOCUMENTS

| | | | | |
|---|---|---|---|---|
| 4,388,812 | A | | 6/1983 | Clark |
| 5,698,750 | A | * | 12/1997 | Mouk et al. ............... 570/177 |
| 5,709,092 | A | | 1/1998 | Shiflett |
| 6,155,057 | A | | 12/2000 | Angell |
| 6,339,182 | B1 | | 1/2002 | Munson |
| 6,579,343 | B2 | | 6/2003 | Brennecke |
| 6,843,934 | B2 | * | 1/2005 | Bement et al. ........... 252/182.24 |
| 7,208,605 | B2 | | 4/2007 | Davis |
| 7,410,586 | B2 | | 8/2008 | Beste |
| 7,435,318 | B2 | * | 10/2008 | Arlt et al. ........................ 203/14 |
| 7,709,635 | B2 | | 5/2010 | Davis |
| 7,744,838 | B2 | | 6/2010 | Davis |
| 7,765,823 | B2 | * | 8/2010 | Shiflett et al. ................ 62/238.6 |
| 7,964,760 | B2 | * | 6/2011 | Shiflett et al. ................ 570/180 |

(Continued)

FOREIGN PATENT DOCUMENTS

| | | |
|---|---|---|
| DE | 101 36 614 A1 | 2/2003 |
| EP | 1 029 840 A1 | 8/2000 |

(Continued)

OTHER PUBLICATIONS

Seiler et. al., Separation of Azeotropic Mixtures Using Hyperbranched Polymers or Ionic Liquids, Amer. Inst. Chem. Engrs J., 2004, vol. 50:2439-2453.

(Continued)

*Primary Examiner* — Virginia Manoharan

(57) ABSTRACT

The present invention relates to a process for separating close-boiling and azeotropic components of mixtures, wherein said mixtures contain at least one hydrofluorocarbon compound, using at least one ionic liquid.

15 Claims, 18 Drawing Sheets

(56) References Cited

U.S. PATENT DOCUMENTS

| | | |
|---|---|---|
| 2004/0035293 A1 | 2/2004 | Davis |
| 2004/0133058 A1 | 7/2004 | Arlt et al. |
| 2005/0196671 A1 | 9/2005 | Paonessa |
| 2005/0196676 A1 | 9/2005 | Singh |
| 2006/0197053 A1 | 9/2006 | Shiflett et al. |
| 2006/0251961 A1 | 11/2006 | Olbert et al. |
| 2007/0019708 A1 | 1/2007 | Shiflett et al. |
| 2007/0080052 A1 | 4/2007 | Beste et al. |
| 2007/0089449 A1 | 4/2007 | Gurin |
| 2007/0131535 A1 | 6/2007 | Shiflett et al. |
| 2007/0142646 A1 | 6/2007 | Maase |
| 2007/0144186 A1 | 6/2007 | Shiflett et al. |
| 2007/0295478 A1 | 12/2007 | Shiflett et al. |
| 2007/0297965 A1* | 12/2007 | Shiflett et al. ............ 423/293 |
| 2008/0028777 A1 | 2/2008 | Boesmann et al. |
| 2008/0153697 A1 | 6/2008 | Shiflett et al. |
| 2008/0293978 A1 | 11/2008 | Shiflett |
| 2009/0131728 A1 | 5/2009 | Shiflett |
| 2009/0326145 A1* | 12/2009 | Gerster et al. ............ 524/576 |
| 2010/0095703 A1 | 4/2010 | Jork |
| 2010/0145073 A1 | 6/2010 | Foo |
| 2010/0145074 A1 | 6/2010 | Foo |
| 2010/0152465 A1 | 6/2010 | Davis |

FOREIGN PATENT DOCUMENTS

| | | |
|---|---|---|
| WO | 9850331 A | 11/1998 |
| WO | WO 99/07660 A1 | 2/1999 |
| WO | 2005016483 A | 2/2005 |
| WO | WO 2005/016483 A1 | 2/2005 |
| WO | WO 2005/113702 A1 | 12/2005 |
| WO | 2007038363 A | 4/2007 |

OTHER PUBLICATIONS

Robin D. Rogers et. al., Ionic Liquids Solvents of the Future?, Science, 2003, vol. 302:792-793.

Kenneth R. Seddon, Ionic Liquids for Clean Technology, J. Chem. Tech. Biotechnol., 1997, vol. 68:351-356.

Helene Olivier et. al., Nonaqueous Room-Temperature Ionic Liquids: A New Class of Solvents for Catalytic Organic Reactions, Chem. Ind., 1996, vol. 68:249-263.

John E. Enderby, Ionic Liquids: Recent Progress and Remaining Promblems, J. Phys. Condensed Matter, 1993, vol. 5:B99-B106.

Michael Freemantle, Designer Solvents: Ionic Liquids May Boost Clean Technology Development, Chemical and Engineering News, 1998, pp. 32-37.

Charles M. Gordon et. al., Ionic Liquid Crystals: Hexafluorophosphate Salts, J. Mater. Chem., 1998, vol. 8:2627-2636.

Thomas Welton, Room-Temperature Ionic Liquids. Solvents for Synthesis and Catalysts, Chem. Rev., 1999, vol. 99:2071-2084.

F.E. Pinkerton et. al., High-Pressure Gravimetric Measurement of Hydrogen Capacity in Vapor-Grown Carbon Nanofibers and Related Materials, Proceedings of the 11th Canadian Hydrogen Conference, 2001, pp. 633-642.

Shiflett et. al., Solubilities and Diffusivities of Carbon Dioxide in Ionic Liquids: [bmim][PF6]and [bmim][BF4], Ind. Eng. Chem. Research, 2005, vol. 44:4453-4464.

Yokozeki, Time-Dependent Behavior of Gas Absorption in Lubricant Oil, Int. J. Refrigeration, 2002, vol. 22:695-704.

S. I. Sandler, The Estimation of the Gibbs Free Energy and Fugacity of a Component in a Mixture, Chemical and Engineering Thermodynamics, Chapter 7, $3^{rd}$ Edition, 1999, pp. 388-477, John Wiley and Sons, Inc.

Camper et. al., Gas Solubilities in Room-Temperature Ionic Liquids, Eng. Chem. Res., 2004, vol. 43:3049-5054.

J. L. Anthony et. al., Solubilities and Thermodynamic Properties of Gases in the Ionic Liquid 1-n-Butyl-3-methylimidazolium Hexafluorophosphate, J. Phys. Chem. B, 2002, vol. 106:7315-7320.

P. Husson-Borg et. al., Solubilities of Oxygen and Carbon Dioxide in Butyl Methyl Imidazolium Tetrafluoroborate as a Function of Temperature and at Pressure Close to Atmosphere, J. Chem. Eng. Eng. Data, 2003, vol. 48:480-485.

Huddleston et. al., Room Temperature Ionic Liquids as Novel Media for Clean Liquid Extraction, Chemical Communications—Chemcom, Royal Society of Chemistry, 1998, pp. 1765-1766, XP002926442.

International Search Report Dated Mar. 16, 2007, International Application No. PCT/US2006/037137, International Filing Date Sep. 22, 2006.

Nezu et al., Thermogynamic Properties of Working Fluid Pairs With R-134A for Absorption Refrigeration System, Natura Lworking Fluids, IIR Gustaf Lorentzen Conf. $5^{th}$, China, 2002, pp. 446-453.

Fatouh et al., Comparison of R22-Abosrbent Pairs for Absorption Cooling Based on P-T-X Data, Renewable Energy, 1993, Vol. 3, pp. 31-37.

Bhatt et al., Thermodynamic Modelling OG Absorption-Resorption Heating Cycles With Some New Working Pairs, Heat Recovery System & CHP, 1992, Vol. 12, pp. 225-233.

Yokozeki, Theoretical Performances of Various Refrigerant-Absorbent Pairs in a Vapor-Abosrption Orefrigeration Cycle by the Use of Equations of STTE, Applied Energy, 2005, Vol. 80, pp. 383-399.

Gryzll et al., The Development of a Performance-Enhancing Additive for Vapor-Compression Heat Pumps, Proceedings of the $32^{nd}$ Intersociety Energy Conversion Engineering Conference, 1997, Vol. 3 & 4, pp. 1252-1257.

Fukata et al., Performance of Compression/Absorption Hybeid Refrigeration Cycle With Propane/Mineral Combination, International Journal of Refrigeraton, 2002, vol. 25, pp. 907-915.

Shiflett et al., Solubilities and Diffusivities of Carbon Dioxide in Ionic Liquids [bmim] [PF6] and [BF4], Ind. Eng. Chem. Res., 2005 vol. 44, pp. 4453-4464.

Shiflett et al., Solubility and Diffusivity of Hydrofluorocarbons in Room Temperature Ionic Liquids, Aichie J 2006 wol. 52, p. 1205.

Shiflett, Soluibility Differences of Halocarbo Isomers in Ionic Liquid, J. Chem. Eng. Data, 2007, vol. 52, pp. 2007-2015.

* cited by examiner

Figure 1 – A schematic diagram of a simple extractive distillation system

Figure 2 – A schematic diagram of a simple ASPEN extractive distillation process Solubility of difluoromethane (HFC-32) in 1-butyl-3-methylimidazolium hexafluorophosphate ([bmim][PF$_6$])

Solubility of pentafluoroethane (HFC-125) in 1-butyl-3-methylimidazolium hexafluorophosphate ([bmim][PF$_6$])

Solubility of 1,1,1,2-tetrafluoroethane (HFC-134a) in 1-butyl-3-methylimidazolium hexafluorophosphate ([bmim][PF$_6$])

Solubility of 1,1,1-trifluoroethane (HFC-143a) in 1-butyl-3-methylimidazolium hexafluorophosphate ([bmim][PF$_6$])

Solubility of 1,1-difluoroethane (HFC-152a) in 1-butyl-3-methylimidazolium hexafluorophosphate ([bmim][PF$_6$])

Solubility of difluoromethane (HFC-32) in 1-butyl-3-methylimidazolium tetrafluoroborate ([bmim][BF$_4$])

Solubility of trifluoromethane (HFC-23) in 1-butyl-3-methylimidazolium hexafluorophosphate ([bmim][PF$_6$]).

Solubility of trifluoromethane (HFC-23) in 1-ethyl-3-methylimidazolium tetrafluoroborate ([emim][PF$_6$])

Solubility of difluoromethane (HFC-32) in 1, 2-dimethyl-3-propylimidazolium tris(trifluoromethylsulfonyl) methide ([dmpim][TMeM])

Solubility of difluoromethane (HFC-32) in 1-ethyl-3-methylimidazolium bis(pentafluoroethylsulfonyl)imide ([emim][BEI])

Solubility of difluoromethane (HFC-32) in 1-ethyl-3-methylimidazolium bis(trifluoroethylsulfonyl)imide ([emim][BMeI])

Solubility of difluoromethane (HFC-32) in 1-methyl-3-propylpyridinium bis(trifluoroethylsulfonyl)imide ([pmpy][BMeI])

Solubility of difluoromethane (HFC-32) in 1-butyl-3-methylpyridinium bis(trifluoroethylsulfonyl)imide ([bmpy][BMeI])

Isotherm Comparison of Difluoromethane (HFC-32) and Imidazolium based Ionic
Liquids at 25 °C P/P₀ versus mole fraction Figure 18- A schematic diagram of the gravimetric microbalance
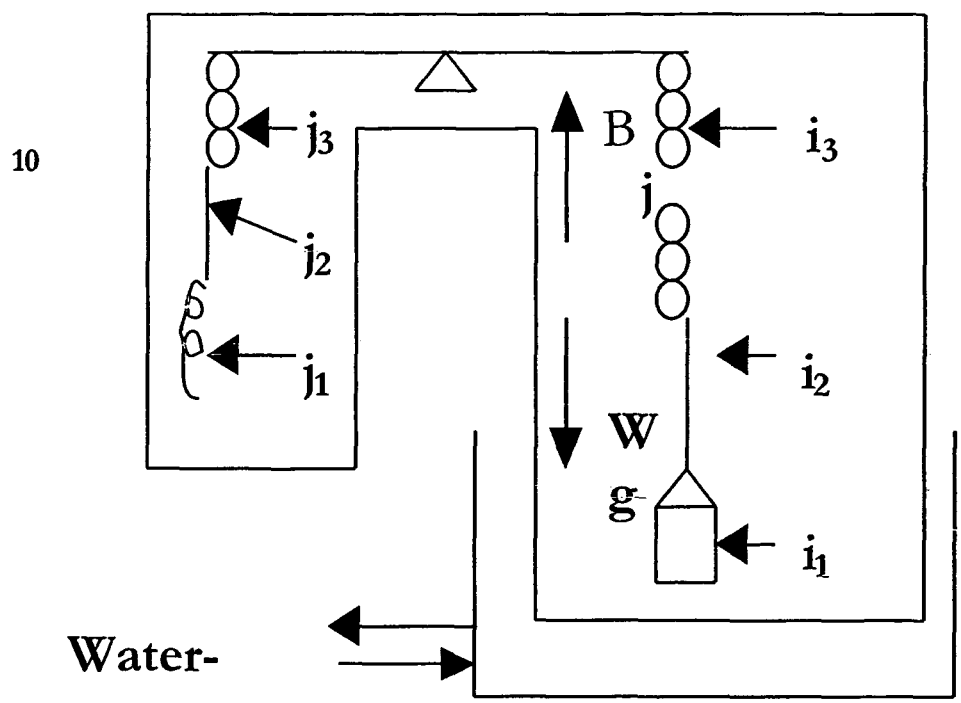

UTILIZING IONIC LIQUIDS FOR HYDROFLUOROCARBON SEPARATION

This application claims the benefit of U.S. Provisional Application No. 60/719,735, filed Sep. 22, 2005, which is incorporated in its entirety as a part hereof for all purposes.

TECHNICAL FIELD

The present invention relates to a process for separating components of a mixture that contains one or more hydrofluorocarbon compounds by the use of an ionic liquid. The process is useful for the separation of components from an azeotropic or close-boiling mixture by a process that may include, for example, extractive distillation wherein an ionic liquid is used as an entrainer.

BACKGROUND

Processes for the separation of components in a mixture are numerous, and one such process that is commonly used is distillation, which effects the separation of components based on differences in their respective volatilities. Azeotropic mixtures, in which the components have the same vapor phase and liquid phase composition, and close-boiling mixtures cannot, however, be easily separated by conventional distillation. To remedy this situation, a process that is often used for separating a mixture of components that have similar boiling points is extractive distillation, in which an entrainer is added to the mixture to selectively interact with one or more of the other components of the mixture so that separation of the other component(s) is made possible. Seiler et al [*Amer. Inst. Chem. Engrs J.* (2004) 50:2439-2453] describe the use of an ionic liquid as an entrainer in extractive distillation for the separation of the azeotropic systems ethanol-water and THF-water. U.S. Patent Application 2004/0133058 also describes a process for separating close-boiling, and homo- and hetero-azeotropic mixtures by the use of ionic liquids.

A need still remains, however, for improved processes to be used for the separation of components in azeotropic or close-boiling mixtures that contain at least one hydrofluorocarbon compound.

SUMMARY

This invention involves the separation of a component from a mixture where the mixture contains a hydrofluorocarbon compound. In one embodiment, this invention thus provides a process for separating one or more components from a multi-component mixture, wherein the mixture comprises an azeotropic or close-boiling mixture, and wherein the mixture comprises a hydrofluorocarbon compound and one or more members of the group consisting of:
 a) another hydrofluorocarbon compound;
 b) a fluorocarbon compound;
 c) a non-fluorinated hydrocarbon selected from the group consisting of $C_1$ to $C_4$ straight-chain, branched or cyclic alkanes and $C_1$ to $C_4$ straight-chain, branched or cyclic alkenes;
 d) an inert gas selected from the group consisting of $N_2$, $O_2$, $CO_2$, CO, $NH_3$, Ar and $H_2$; and
 e) water; and
wherein the process comprises contacting the mixture with one or more ionic liquids in which one component of the mixture is soluble to a smaller extent than at least one other component of the mixture, and separating the lower-solubility component from the mixture.

When the process is performed by using a technique such as extractive distillation, the process may also involve steps such as adjusting the temperature and/or pressure of the mixture.

BRIEF DESCRIPTION OF THE DRAWINGS

FIG. 18 is a schematic diagram of the gravimetric microbalance used for measuring gas absorption in the ionic liquids. In the diagram j$_1$, j$_2$, and j$_3$ refer to the counterweight, hook and chain, respectively; i$_1$, i$_2$ and i$_3$ refer to the sample container, wire and chain, respectively, W$_g$ refers to the force due to gravity; and B refers to the force due to buoyancy.

DETAILED DESCRIPTION

Figure 1:
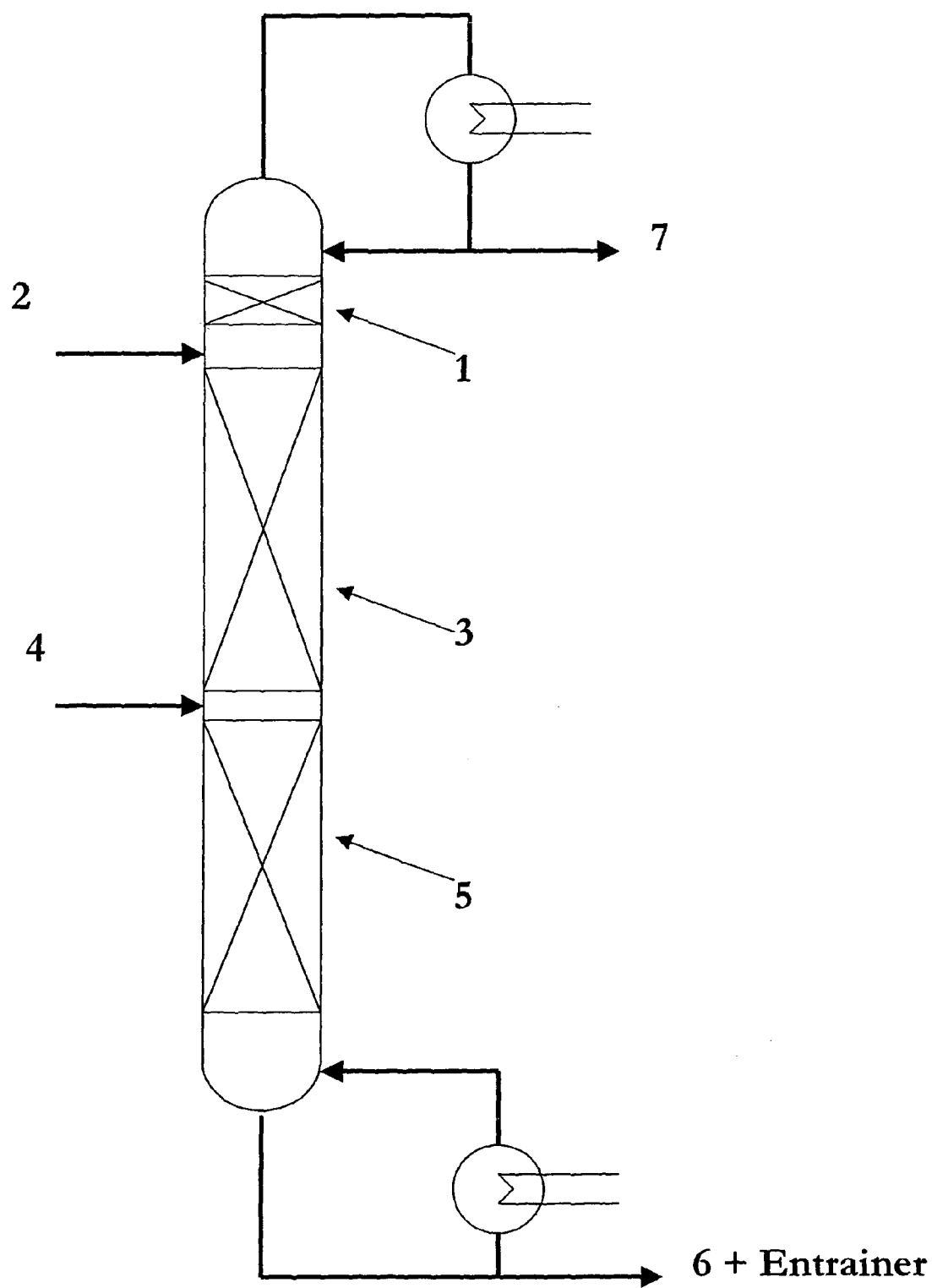
FIG. 1 is a schematic diagram of a simple extractive distillation system.

The present invention relates to the discovery that components of a mixture that contains close-boiling or azeotropic components, wherein at least one component of the mixture is a hydrofluorocarbon compound, can be more effectively separated when an ionic liquid is added to the mixture. Separation can then occur by employing conventional methods of separation such as by performing extractive distillation wherein the ionic liquid functions as an entrainer. The invention thus provides improved separation by a process that involves separating at least one close-boiling or azeotropic component from a mixture, where the mixture comprises a hydrofluorocarbon compound together with at least one member selected from the group consisting of:

a) at least one other hydrofluorocarbon compound;
b) at least one fluorocarbon compound;
c) at least one non-fluorinated hydrocarbon selected from the group consisting of C$_1$ to C$_4$ straight-chain, branched or cyclic alkanes and C$_1$ to C$_4$ straight-chain, branched or cyclic alkenes;
d) at least one inert gas selected from the group consisting of N$_2$, O$_2$, CO$_2$, CO, NH$_3$, Ar and H$_2$; and
e) water;

comprising contacting the mixture with at least one ionic liquid in which one component of the mixture is soluble to a smaller extent than at least one other component of the mixture, and separating the lower-solubility component from the mixture.

The following definitional structure is provided for certain terminology as employed in this specification:

An "alkane" or "alkane compound" is a saturated hydrocarbon compound having the general formula C$_n$H$_{2n+2}$, and may be a straight-chain, branched or cyclic compound.

An "alkene" or "alkene compound" is an unsaturated hydrocarbon compound that contains one or more carbon-carbon double bonds, and may be a straight-chain, branched or cyclic compound. An alkene requires a minimum of two carbons. A cyclic compound requires a minimum of three carbons.

An "aromatic" or "aromatic compound" includes benzene and compounds that resemble benzene in chemical behavior.

An "azeotrope", or an "azeotropic" or "constant boiling" mixture of two or more components, is a mixture in which the composition of the vapor phase and liquid phases are the same, or substantially the same, at a selected temperature or pressure. Included in the definition of a constant boiling mixture is a "near-azeotropic" mixture, which is a mixture that maintains a substantially constant vapor pressure even after evaporative losses, thereby exhibiting constant boiling behavior, such as more particularly described in U.S. Pat. No. 5,709,092. Azeotropic and constant boiling mixtures also include mixtures wherein the boiling points of two or more of the components thereof are separated by only about 5° C. or less.

A "close-boiling" mixture is a mixture in which the boiling points of the components are similar, such as a mixture in which the boiling points of two or more of the components thereof are separated by only about 10° C. or less.

The "critical pressure" of a substance is the pressure required to liquefy a gas at its critical temperature, which is the temperature at and above which vapor of the substance cannot be liquefied, regardless of how much pressure is applied.

An "entrainer" is a compound useful for the separation of components in an azeotropic or constant- or close-boiling mixture, in a process such as extractive distillation, where the entrainer interacts selectively with (but does not chemically react with) one or more of the individual components of the mixture.

"Extractive distillation" is a separation process in which an entrainer is added to an azeotropic or constant- or close-boiling mixture to aid in the separation of the components thereof by volatilization. The entrainer interacts selectively with (but does not chemically react with) one or more components within the mixture.

A "fluorinated ionic liquid" is an ionic liquid having at least one fluorine on either the cation or the anion, or both. A "fluorinated cation" or "fluorinated anion" is a cation or anion, respectively, comprising at least one fluorine atom.

A "fluorocarbon compound" is a compound comprising fluorine and carbon, but not hydrogen. A fluorocarbon compound includes an FC-fluorocarbon compound ("FC"), which consists solely of fluorine and carbon, as well as a chlorofluorocarbon (CFC) compound, wherein FC and CFC are common terms used to define refrigerants [see, for example, Ralph C. Downing, Fluorocarbon Refrigerants Handbook, Prentice-Hall, Inc., Englewood Cliffs, N.J. (1988)]. Fluorocarbon compounds also include, however, compounds selected from the group consisting of fluoroether compounds, fluoroketone compounds, fluoroaromatic compounds and fluoroolefin compounds. Fluorocarbon compounds also include compounds wherein one or more optional substituents therein may be selected from one or more of bromine, chlorine and iodine.

A "halogen" is bromine, iodine, chlorine or fluorine.

A "heteroaryl" is an aryl group having a heteroatom.

A "heteroatom" is an atom other than carbon in the structure of an alkanyl, alkenyl, cyclic or aromatic compound.

A "hydrofluorocarbon compound" is a compound comprising fluorine, carbon and at least one hydrogen atom. A hydrofluorocarbon compound includes an HFC-hydrofluorocarbon compound ("HFC"), which consists solely of fluorine, carbon and hydrogen, as well as a hydrochlorofluorocarbon (HCFC) compound, wherein HFC and HCFC are common terms used to define refrigerants (see Ralph C. Downing, Fluorocarbon Refrigerants Handbook, supra). Hydrofluorocarbon compounds also include, however, compounds selected from the group consisting of hydrofluoroether compounds, hydrofluoroketone compounds, hydrofluoroaromatic compounds and hydrofluoroolefin compounds. Representative examples of hydrofluorocarbon compounds include methyl nonafluoroisobutyl ether, methyl nonafluorobutyl ether, ethyl nonafluoroisobutyl ether, ethyl nonafluorobutyl ether, and 3-ethoxy-1,1,1,2,3,4,4,5,5,6,6,6-dodecafluoro-2-trifluoromethylhexane. Hydrofluorocarbon compounds also include compounds wherein one or more optional substituents therein may be selected from one or more of bromine, chlorine and iodine.

An "ionic liquid" is an organic salt that is fluid at about 100° C. or below, as more particularly described in Science (2003) 302:792-793.

"Optionally substituted with at least one member selected from the group consisting of", when referring to an alkane, alkene, alkoxy, fluoroalkoxy, perfluoroalkoxy, fluoroalkyl, perfluoroalkyl, aryl or heteroaryl group or compound, means that one or more hydrogens on the carbon chain of the group or compound may be independently substituted with one or more of one or more members of the specified selection of substitutents. For example, a substituted —$C_2H_5$ group may, without limitation, be —$CF_2CF_3$, —$CH_2CH_2OH$ or —$CF_2CF_2I$.

A "refrigerant" is a substance such as an FC-fluorocarbon, an HFC-hydrofluorocarbon, a chlorofluorocarbon, a hydrochlorofluorocarbon, an alkane, an alkene, or an aromatic compound; or ammonia, carbon dioxide or other gases such as hydrogen, oxygen, nitrogen and argon, that is characterized by the property that, when it changes phase from liquid to vapor (i.e. when it evaporates), it removes heat from its surroundings; and when it changes phase from vapor to liquid (i.e. when it condenses), it adds heat to its surroundings. Refrigerant substances can also contain oxygen, or bromine, chlorine or iodine, as described above, for example, in relation to hydrofluorocarbon and fluorocarbon compounds.

"Selectivity", "separation factor" or "$\alpha_{ij}$" refers to the ratio of the infinite activity coefficient of component i to the infinite activity coefficient of component j where components i and j are present at an infinite degree of dilution in a mixture, such as a mixture that contains an entrainer and is being subjected to extractive distillation.

"Separating" or "to separate" refers to the removal of one component from a mixture. In various embodiments, separating or to separate may refer to the partial or complete removal of one component from the mixture. If further purification is required, one or more additional separation steps may be required to achieve complete removal. Such additional separation steps may include, for example, one or more of the steps of distillation, stripping, rectification, extraction, chromatography, and/or evaporation.

A "vacuum" is a pressure less than 1 bar but greater than $10^{-4}$ bar for practical use in equipment that is capable of performing an extractive distillation.

The present invention relates to a process for separating the components of a mixture that contains at least one hydrofluorocarbon compound. The hydrofluorocarbon compound may be selected from one or more members of the group consisting of HFC-hydrofluorocarbon compounds, hydrochlorofluorocarbon compounds, hydrofluoroether compounds, hydrofluoroketone compounds, hydrofluoroaromatic compounds, and hydrofluoroolefin compounds. In addition, the mixture contains at least one component selected from the group consisting of (1) at least one other hydrofluorocarbon compound; (2) at least one fluorocarbon compound; (3) at least one non-fluorinated hydrocarbon selected from the group consisting of $C_1$ to $C_4$ straight-chain, branched or cyclic alkanes and $C_1$ to $C_4$ straight-chain, branched or cyclic alkenes; (4) at least one inert gas selected from the group consisting of $N_2$, $O_2$, $CO_2$, CO, $NH_3$, Ar and $H_2$; and (5)

water. In addition, the mixture may optionally comprise one or more additives that include without limitation corrosion inhibitors or stabilizers.

A hydrofluorocarbon compound, as present in a mixture to be separated by the process of this invention, while containing at least one fluorine atom and at least one hydrogen atom, may contain any combination of those atoms in addition to carbon atoms, and may include compounds with carbon-carbon double bonds. Examples of HFC-hydrofluorocarbons often found in such a mixture to be separated include trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a) and fluoroethane (HFC-161). In one embodiment, HFC-hydrofluorocarbons present in a mixture as separated by a process of this invention may be selected from the group consisting of trifluoromethane (HFC-23), difluoromethane (HFC-32), pentafluoroethane (HFC-125), 1,1,1,2-tetrafluoroethane (HFC-134a), 1,1,1-trifluoroethane (HFC-143a) and 1,1-difluoroethane (HFC-152a).

A chlorofluorocarbon compound, as present in a mixture to be separated by a process of this invention, while containing at least one fluorine atom and at least one chlorine atom, may contain any combination of those atoms in addition to carbon atoms, and may include compounds with carbon-carbon double bonds. Examples of chlorofluorocarbon compounds that may be found in such a mixture to be separated include dichlorodifluoromethane (CFC-12) and chloropentafluoroethane (CFC-115).

A hydrochlorofluorocarbon compound, as present in a mixture to be separated by a process of this invention, while containing at least one fluorine atom, at least one chlorine atom and at least one hydrogen atom, may contain any combination of those atoms in addition to carbon atoms, and may include compounds with carbon-carbon double bonds. An example of a hydrochlorofluorocarbon compound that may be found in such a mixture to be separated includes chlorodifluoromethane (HCFC-22).

A fluorocarbon compound, as present in a mixture to be separated by a process of this invention, may have any combination of fluorine and carbon atoms, and may include compounds with carbon-carbon double bonds. Examples of fluorocarbon compounds that may be found in such a mixture to be separated include perfluoromethane (FC-14), perfluoroethane (FC-116), and perfluoropropane (FC-218).

Non-fluorinated hydrocarbon compounds that may be found in such a mixture to be separated include methane, ethane, ethylene, propane, cyclopropane, propylene, butane and isobutane.

A process of this invention may be employed, for example, to separate reclaimed mixtures of refrigerant gases to recover the individual component gases for subsequent reformulation. An azeotropic or constant-boiling mixture of refrigerant gases that is commonly encountered is a mixture of difluoromethane (HFC-32), pentafluoroethane (HFC-125) and 1,1,1,2-tetrafluoroethane (HFC-134a), as described in U.S. Pat. No. 5,709,092, and such a mixture could be advantageously processed for separation according to this invention. Another type of mixture that could be advantageously separated by a process of this invention is a mixture of one or more refrigerant gases with a contaminant such as air, of which the primary component gases are nitrogen and oxygen. Particular mixtures of refrigerant gases to which the process of this invention may be advantageously applied to effect separation include one or more of the group consisting of:

(i) HFC-32 and HFC-125,
(ii) HFC-125 and HFC-143a,
(iii) HFC-32 and HFC-143a,
(iv) CFC-115 and HFC-125.
(v) HFC-32 and HFC-134a, and
(iv) CFC-125 and HFC-134a.

Ionic liquids are organic compounds that are liquid at room temperature (approximately 25° C.). They differ from most salts in that they have very low melting points, and they tend to be liquid over a wide temperature range. Many of them are not soluble in non-polar hydrocarbons; are immiscible with water, depending on the anion; and many of them are highly ionizing (but have a low dielectric strength). Ionic liquids have essentially no vapor pressure, most are air and water stable, and they can either be neutral, acidic or basic. The properties of an ionic liquid can be tailored by varying the cation and anion. A cation or anion of an ionic liquid of the invention can in principle be any cation or anion such that the cation and anion together form an organic salt that is liquid at or below about 100° C.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.).

Representative examples of useful ionic liquids are described in sources such as *J. Chem. Tech. Biotechnol.,* 68:351-356 (1997); *Chem. Ind.,* 68:249-263 (1996); *J. Phys. Condensed Matter,* 5: (supp 34B):B99-B106 (1993); *Chemical and Engineering News, Mar.* 30, 1998, 32-37; *J. Mater. Chem.,* 8:2627-2636 (1998); *Chem. Rev.,* 99:2071-2084 (1999); and WO 05/113,702 (and references therein cited). In one embodiment, a library, i.e. a combinatorial library, of ionic liquids may be prepared, for example, by preparing various alkyl derivatives of the quaternary ammonium cation, and varying the associated anions. The acidity of the ionic liquids can be adjusted by varying the molar equivalents and type and combinations of Lewis acids.

Among the ionic liquids that are suitable for use herein to enhance the separation of components in an azeotropic, constant-boiling or close-boiling mixture are those that are capable of absorbing a hydrofluorocarbon, fluorocarbon, chlorofluorocarbon, hydrochlorofluorocarbon, fluoroether, fluoroketone, fluoroaromatic, or fluoroolefin compound, or an inert gas, a non-fluorinated hydrocarbon compound, or water. Ideally, to maximize separation, the ionic liquid should have distinctly lower solubility and diffusivity for at least one component of the mixture than for the other component(s) of the mixture.

In one embodiment of this invention, ionic liquids suitable for use therein include those having cations described generally by one or more of the following formulae:

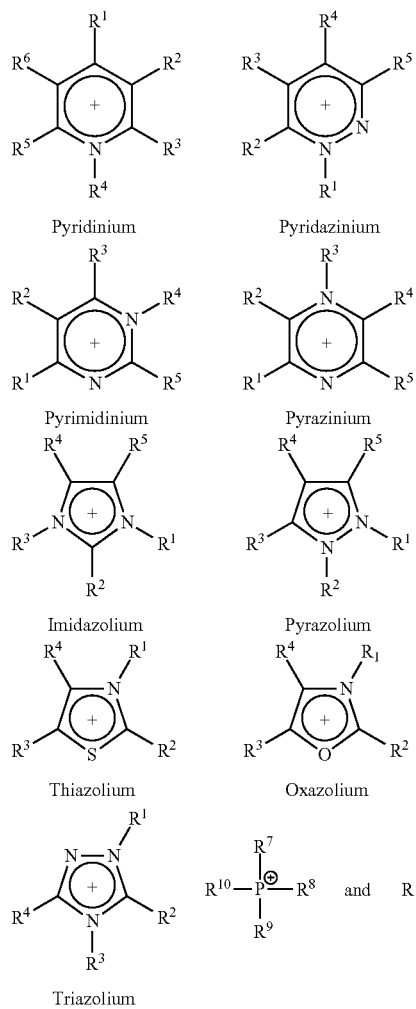

Phosphonium Ammonium wherein $R^1$, $R^2$, $R^3$, $R^4$, $R^5$ and $R^6$ are each independently selected from the group consisting of:
(i) H;
(ii) halogen;
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and
(vi) $C_6$ to $C_{25}$ substituted aryl, or $C_3$ to $C_{25}$ substituted heteroaryl having one to three heteroatoms independently selected from the group consisting of O, N, Si and S;
wherein said substituted aryl or substituted heteroaryl has one to three substituents independently selected from the group consisting of:
1. —$CH_3$, —$C_2H_5$, or $C_3$ to $C_{25}$ straight-chain, branched or cyclic alkane or alkene, optionally substituted with at least one member selected from the group consisting of Cl, Br, F I, OH, $NH_2$ and SH,
2. OH,
3. $NH_2$, and
4. SH; and
wherein $R^7$, $R^8$, $R^9$, and $R^{10}$ are each independently selected from the group consisting of:
(vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(ix) $C_6$ to $C_{25}$ unsubstituted aryl, or $C_3$ to $C_{25}$ unsubstituted heteroaryl having one to three heteroatoms independently selected from the group consisting of O, N, Si and S; and
(x) $C_6$ to $C_{25}$ substituted aryl, or $C_3$ to $C_{25}$ substituted heteroaryl having one to three heteroatoms independently selected from the group consisting of O, N, Si and S;
wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH; and
wherein optionally at least two of $R^1$, $R^2$, $R^3$, $R^4$, $R^5$, $R^6$, $R^8$, $R^9$, and $R^{10}$ can together form a cyclic or bicyclic alkanyl or alkenyl group.

In another embodiment, ionic liquids suitable for use herein include those having fluorinated cations wherein at least one member selected from $R^1$, $R^2$, $R^3$, $R^4$, $R^5$, $R^6$, $R^7$, $R^8$, $R^9$ and $R^{10}$, as described above, comprises $F^-$.

In yet another embodiment, ionic liquids suitable for use herein comprise anions selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and preferably any fluorinated anion. Fluorinated anions suitable for use herein include $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$; and $F^-$. In yet another embodiment, ionic liquids suitable for use herein comprise a cation selected from the group consisting of pyridinium, pyridazinium, pyrimidinium, pyrazinium, imidazolium, pyrazolium, thiazolium, oxazolium, triazolium, phosphonium, and ammonium ions, as described above; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and any fluorinated anion. In yet another embodiment, ionic liquids suitable for use herein comprise a cation selected from the group consisting of pyridinium, pyridazinium, pyrimidinium, pyrazinium, imidazolium, pyrazolium, thiazolium, oxazolium, triazolium, phosphonium, and ammonium ions, as described above; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In still another embodiment, ionic liquids suitable for use herein have a cation selected from the group consisting of pyridinium, pyridazinium, pyrimidinium, pyrazinium, imidazolium, pyrazolium, thiazolium, oxazolium, triazolium, phosphonium, and ammonium ions, as described above, wherein at least one member selected from $R^1, R^2, R^3, R^4, R^5, R^6, R^7, R^8, R^9$, and $R^{10}$ comprises $F^-$; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and any fluorinated anion. In still another embodiment, ionic liquids suitable for use herein have a cation selected from the group consisting of pyridinium, pyridazinium, pyrimidinium, pyrazinium, imidazolium, pyrazolium, thiazolium, oxazolium, triazolium, phosphonium, and ammonium ions, as described above, wherein at least one member selected from $R^1, R^2, R^3, R^4, R^5, R^6R^7, R^8, R^9$, and $R^{10}$ comprises $F^-$; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In still another embodiment, ionic liquids suitable for use in a separation process of this invention include those comprising:

a) imidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, $[CH_3OSO_3]^-$;

b) 1-butyl-3-methylimidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

c) 1-propyl-2,3-dimethylimidazolium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

d) 1-ethyl-3-methylimidazolium as the cation, and $[(CF_3CF_2SO_2)_2N]^-$, $[PF_6]^-$, and $[HCF_2CF_2SO_3]^-$ as the anion;

e) 1-propyl-3-methylpyridinium as the cation, and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

f) 1,2-dimethyl-3-propylimidazolium as the cation, and an anion selected from the group consisting of $[(CF_3SO_2)_3C]^-$ and $[(CF_3SO_2)_2N]^-$;

g) 3-methyl-1-propylpyridinium as the cation, and $[(CF_3SO_2)_2N]^-$ as the anion;

h) 1-butyl-3-methylpyridinium as the cation, and $[(CF_3SO_2)_2N]^-$ as the anion;

i) 1-dodecyl-3-methylimidazolium as the cation, and $[HCF_2CF_2SO_3]^-$ as the anion;

j) 1-heptyl-3-methylimidazolium as the cation, and $[HCF_2CF_2SO_3]^-$ as the anion;

k) tetradecyl(trihexyl)phosphonium as the cation, and $[CF_3CF_2OCFHCF_2SO_3]^-$ or $[CF_3OCFHCF_2SO_3]^-$ as the anion;

l) tributyl(tetradecyl)phosphonium as the cation, and $[CF_3HFCCF_2SO_3]^-$ as the anion;

m) 1,3-dioctylimidazolium or 1-octyl-3-methylimidazolium as the cation, and $[I]^-$ as the anion.

Other cations suitable as part of an ionic liquid as used herein include 1,2-dimethylpyridinium, 1-methyl-2-ethylpyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, N-butylpyridinium, 1-butyl-4-methylpyridinium, 1,3-dimethylimidazolium, 1,2,3-trimethylimidazolium, 1-n-butyl-3-methylimidazolium, 1,3,4,5-tetramethylimidazolium, 1,3,4-trimethylimidazolium, 2,3-dimethylimidazolium, 1-butyl-2,3-dimethylimidazolium, 3,4-dimethylimidazolium, 2-ethyl-3,4-dimethylimidazolium, 3-methyl-2-ethylimidazol, 3-butyl-1-methylimidazolium, 3-butyl-1-ethylimidazolium, 3-butyl-1,2-dimethylimidazolium, 1,3-di-n-Butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethylimidazolium, 1-methyl-3-octylimidazolium and 1-decyl-3-methylimidazolium ions.

As the process of this invention is used for the purpose of separating a hydrofluorocarbon compound from the other components in a mixture in which it is contained, ionic liquids that are suitable for use for such purpose will include those that are capable of absorbing one or more components of such mixture to a differing extent than other component(s), which components may include one or more hydrofluorocarbon compounds, and/or a hydrochlorofluorocarbon, hydrofluoroether, hydrofluoroketone, hydrofluoroaromatic or hydrofluoroolefin compound. Ionic liquids suitable for use for the purpose of separating a mixture component as aforesaid include those having a cation selected from the group consisting of pyridinium, pyridazinium, pyrimidinium, pyrazinium, imidazolium, pyrazolium, thiazolium, oxazolium, triazolium, phosphonium, and ammonium ions, as described above. In an embodiment in which a mixture component is a hydrofluorocarbon compound selected from the group consisting of HFC-23, HFC-32, HFC-125, HFC-134, HFC-134a, HFC-143a, HFC-152a, HFC-161, HCFC-22, and a hydrofluoroether, hydrofluoroketone, hydrofluoroaromatic and hydrofluoroolefin compound, ionic liquids suitable for use for the purpose of separating a mixture component as aforesaid include those having a cation selected from the group consisting of pyridinium, pyridazinium, pyrimidinium, pyrazinium, imidazolium, pyrazolium, thiazolium, oxazolium, triazolium, phosphonium, and ammonium ions, as described above.

In an embodiment in which a mixture component is a hydrofluorocarbon compound selected from the group consisting of HFC-23, HFC-32, HFC-125, HFC-134, HFC-134a, HFC-143a, HFC-152a, HFC-161, HCFC-22, and a hydrofluoroether, hydrofluoroketone, hydrofluoroaromatic and hydrofluoroolefin compound, ionic liquids suitable for use for the purpose of separating a mixture component as aforesaid also include those selected from the group consisting of:

a) an ionic liquid having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above;

b) an ionic liquid having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above wherein at least one member selected from $R^1$ through $R^{10}$ comprises fluorine;

c) an ionic liquid having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above; and having an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion;

d) an ionic liquid having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above; and having an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$;

e) an ionic liquid having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above wherein at least one member selected from $R^1$ through $R^{10}$ comprises fluorine; and having an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, and any fluorinated anion; and f) an ionic liquid having a cation selected from the group consisting of pyridinium, pyridazinium, pyrimidinium, pyrazinium, imidazolium, pyrazolium, thiazolium, oxazolium, triazolium, phosphonium, and ammonium ions, having $R^1$ through $R^{10}$ independently selected as described above wherein at least one member selected from $R^1$ through $R^{10}$ comprises fluorine; and having an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In an embodiment in which a mixture component is a hydrofluorocarbon compound selected from the group consisting of HFC-23, HFC-32, HFC-125, HFC-134, HFC-134a, HFC-143a, HFC-152a, HFC-161, HCFC-22, and a hydrofluoroether, hydrofluoroketone, hydrofluoroaromatic and hydrofluoroolefin compound, ionic liquids suitable for use for the purpose of separating a mixture component as aforesaid also include those selected from the group consisting of:

g) an ionic liquid having an imidazolium cation or a fluorinated imidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

h) an ionic liquid having a 1-ethyl-3-methylimidazolium or a fluorinated 1-ethyl-3-methylimidazolium as the cation, and $[(CF_3CF_2SO_2)_2N]^-$ as the anion;

i) an ionic liquid having a 1-butyl-3-methylimidazolium cation or a fluorinated 1-butyl-3-methylimidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

j) an ionic liquid having a 1-propyl-2,3-dimethylimidazolium cation or a fluorinated 1-propyl-2,3-dimethylimidazolium cation; and an anion selected from the group consisting of $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, and $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$;

k) an ionic liquid having a 1-propyl-3-methylimidazolium cation or a fluorinated 1-propyl-3-methylimidazolium cation; and an anion selected from the group consisting of $[BF_4]^-$,

[PF$_6$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, and [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$;

l) an ionic liquid having a 1,2-dimethyl-3-propylimidazolium cation or a fluorinated 1,2-dimethyl-3-propylimidazolium cation; and an anion selected from the group consisting of [(CF$_3$SO$_2$)$_3$C]$^-$ and [(CF$_3$SO$_2$)$_2$N]$^-$;

m) an ionic liquid having a 3-methyl-1-propylpyridinium cation or a fluorinated 3-methyl-1-propylpyridinium cation, and [(CF$_3$SO$_2$)$_2$N]$^-$ as the anion;

n) an ionic liquid having a 1-butyl-3-methylpyridinium cation or a fluorinated 1-butyl-3-methylpyridinium cation, and [(CF$_3$SO$_2$)$_2$N]$^-$ as the anion;

o) an ionic liquid having a 1-dodecyl-3-methylimidazolium cation or a fluorinated 1-dodecyl-3-methylimidazolium cation, and [HCF$_2$CF$_2$SO$_3$]$^-$ as the anion;

p) an ionic liquid having a 1-heptyl-3-methylimidazolium cation or a fluorinated 1-heptyl-3-methylimidazolium cation, and [HCF$_2$CF$_2$SO$_3$]$^-$ as the anion;

q) an ionic liquid having a tetradecyl(trihexyl)phosphonium cation or a fluorinated tetradecyl(trihexyl)phosphonium cation, and [CF$_3$CF$_2$OCFHCF$_2$SO$_3$]$^-$ or [CF$_3$OCFHCF$_2$SO$_3$]$^-$ as the anion;

r) an ionic liquid having a tributyl(tetradecyl)phosphonium cation or a fluorinated tributyl(tetradecyl)phosphonium cation, and [CF$_3$HFCCF$_2$SO$_3$]$^-$ as the anion; and s) an ionic liquid having a cation selected from the group consisting of 1,3-dioctylimidazolium, 1-octyl-3-methylimidazolium, fluorinated 1,3-dioctylimidazolium, or fluorinated 1-octyl-3-methylimidazolium ions, and [I]$^-$ as the anion.

In yet another embodiment of the invention, when the separation process of this invention is used for the purpose of separating two or more refrigerants that are in a mixture, the process will involve the use of an ionic liquid that is capable of absorbing one or more of the refrigerants in the mixture to a differing extent than other of the refrigerants. The refrigerants may be selected from the group consisting of hydrofluorocarbon, hydrochlorofluorocarbon, chlorofluorocarbon, and fluorocarbon compounds. In alternative embodiments, two or more of the refrigerants may be selected from the group consisting of HFC-23, HFC-32, HFC-125, HFC-134, HFC-134a, HFC-143a, HFC-152a, HFC-161, HCFC-22, FC-14, FC-116, FC-218, CFC-12, and CFC-115. In other embodiments, two or more of the refrigerants may be selected from the group consisting of HFC-23, HFC-32, HFC-125, HFC-134, HFC-134a, HFC-143a, HFC-152a, HFC-161, HCFC-22, FC-14, FC-116, FC-218, CFC-12, and CFC-115, and ionic liquids suitable for use for the purpose of separating refrigerants as mixture components as aforesaid include those having a cation selected from the group consisting of pyridinium, pyridazinium, pyrimidinium, pyrazinium, imidazolium, pyrazolium, thiazolium, oxazolium, triazolium, phosphonium, and ammonium ions, as described above.

In various other embodiments of this invention, an ionic liquid formed by selecting any of the individual cations described or disclosed herein, and by selecting any of the individual anions described or disclosed herein, may be used for the purpose of effecting the separation of any of the hydrofluorocarbon compounds described or disclosed herein from a mixture in which that hydrofluorocarbon compound is contained. Correspondingly, in yet other embodiments, a subgroup of ionic liquids formed by selecting (i) a subgroup of any size of cations, taken from the total group of cations described and disclosed herein in all the various different combinations of the individual members of that total group, and (ii) a subgroup of any size of anions, taken from the total group of anions described and disclosed herein in all the various different combinations of the individual members of that total group, may be used for the purpose of effecting the separation of any of the hydrofluorocarbon compounds described or disclosed herein from a mixture in which that hydrofluorocarbon compound is contained. In forming an ionic liquid, or a subgroup of ionic liquids, by making selections as aforesaid, the ionic liquid or subgroup will be used in the absence of the members of the group of cations and/or anions that are omitted from the total group thereof to make the selection, and, if desirable, the selection may thus be made in terms of the members of the total group that are omitted from use rather than the members of the group that are included for use. In yet other embodiments, the mixture from which the hydrofluorocarbon compound is separated by use of an ionic liquid, or subgroup of ionic liquids, formed by making selections as aforesaid, may also contain any of the other compounds described or disclosed herein.

Systems of particular interest in this invention are those in which one or more hydrofluorocarbons is separated from a mixture containing one, two or more other hydrofluorocarbons by the addition to the mixture of at least one fluorinated ionic liquid, such as an ionic liquid that has a fluorinated anion, a fluorinated cation or both, in view of what may be useful interactions between and/or among the various fluorinated species that may increase the solubility of a hydrofluorocarbon in the ionic liquid.

The process of this invention to separate the components of an azeotropic or constant- or close-boiling mixture involves contacting the mixture with an ionic liquid. This is advantageous because at least one of the components of the mixture will be less soluble in the ionic liquid than the other component(s), and preferably much less soluble. This difference in solubility facilitates the separation of the lower-solubility component from the mixture because when that component is removed, such as by volatilization, the more-soluble component will be removed to a more limited extent, and will preferably not be removed at all, because to the extent that it is soluble in the ionic liquid, it will tend to remain in, and not be removed from, the mixture.

The process of this invention may be performed, for example, by a technique such as extractive distillation. In extractive distillation, as in conventional distillation, at least one component of the mixture is caused, through temperature and pressure control, to be volatilized, and the volatilized component(s) is captured in a separate stream in which it is condensed apart from, and is thus removed from, the mixture. In extractive distillation, however, there is added to the mixture a miscible, high boiling, relatively nonvolatile component, the solvent or entrainer, that has low latent heat of vaporization, does not form an azeotrope with any of the components in the mixture, and does not chemically react with any of the components in the mixture. The entrainer is specially chosen to interact differently with the various components of the mixture, thereby altering their relative volatilities and "breaking" the azeotrope in which they would otherwise exist. The entrainer is chosen to be a substance in which one or more of the components of the mixture is more soluble, and preferably much more soluble, than at least one other component of the mixture. A component that is less soluble in the entrainer may, as a result, be more easily volatilized and separated from the mixture than a component that is more soluble in the entrainer. The tendency that the components of an azeotrope would ordinarily have to volatilize in the essentially the same compositional ratio as they possess in liquid from is thus altered by the presence of the entrainer, which, by solubilizing at least one component of the mixture to a greater extent than at least one other component, causes a corresponding change in the compositional content of the stream of volatiles liberated from the mixture at a selected temperature and pressure. The component(s) that are caused to be more volatile than others by the presence of the entrainer in the mixture are then removed from the mixture as vapor in much higher concentration than the other components at the selected temperature and pressure. The more soluble, less volatile component(s) remain in the mixture with the entrainer, and another criterion for selection of the entrainer is that it be a substance that is easily separated from the remaining high-solubility, low-volatility component(s) of the mixture.

In various embodiments, it may be desirable to select as the entrainer a substance that causes the lower-boiling of two components in a mixture to become the more volatile of the two components as well. For example, a substance having greater chemical similarity to the higher-boiling of two components than to the lower-boiling may be selected as the entrainer in such an embodiment. In various other embodiments, criteria that may be considered in evaluating a substance for selection as an entrainer is whether the substance causes a positive deviation from Raoult's law with the lower-boiling of two components, or causes a negative deviation from Raoult's law with the higher-boiling of the two components.

Mixtures of entrainers, and thus mixtures of ionic liquids as entrainers, may also be useful for achieving a desired extent of separation. In one embodiment, a mixture of entrainers may be selected wherein one entrainer has a high selectivity for the higher-volatility of the two components, and the other entrainer has a high capacity to solubilize that component. In another embodiment, a mixture of ionic liquids may be used to separate the components of a mixture comprising at least two hydrofluorocarbon compounds by using multiple, discrete separation steps.

When the separation process of this invention is performed by extractive distillation, it may be advantageously performed in a distillation column such as is shown in the schematic diagram of FIG. 1. In the column of FIG. 1, separator elements 1 are used for the separation from the entrainer of the top product, which is the mixture component that is made more volatile by the presence of the entrainer in the mixture. Use of an ionic liquid as the entrainer has the advantage of essentially eliminating the presence of the entrainer in the overhead product 7 because of the negligible volatility of an ionic liquid.

The flow of the entrainer enters at inlet 2, which is preferably located in the enriching section close to the top of the column below the condenser, or at the bottom of the rectifying section, wherein any amount of the entrainer that has unexpectedly volatilized is separated from the higher-volatility component of the mixture. The ionic liquid as entrainer then proceeds in a countercurrent flow direction downward in the column relative to the upward flow of the higher-volatility component, and perhaps other components of the mixture to be separated. The mixture enters at inlet 4, above the stripping section, where any of the higher-volatility component that is still admixed with the entrainer is finally vaporized. The inlet feed of the mixture to be separated may be in liquid or gaseous form, and, if the mixture is in liquid form when fed into the column, the higher-volatility component(s) thereof will be volatilzed by the temperature and pressure conditions of the column, which will have been selected for that purpose. The vapors moving upward in the column are continuously enriched in content of the higher-volatility component of the mixture, and the liquid moving downward in the column is continuously depleted in content of that higher-volatility component.

Separator elements 3 and 5 contain a useful number of stages along the height of the column at which there is thorough gas-liquid contacting, which is desirable for the purpose of obtaining extensive separation of a higher-volatility component, which exits the column as the overhead product 7, from a lower-volatility component, which exits the column together with the entrainer as the bottom product 6. For example, where a mixture contains as components both members of the refrigerant pair HFC-32 and HFC-125, HFC-125 is the lower-solubility component that is separated from the mixture while HFC-32 is preferentially solubilized by the entrainer.

Separator elements can be either plates, or ordered or disordered packings. In either event, the purpose is to provide a downward cascade of the liquid entrainer to contact the rising stream of vaporized high-volatility component. If plates are used, the liquid may flow over the edge of one plate onto another, or the liquid may flow through the same holes in the plates through which the volatilized component rises. In either case, the objective is to achieve maximum residence time of gas-liquid contact consistent with providing a rate of upward vapor flow that is high enough to prevent the column from being flooded by the downcoming liquid, but is not so high that the vapor is pushed out of the column without sufficient time to contact the liquid.

There is, in terms of the amount of the mixture to be separated, a minimum amount of the entrainer that is needed to "break" the azeotropic, or the constant- or close-boiling, characteristics of the mixture, and enable the separation of at least one of the components from the mixture from the others in a yield and at a rate that is commercially feasible. In a ratio of the amount of entrainer to the amount of feed, where the amount of entrainer used in the ratio is the minimum amount described above, the value of the ratio may be set in the range of about 2 to about 4. Feed ratios above 5 are frequently found to offer no particular advantage in terms of being able to reduce the number of stages in a column.

The entrainer is then removed from the mixture together with the higher-volatility component in a separate step, and is recycled to the column for re-entry into the column at inlet 2. The entrainer may be separated from the bottom product 6 using various separating operations including regeneration by simple evaporation. Thin film evaporators, such as falling-film or rotary evaporators, are commonly used for continuous evaporation. In discontinuous concentration processes, two evaporator stages are run alternately so that regenerated ionic liquid, as entrainer, can be returned continuously to the distillation column. The entrainer can also be regenerated by means of a stripping column since the vapor pressure of the ionic liquid is essentially zero. An alternative means of recovering an ionic liquid as entrainer takes advantage of the fact that many ionic liquids can solidify below 0° C. In these cases, low cost separation of the ionic liquid can be achieved by cooling to form a solid phase. The bottom product can also be precipitated using techniques such as cooling, evaporative, or vacuum crystallization.

These and other aspects of extractive distillation are further discussed in well-known sources such as *Perry's Chemical Engineers' Handbook*, $7^{th}$ Ed. (Section 13, "Distillation", McGraw-Hill, 1997).

When the separation process of this invention is performed by extractive distillation, more than one distillation column may be required in systems in which a mixture contains multiple components to be separated. For example, non-close-boiling components may be separated and removed from the mixture using a first distillation column, and azeotropic mixtures can then be separated using a second distillation column. An ionic liquid may be used as an entrainer for one or both of the distillation columns. For example, where it is desirable to separate a mixture comprising two refrigerants using one ionic liquid, one refrigerant may be recovered from the top of the column whereas the second refrigerant and ionic liquid can be recovered from the bottom of the column. The mixture comprising the second refrigerant and the ionic liquid can then be separated using a second distillation column (or flash tank); the second refrigerant can be recovered from the top of the second column (or flash tank), and the ionic liquid can be recovered from the bottom of the column (or flash tank) and recycled back to the first distillation column.

In other exemplary embodiments, it may be desired to separate a mixture containing a hydrofluorocarbon compound and a hydrocarbon, and, in such case, the hydrocarbon may be recovered from the top of the distillation column; and the hydrofluorocarbon compound may be recovered from the bottom of the column with the entrainer, such as an ionic liquid. The hydrofluorocarbon compound may then be separated from the entrainer using a flash tank, and the entrainer may again be recycled to the distillation compound. Where it is desired to separate a mixture comprising two refrigerants and air, the air may be separated by extractive distillation and recovered from the top of the column. An ionic liquid, as used as the entrainer in the process, may be separated from the mixture comprising the refrigerants using a flash tank, and the refrigerants may then be separated using a second distillation column.

The ability to separate a binary mixture of two components i and j by distillation can be determined by calculating their selectivity. The closer the selectivity is to the value of one, the more difficult it is for the components of the mixture to be separated by conventional distillation. Therefore, an extractive distillation method may be used to enhance the separation efficiency. In extractive distillation, an entrainer influences the separation by selectively absorbing or dissolving one or more of the components in the mixture. According to the present invention, the selectivity of an ionic liquid for a binary mixture composed of i and j is defined as the ratio of the infinite activity coefficient of component i to the infinite activity coefficient of component j, where components i and j are present at an infinite degree of dilution in the ionic liquid entrainer. In general the selectivity can be greater than or less than 1 depending on whether the low boiler or high boiler is in the numerator. Normally the low boiler is placed in the numerator so that the selectivity is shown as a value greater than 1. In order to achieve separation, a selectivity of greater than about 1.0 is required. In one embodiment of the invention, the addition of an ionic liquid to the mixture provides a selectivity greater than about 1.3; and in another embodiment of the invention, the addition of an ionic liquid to the mixture provides a selectivity greater than about 2.0.

When the separation process of this invention is performed by extractive distillation, the individual components of the mixture may have respective concentrations ranging from about 0.05 to about 99.95 mole percent relative to the total weight of all components in the mixture plus the entrainer depending on their location at any particular time in the column, at which location and time they may be subjected to a temperature in the range of from the reboiler temperature to the condenser temperature, and a pressure in the range of from vacuum to the critical pressure. Extractive distillation processes operate at varying feed, reboiler, and condenser temperatures depending on the appropriate conditions for optimum separation. A typical extractive distillation process might operate with a condenser and or feed composition chilled by water to a temperature of 5 to 10° C., or chilled by brine or ethylene glycol to even lower temperatures of 0 to −40° C. In some cases, if the extractive distillation column operates at close to the normal boiling point of a compound at about 1 atmosphere pressure, the feed and or the condenser may cool the gas to even lower temperatures of −40 to −80° C. The reboiler can operate over a wide temperature range depending on the operating pressure of the column and the identity of the compound(s) being separated, which in the case of fluorinated compound could be a temperature range of from about −80 to about 240° C.

For example, over a temperature range of from about −80 to about 240° C., the following fluorinated compounds may have a concentration in a mixture with an ionic liquid in the range of from about 0.1 to about 99.9 mole percent, relative to the total weight of the compound and the ionic liquid, at a pressure in the range of from about vacuum up to about the pressure value specified for each compound as follows:

| | |
|---|---|
| HFC-32 | 57.8 bar, |
| HFC-125 | 36.2 bar, |
| HFC-134a | 40.6 bar, |
| HFC-143a | 37.6 bar, and |
| HFC-152a | 45.2 bar. |

As a result, in the process of this invention, where the mixture comprises a hydrofluorocarbon compound selected from the above list; and where the mixture is subjected during separation to a temperature in the range of from about −80 to about 240° C.; the mixture may also be subjected during separation to a pressure in the range of from about vacuum up to about the pressure value specified for each compound, as follows:

| | |
|---|---|
| HFC-32 | 57.8 bar, |
| HFC-125 | 36.2 bar, |
| HFC-134a | 40.6 bar, |
| HFC-143a | 37.6 bar, and |
| HFC-152a | 45.2 bar. |

Other substances that can form a mixture with a hydrofluorocarbon compound may be present in such a mixture at a concentration that may vary over a range of from about 0.05 to about 99.95 mole percent, relative to the total weight of all components in the mixture including an entrainer such as an ionic liquid. When such a mixture is fed to a column for separation in an extractive distillation process, the concentration of the component will vary according to the conditions of temperature and pressure, where the temperature may vary over a range from the reboiler temperature to the condenser temperature, and the pressure may vary over a range from vacuum to the critical pressure. Examples of such substances are shown in Table 1, which contains boiling point and critical point data for those substances obtained from Reid, R. C. et al, supra; and REFPROP V. 7 [Lemmon et al (NIST Reference Fluid Thermodynamic and Transport Properties—REFPROP, Version 7.0 User's Guide, U.S. Department of Commerce, Technology Administration, National Institute of Standards and Technology, Standard Reference Data Program, Gaithersburg, Md., 2002)].

TABLE 1

| Component | Boiling Point Temperature (°C.) | Critical Point Pressure (bar) |
|---|---|---|
| Perfluoromethane (FC-14) | −128.1 | 37.5 |
| Perfluoroethane (FC-116) | −78.2 | 30.5 |
| Perfluoropropane (FC-218) | −36.8 | 26.7 |
| Dichlorodifluoromethane (CFC-12) | −29.8 | 41.4 |
| Chloropentafluoroethane (CFC-115) | −38.9 | 31.2 |
| Hydrochlorodifluoromethane (HCFC-22) | −40.8 | 49.9 |
| Fluoromethane (HFC-41) | −78.1 | 59.0 |
| 1,1,1,3,3,3-hexafluoropropane (HFC-236fa) | −1.4 | 32.0 |
| 1,1,1,2,3,3,3-heptafluoropropane (HFC-227ea) | −16.5 | 29.3 |
| Carbon Dioxide | −78.4 | 73.7 |
| Ammonia | −33.3 | 113.3 |
| Nitrogen | −195.8 | 33.9 |
| Hydrogen chloride | −85.05 | 83.1 |
| Fluorine | −188.2 | 52.2 |
| Hydrogen fluoride | 19.9 | 64.8 |
| Oxygen | −183 | 50.4 |
| Hydrogen | −252.8 | 13.2 |
| Argon | −185.9 | 46.0 |
| Methane | −161.5 | 46.0 |
| Ethane | −88.6 | 48.7 |
| Ethylene | −103.9 | 50.4 |
| Propane | −42.1 | 42.4 |
| Propylene | −47.7 | 46.6 |
| Cyclopropane | −32.9 | 54.9 |
| Butane | −0.6 | 37.9 |
| Isobutane | −11.7 | 36.4 |
| H$_2$O | 100 | 220 |

The following examples are presented to illustrate the advantages of the present invention and to assist one of ordinary skill in making and using the same. These examples illustrate the preparation of various ionic liquids, and illustrate the desirable properties of various ionic liquids in relation to their use for the purpose of enhancing the separation of various fluorinated compounds as may be present in a mixture. These examples are not intended in any way to limit the scope of the disclosure. In this work, both selectivities (see Example 1) and Aspen® (Aspen Technology, Inc., Version 13.1, Cambridge, Mass.) modeling (see Example 2) were used to determine the ability to separate hydrofluorocarbon compounds from a mixture.

General Methods and Materials

1-Butyl-3-methylimidazolium hexafluorophosphate ([bmim][PF$_6$], C$_8$H$_{15}$N$_2$F$_6$P, molecular weight 284 g mol$^{-1}$), 1-butyl-3-methylimidazolium tetrafluoroborate ([bmim][BF$_4$], C$_8$H$_{15}$N$_2$F$_4$B, molecular weight 226 g mol$^{-1}$), 1,2-dimethyl-3-propylimidazolium tris(trifluoromethylsulfonyl) methide ([dmpim][tTFMSmethide], C$_{12}$H$_{15}$N$_2$F$_9$O$_6$S$_3$, molecular weight 550 g mol$^{-1}$), 1,2-dimethyl-3-propylimidazolium bis(trifluoromethylsulfonyl)imide ([dmpim][bTFMSimide], C$_{10}$H$_{15}$N$_3$F$_6$O$_4$S$_2$, molecular weight 419 g mol$^{-1}$), 1-ethyl-3-methylimidazolium bis(pentafluoroethylsulfonyl) imide ([emim][bPFESimide], C$_{10}$H$_{11}$N$_3$F$_{10}$O$_4$S$_2$, molecular weight 491.33 g mol$^{-1}$), 1-propyl-3-methylpyridinium bis(trifluoromethylsulfonyl)imide ([pmpy][bTFMSimide], C$_{11}$H$_{14}$N$_2$F$_6$O$_4$S$_2$, molecular weight 416.36 g mol$^{-1}$), 1-ethyl-3-methylimidazolium hexafluorophosphate ([emim][PF$_6$], C$_6$H$_{11}$F$_6$N$_2$P, molecular weight 265.13 g mol$^{-1}$), 1-ethyl-3-methylimidazolium bis(trifluoromethylsulfonyl) imide ([emim][BMeI], C$_8$H$_{11}$F$_6$N$_3$O$_4$S$_2$, molecular weight 197.98 g mol$^{-1}$), 1-butyl-3-methylpyridinium bis(trifluoromethylsulfonyl)imide ([BMPy][bTFMSimide], C$_{12}$H$_{16}$F$_6$N$_2$O$_4$S$_2$, molecular weight 430.39 g mol$^{-1}$) were each obtained from Fluka Chemika (may be obtained from Sigma-Aldrich, St. Louis, Mo.) with a purity of >96 to 97% each. Trifluoromethane (HFC-23), difluoromethane (HFC-32, CH$_2$F$_2$, molecular weight 52.02 g mol$^{-1}$), pentafluoroethane (HFC-125, C$_2$HF$_5$, molecular weight 120.02 g mol$^{-1}$), 1,1,1,2-tetrafluoroethane (HFC-134a, C$_2$H$_2$F$_4$, molecular weight 102.03 g mol$^{-1}$), 1,1,1-trifluoroethane (HFC-143a, C$_2$H$_3$F$_3$, molecular weight 82.04 g mol$^{-1}$), and 1,1-difluoroethane (HFC-152a, C$_2$H$_4$F$_2$, molecular weight 66.05 g mol$^{-1}$) were obtained from DuPont Fluorochemicals (Wilmington, Del.), with a minimum purity of 99.99%. A molecular sieve trap was installed to remove trace amounts of water from the gases and each of the ionic liquids tested were degassed prior to making solubility measurements.

The following nomenclature and abbreviations are used:
C=concentration (mol·m$^{-3}$)
$C_b$=buoyancy force (N)
$C_f$=correction factor (kg)
$C_o$=initial concentration (mol·m$^{-3}$)
$C_s$=saturation concentration (mol·m$^{-3}$)
<C>=space-averaged concentration (mol·m$^{-3}$)
D=diffusion constant (m$^2$·s$^{-1}$)
g=gravitational acceleration (9.80665 m·s$^{-2}$)
L=length (m)
$m_a$=mass absorbed (kg)
$m_i$=mass of i-th species on sample side of balance (kg)
$m_j$=mass of j-th species on counterweight side of balance (kg)
$m_{IL}$=mass of ionic liquid sample (kg)
$MW_i$=molecular weight of i-th species (kg·mol$^{-1}$)
N=n-th number component
P=pressure (MPa)
$P_0$=initial pressure (MPa)
t=time (s)
$T_{ci}$=critical temperature of i-th species (K)
$T_i$=temperature of i-th species (K)
$T_j$=temperature of j-th species (K)
$T_s$=temperature of sample (K)
$V_i$=volume of i-th species (m$^3$)
$V_{IL}$=volume of ionic liquid (m$^3$)
$V_m$=liquid sample volume (m$^3$)
$\tilde{V}_g$=molar volume of gas (m$^3$·mol$^{-1}$)
$\tilde{V}_i$=molar volume of i-th species (m$^3$·mol$^{-1}$)
$\tilde{V}_{IL}$=molar volume of ionic liquid (m$^3$·mol$^{-1}$)
$\tilde{V}_m$=molar volume of mixture (m$^3$·mol$^{-1}$)
$\tilde{V}_0$=initial molar volume (m$^3$·mol$^{-1}$)
$\Delta\tilde{V}$=change in molar volume (m$^3$·mol$^{-1}$)
$x_i$=mole fraction of i-th species
z=depth (m)
$\lambda_n$=eigenvalue (m$^{-1}$)
$\rho_g$=density of gas (kg·m$^{-3}$)
$\rho_i$=density of i-th component on sample side of balance (kg·m$^{-3}$)
$\rho_j$=density of j-th component on counter weight side of balance (kg·m$^{-3}$)
$\rho_{air}$=density of air (kg·m$^{-3}$)
$\rho_s$=density of sample (kg·m$^{-3}$)
Units
Pa≡Pascal
MPa≡Mega Pascal
mol≡mole
m≡meter
cm≡centimeter
K≡Kelvin
N≡Newton
J≡Joule
kJ≡kilojoule
kg≡kilogram
mg≡milligram µg=microgram
T≡temperature
P≡pressure
mbar≡millibar
min≡minute
° C.≡degrees Centigrade
sec≡second
kW≡kilowatt
kg/s≡kilogram/second In the following description, (A)-(D) provide syntheses for anions of ionic liquids that are useful as entrainers for the invention, and (E)-(U) provide syntheses for ionic liquids useful as entrainers for the invention.

Preparation of Anions Not Generally Available Commercially (A) Synthesis of potassium 1,1,2,2-tetrafluoroethanesulfonate (TFES-K) ([HCF$_2$CF$_2$SO$_3$]$^-$): (A) Synthesis of potassium 1,1,2,2-tetrafluoroethanesulfonate (TFES-K)

A 1-gallon Hastelloy® C276 reaction vessel was charged with a solution of potassium sulfite hydrate (176 g, 1.0 mol), potassium metabisulfite (610 g, 2.8 mol) and deionized water (2000 ml). The pH of this solution was 5.8. The vessel was cooled to 18 degrees C., evacuated to 0.10 MPa, and purged with nitrogen. The evacuate/purge cycle was repeated two more times. To the vessel was then added tetrafluoroethylene (TFE, 66 g), and it was heated to 100 degrees C. at which time the inside pressure was 1.14 MPa. The reaction temperature was increased to 125 degrees C. and kept there for 3 h. As the TFE pressure decreased due to the reaction, more TFE was added in small aliquots (20-30 g each) to maintain operating pressure roughly between 1.14 and 1.48 MPa. Once 500 g (5.0 mol) of TFE had been fed after the initial 66 g precharge, the vessel was vented and cooled to 25 degrees C. The pH of the clear light yellow reaction solution was 10-11. This solution was buffered to pH 7 through the addition of potassium metabisulfite (16 g).

The water was removed in vacuo on a rotary evaporator to produce a wet solid. The solid was then placed in a freeze dryer (Virtis Freezemobile 35x1; Gardiner, N.Y.) for 72 hr to reduce the water content to approximately 1.5 wt % (1387 g crude material). The theoretical mass of total solids was 1351 g. The mass balance was very close to ideal and the isolated solid had slightly higher mass due to moisture. This added freeze drying step had the advantage of producing a free-flowing white powder whereas treatment in a vacuum oven resulted in a soapy solid cake that was very difficult to remove and had to be chipped and broken out of the flask.

The crude TFES-K can be further purified and isolated by extraction with reagent grade acetone, filtration, and drying.

$^{19}$F NMR (D$_2$O) δ. −122.0 (dt, J$_{FH}$=6 Hz, J$_{FF}$=6 Hz, 2F); −136.1 (dt, J$_{FH}$=53 Hz, 2F).

$^1$H NMR (D$_2$O) δ. 6.4 (tt, J$_{FH}$=53 Hz, J$_{FH}$=6 Hz, 1H).

% Water by Karl-Fisher titration: 580 ppm.

Analytical calculation for C$_2$HO$_3$F$_4$SK: C, 10.9: H, 0.5: N, 0.0 Experimental results: C, 11.1: H, 0.7: N, 0.2.

Mp (DSC): 242 degrees C.

TGA (air): 10% wt. loss @ (367 degrees C., 50% wt. loss @ 375 degrees C.

TGA (N$_2$): 10% wt. loss @ (363 degrees C., 50% wt. loss @ 375 degrees C.

(B) Synthesis of potassium-1,1,2-trifluoro-2-(perfluoroethoxy)ethanesulfonate (TPES-K)

A 1-gallon Hastelloy® C276 reaction vessel was charged with a solution of potassium sulfite hydrate (88 g, 0.56 mol), potassium metabisulfite (340 g, 1.53 mol) and deionized water (2000 ml). The vessel was cooled to 7 degrees C., evacuated to 0.05 MPa, and purged with nitrogen. The evacuate/purge cycle was repeated two more times. To the vessel was then added perfluoro(ethylvinyl ether) (PEVE, 600 g, 2.78 mol), and it was heated to 125 degrees C. at which time the inside pressure was 2.31 MPa. The reaction temperature was maintained at 125 degrees C. for 10 hr. The pressure dropped to 0.26 MPa at which point the vessel was vented and cooled to 25 degrees C. The crude reaction product was a white crystalline precipitate with a colorless aqueous layer (pH=7) above it.

The $^{19}$F NMR spectrum of the white solid showed pure desired product, while the spectrum of the aqueous layer showed a small but detectable amount of a fluorinated impurity. The desired isomer is less soluble in water so it precipitated in isomerically pure form.

The product slurry was suction filtered through a fritted glass funnel, and the wet cake was dried in a vacuum oven (60 degrees C., 0.01 MPa) for 48 hr. The product was obtained as off-white crystals (904 g, 97% yield).

$^{19}$F NMR (D$_2$O) δ −86.5 (s, 3F); −89.2, −91.3 (subsplit ABq, J$_{FF}$=147 Hz, 2F); −119.3, −121.2 (subsplit ABq, J$_{FF}$=258 Hz, 2F); −144.3 (dm, J$_{FH}$=53 Hz, 1F).

$^1$H NMR (D$_2$O) δ 6.7 (dm, J$_{FH}$=53 Hz, 1H).

Mp (DSC) 263 degrees C.

Analytical calculation for C$_4$HO$_4$F$_8$SK: C, 14.3: H, 0.3 Experimental results: C, 14.1: H, 0.3.

TGA (air): 10% wt. loss @ 359 degrees C., 50% wt. loss @ 367 degrees C.

TGA (N$_2$): 10% wt. loss @ 362 degrees C., 50% wt. loss @ 374 degrees C.

(C) Synthesis of potassium-1,1,2-trifluoro-2-(trifluoromethoxy)ethanesulfonate (TTES-K)

A 1-gallon Hastelloy® C276 reaction vessel was charged with a solution of potassium sulfite hydrate (114 g, 0.72 mol), potassium metabisulfite (440 g, 1.98 mol) and deionized water (2000 ml). The pH of this solution was 5.8. The vessel was cooled to −35 degrees C., evacuated to 0.08 MPa, and purged with nitrogen. The evacuate/purge cycle was repeated two more times. To the vessel was then added perfluoro (methylvinyl ether) (PMVE, 600 g, 3.61 mol) and it was heated to 125 degrees C. at which time the inside pressure was 3.29 MPa. The reaction temperature was maintained at 125 degrees C. for 6 hr. The pressure dropped to 0.27 MPa at which point the vessel was vented and cooled to 25 degrees C. Once cooled, a white crystalline precipitate of the desired product formed leaving a colorless clear aqueous solution above it (pH=7).

The $^{19}$F NMR spectrum of the white solid showed pure desired product, while the spectrum of the aqueous layer showed a small but detectable amount of a fluorinated impurity.

The solution was suction filtered through a fritted glass funnel for 6 hr to remove most of the water. The wet cake was then dried in a vacuum oven at 0.01 MPa and 50 degrees C. for 48 h. This gave 854 g (83% yield) of a white powder. The final product was isomerically pure (by $^{19}$F and $^1$H NMR) since the undesired isomer remained in the water during filtration.

$^{19}$F NMR (D$_2$O) δ. −59.9 (d, J$_{FH}$=4 Hz, 3F); −119.6, −120.2 (subsplit ABq, J=260 Hz, 2F); −144.9 (dm, J$_{FH}$=53 Hz, 1F).

$^1$H NMR (D$_2$O) δ. 6.6 (dm, J$_{FH}$=53 Hz, 1H).

% Water by Karl-Fisher titration: 71 ppm.

Analytical calculation for $C_3HF_6SO_4K$: C, 12.6: H, 0.4: N, 0.0 Experimental results: C, 12.6: H, 0.0: N, 0.1.

Mp (DSC) 257 degrees C.

TGA (air): 10% wt. loss @ 343 degrees C., 50% wt. loss @ 358 degrees C.

TGA ($N_2$): 10% wt. loss @ 341 degrees C., 50% wt. loss @ 357 degrees C.

(D) Synthesis of sodium 1,1,2,3,3,3-hexafluoropropanesulfonate (HFPS-Na)

A 1-gallon Hastelloy® C reaction vessel was charged with a solution of anhydrous sodium sulfite (25 g, 0.20 mol), sodium bisulfite 73 g, (0.70 mol) and of deionized water (400 ml). The pH of this solution was 5.7. The vessel was cooled to 4 degrees C., evacuated to 0.08 MPa, and then charged with hexafluoropropene (HFP, 120 g, 0.8 mol, 0.43 MPa). The vessel was heated with agitation to 120 degrees C. and kept there for 3 hr. The pressure rose to a maximum of 1.83 MPa and then dropped down to 0.27 MPa within 30 minutes. At the end, the vessel was cooled and the remaining HFP was vented, and the reactor was purged with nitrogen. The final solution had a pH of 7.3.

The water was removed in vacuo on a rotary evaporator to produce a wet solid. The solid was then placed in a vacuum oven (0.02 MPa, 140 degrees C., 48 hr) to produce 219 g of white solid, which contained approximately 1 wt % water. The theoretical mass of total solids was 217 g.

The crude HFPS-Na can be further purified and isolated by extraction with reagent grade acetone, filtration, and drying.

$^{19}$F NMR ($D_2O$) δ. −74.5 (m, 3F); −113.1, −120.4 (ABq, J=264 Hz, 2F); −211.6 (dm, 1F).

$^1$H NMR ($D_2O$) δ. 5.8 (dm, $J_{FH}$=43 Hz, 1H).

Mp (DSC) 126 degrees C.

TGA (air): 10% wt. loss @ 326 degrees C., 50% wt. loss @ 446 degrees C.

TGA ($N_2$): 10% wt. loss @ 322 degrees C., 50% wt. loss @ 449 degrees C.

Preparation of Ionic Liquids

E) Synthesis of 1-butyl-2,3-dimethylimidazolium 1,1,2,2-tetrafluoroethanesulfonate 1-Butyl-2,3-dimethylimidazolium chloride (22.8 g, 0.121 moles) was mixed with reagent-grade acetone (250 ml) in a large round-bottomed flask and stirred vigorously. Potassium 1,1,2,2-tetrafluoroethanesulfonate (TFES-K, 26.6 g, 0.121 moles), was added to reagent grade acetone (250 ml) in a separate round-bottomed flask, and this solution was carefully added to the 1-butyl-2,3-dimethylimidazolium chloride solution. The large flask was lowered into an oil bath and heated at 60 degrees C. under reflux for 10 hours. The reaction mixture was then filtered using a large frit glass funnel to remove the white KCl precipitate formed, and the filtrate was placed on a rotary evaporator for 4 hours to remove the acetone.

The reaction scheme is shown below:

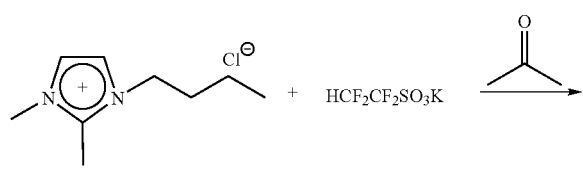

-continued

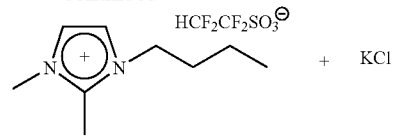

F) Synthesis of 1-butyl-methylimidazolium 1,1,2,2-tetrafluoroethanesulfonate

1-Butyl-3-methylimidazolium chloride (60.0 g) and high purity dry acetone (>99.5%, Aldrich, 300 ml) were combined in a 1 l flask and warmed to reflux with magnetic stirring until the solid completely dissolved. At room temperature in a separate 1 l flask, potassium-1,1,2,2-tetrafluoroethanesulfonte (TFES-K, 75.6 g) was dissolved in high purity dry acetone (500 ml). These two solutions were combined at room temperature and allowed to stir magnetically for 2 hr under positive nitrogen pressure. The stirring was stopped and the KCl precipitate was allowed to settle, then removed by suction filtration through a fritted glass funnel with a celite pad. The acetone was removed in vacuo to give a yellow oil. The oil was further purified by diluting with high purity acetone (100 ml) and stirring with decolorizing carbon (5 g). The mixture was again suction filtered and the acetone removed in vacuo to give a colorless oil. This was further dried at 4 Pa and 25 degrees C. for 6 hr to provide 83.6 g of product.

$^{19}$F NMR (DMSO-$d_6$) δ. −124.7 (dt, J=6 Hz, J=8 Hz, 2F); −136.8 (dt, J=53 Hz, 2F).

$^1$H NMR (DMSO-$d_6$) δ 0.9 (t, J=7.4 Hz, 3H); 1.3 (m, 2H); 1.8 (m, 2H); 3.9 (s, 3H); 4.2 (t, J=7 Hz, 2H); 6.3 (dt, J=53 Hz, J=6 Hz, 1H); 7.4 (s, 1H); 7.5 (s, 1H); 8.7 (s, 1H).

% Water by Karl-Fisher titration: 0.14%.

Analytical calculation for $C_9H_{12}F_6N_2O_3S$: C, 37.6: H, 4.7: N, 8.8. Experimental Results: C, 37.6: H, 4.6: N, 8.7.

TGA (air): 10% wt. loss @ 380 degrees C., 50% wt. loss @ 420 degrees C.

TGA ($N_2$): 10% wt. loss @ 375 degrees C., 50% wt. loss @ 422 degrees C.

G) Synthesis of 1-ethyl-3-methylimidazolium 1,1,2,2-tetrafluoroethane sulfonate

To a 500 ml round bottom flask was added 1-ethyl-3methylimidazolium chloride (Emim-Cl, 98%, 61.0 g) and reagent grade acetone (500 ml). The mixture was gently warmed (50 degrees C.) until almost all of the Emim-Cl dissolved. To a separate 500 ml flask was added potassium 1,1,2,2-tetrafluoroethanesulfonate (TFES-K, 90.2 g) along with reagent grade acetone (350 ml). This second mixture was stirred magnetically at 24 degrees C. until all of the TFES-K dissolved.

These solutions were combined in a 1 l flask producing a milky white suspension. The mixture was stirred at 24 degrees C. for 24 hrs. The KCl precipitate was then allowed to settle leaving a clear green solution above it.

The reaction mixture was filtered once through a celite/ acetone pad and again through a fitted glass funnel to remove the KCl. The acetone was removed in vacuo first on a rotovap and then on a high vacuum line (4 Pa, 25 degrees C.) for 2 hr. The product was a viscous light yellow oil (76.0 g, 64% yield).

The reaction scheme is shown below:

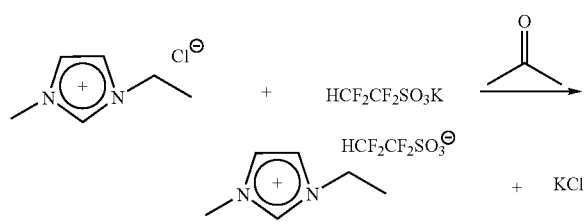

$^{19}$F NMR (DMSO-d$_6$) δ. −124.7 (dt, J$_{FH}$=6 Hz, J$_{FF}$=6 Hz, 2F); −138.4 (dt, J$_{FH}$=53 Hz, 2F).

$^1$H NMR (DMSO-d$_6$) δ. 1.3 (t, J=7.3 Hz, 3H); 3.7 (s, 3H); 4.0 (q, J=7.3 Hz, 2H);

6.1 (tt, J$_{FH}$=53 Hz, J$_{FH}$=6 Hz, 1H); 7.2 (s, 1H); 7.3 (s, 1H); 8.5 (s, 1H).

% Water by Karl-Fisher titration: 0.18%.

Analytical calculation for C$_8$H$_{12}$N$_2$O$_3$F$_4$S: C, 32.9: H, 4.1: N, 9.6 Found: C, 33.3: H, 3.7: N, 9.6.

Mp 45-46 degrees C.

TGA (air): 10% wt. loss @ 379 degrees C., 50% wt. loss @ 420 degrees C.

TGA (N$_2$): 10% wt. loss @ 378 degrees C., 50% wt. loss @ 418 degrees C.

H) Synthesis of 1-ethyl-3-methylimidazolium 1,1,2,3,3,3-hexafluoropropanesulfonate To a 1 l round bottom flask was added 1-ethyl-3-methylimidazolium chloride (Emim-Cl, 98%, 50.5 g) and reagent grade acetone (400 ml). The mixture was gently warmed (50 degrees C.) until almost all of the Emim-Cl dissolved. To a separate 500 ml flask was added potassium 1,1,2,3,3,3-hexafluoropropanesulfonate (HFPS-K, 92.2 g) along with reagent grade acetone (300 ml). This second mixture was stirred magnetically at room temperature until all of the HFPS-K dissolved.

These solutions were combined and stirred under positive N$_2$ pressure at 26 degrees C. for 12 hr producing a milky white suspension. The KCl precipitate was allowed to settle overnight leaving a clear yellow solution above it.

The reaction mixture was filtered once through a celite/acetone pad and again through a fritted glass funnel. The acetone was removed in vacuo first on a rotovap and then on a high vacuum line (4 Pa, 25 degrees C.) for 2 hr. The product was a viscous light yellow oil (103.8 g, 89% yield).

The reaction scheme is shown below:

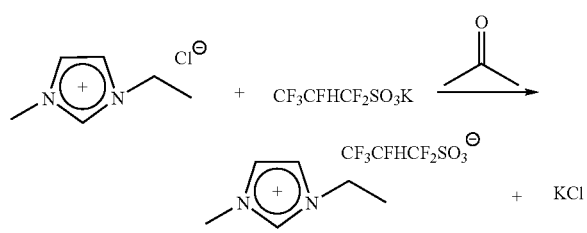

$^{19}$F NMR (DMSO-d$_6$) δ −73.8 (s, 3F); −114.5, −121.0 (ABq, J=258 Hz, 2F); −210.6 (m, 1F, J$_{HF}$=41.5 Hz).

$^1$H NMR (DMSO-d$_6$) δ. 1.4 (t, J=7.3 Hz, 3H); 3.9 (s, 3H); 4.2 (q, J=7.3 Hz, 2H,);

5.8 (m, J$_{HF}$=41.5 Hz, 1H,); 7.7 (s, 1H); 7.8 (s, 1H); 9.1 (s, 1H).

% Water by Karl-Fisher titration: 0.12%.

Analytical calculation for C$_9$H$_{12}$N$_2$O$_3$F$_6$S: C, 31.5: H, 3.5: N, 8.2. Experimental Results: C, 30.9: H, 3.3: N, 7.8.

TGA (air): 10% wt. loss @ 342 degrees C., 50% wt. loss @ 373 degrees C.

TGA (N$_2$): 10% wt. loss @ 341 degrees C., 50% wt. loss @ 374 degrees C.

I) Synthesis of 1-hexyl-3-methylimidazolium 1,1,2,2-tetrafluoroethanesulfonate

1-Hexyl-3-methylimidazolium chloride (10 g, 0.0493 moles) was mixed with reagent-grade acetone (100 ml) in a large round-bottomed flask and stirred vigorously under a nitrogen blanket. Potassium 1,1,2,2-tetrafluoroethane sulfonate (TFES-K, 10 g, 0.0455 moles) was added to reagent grade acetone (100 ml) in a separate round-bottomed flask, and this solution was carefully added to the 1-hexyl-3-methylimidazolium chloride/acetone mixture. The mixture was left to stir overnight. The reaction mixture was then filtered using a large frit glass funnel to remove the white KCl precipitate formed, and the filtrate was placed on a rotary evaporator for 4 hours to remove the acetone.

The reaction scheme is shown below:

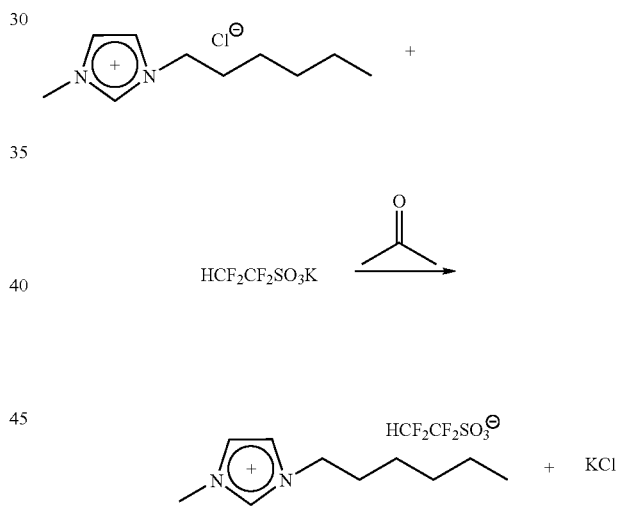

J) Synthesis of 1-dodecyl-3-methylimidazolium 1,1,2,2-tetrafluoroethanesulfonate 1-Dodecyl-3-methylimidazolium chloride (34.16 g, 0.119 moles) was partially dissolved in reagent-grade acetone (400 ml) in a large round-bottomed flask and stirred vigorously. Potassium 1,1,2,2-tetrafluoroethanesulfonate (TFES-K, 26.24 g, 0.119 moles) was added to reagent grade acetone (400 ml) in a separate round-bottomed flask, and this solution was carefully added to the 1-dodecyl-3-methylimidazolium chloride solution. The reaction mixture was heated at 60 degrees C. under reflux for approximately 16 hours. The reaction mixture was then filtered using a large frit glass funnel to remove the white KCl precipitate formed, and the filtrate was placed on a rotary evaporator for 4 hours to remove the acetone.

The reaction scheme is shown below:

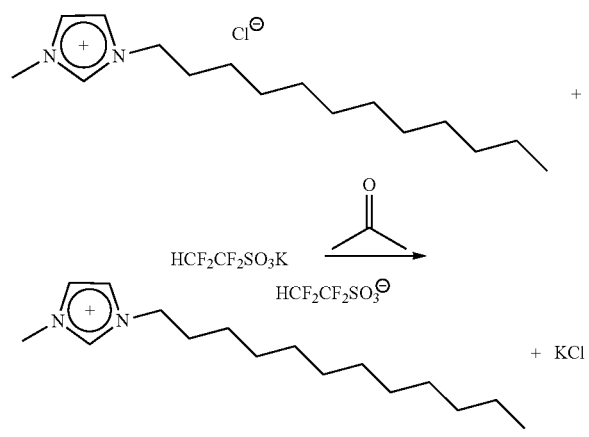

K) Synthesis of 1-hexadecyl-3-methylimidazolium 1,1,2,2-tetrafluoroethanesulfonate 1-Hexadecyl-3-methylimidazolium chloride (17.0 g, 0.0496 moles) was partially dissolved in reagent-grade acetone (100 ml) in a large round-bottomed flask and stirred vigorously. Potassium 1,1,2,2-tetrafluoroethanesulfonate (TFES-K, 10.9 g, 0.0495 moles) was added to reagent grade acetone (100 ml) in a separate round-bottomed flask, and this solution was carefully added to the 1-hexadecyl-3-methylimidazolium chloride solution. The reaction mixture was heated at 60 degrees C. under reflux for approximately 16 hours. The reaction mixture was then filtered using a large frit glass funnel to remove the white KCl precipitate formed, and the filtrate was placed on a rotary evaporator for 4 hours to remove the acetone.

The reaction scheme is shown below:

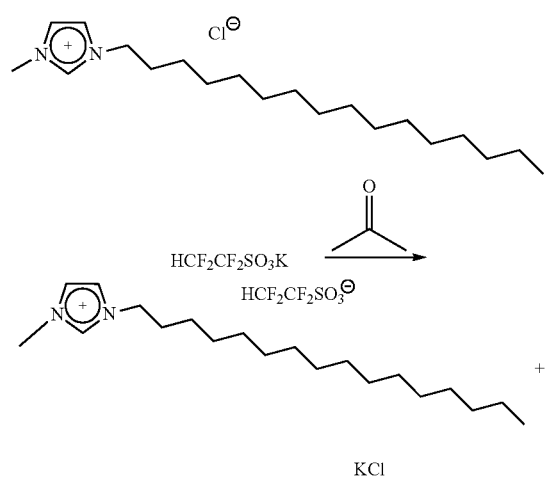

L) Synthesis of 1-octadecyl-3-methylimidazolium 1,1,2,2-tetrafluoroethaneulfonate 1-Octadecyl-3-methylimidazolium chloride (17.0 g, 0.0458 moles) was partially dissolved in reagent-grade acetone (200 ml) in a large round-bottomed flask and stirred vigorously. Potassium 1,1,2,2-tetrafluoroethanesulfonate (TFES-K, 10.1 g, 0.0459 moles), was added to reagent grade acetone (200 ml) in a separate round-bottomed flask, and this solution was carefully added to the 1-octadecyl-3-methylimidazolium chloride solution. The reaction mixture was heated at 60 degrees C. under reflux for approximately 16 hours. The reaction mixture was then filtered using a large frit glass funnel to remove the white KCl precipitate formed, and the filtrate was placed on a rotary evaporator for 4 hours to remove the acetone.

The reaction scheme is shown below:

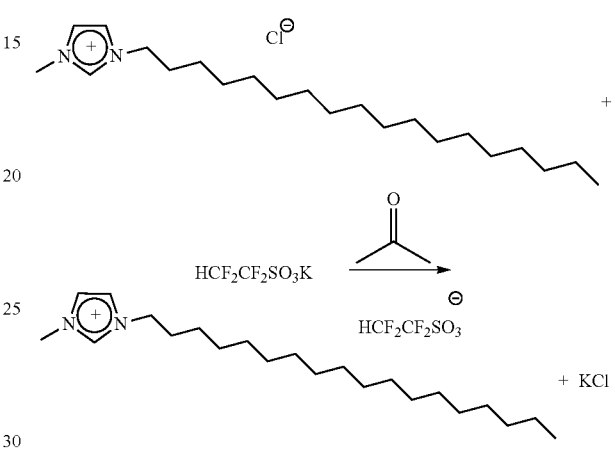

M) Synthesis of 1-propyl-3-(1,1,2,2-TFES) imidazolium 1,1,2,2-tetrafluoroethanesulfonate Imidazole (19.2 g) was added to of tetrahydrofuran (80 mls). A glass shaker tube reaction vessel was filled with the THF-containing imidazole solution. The vessel was cooled to 18° C., evacuated to 0.08 MPa, and purged with nitrogen. The evacuate/purge cycle was repeated two more times. Tetrafluoroethylene (TFE, 5 g) was then added to the vessel, and it was heated to 100 degrees C., at which time the inside pressure was about 0.72 MPa. As the TFE pressure decreased due to the reaction, more TFE was added in small aliquots (5 g each) to maintain operating pressure roughly between 0.34 MPa and 0.86 MPa. Once 40 g of TFE had been fed, the vessel was vented and cooled to 25 degrees C. The THF was then removed under vacuum and the product was vacuum distilled at 40 degrees C. to yield pure product as shown by $^1$H and $^{19}$F NMR (yield 44 g). Iodopropane (16.99 g) was mixed with 1-(1,1,2,2-tetrafluoroethyl)imidazole (16.8 g) in dry acetonitrile (100 ml), and the mixture was refluxed for 3 days. The solvent was removed in vacuo, yielding a yellow waxy solid (yield 29 g). The product, 1-propyl-3-(1,1,2,2-tetrafluoroethyl)imidazolium iodide was confirmed by 1H NMR (in $CD_3CN$) [0.96 (t, 3H); 1.99 (m, 2H); 4.27 (t, 2H); 6.75 (t, 1H); 7.72 (d, 2H); 9.95 (s, 1H)].

Iodide (24 g) was then added to 60 ml of dry acetone, followed by 15.4 g of potassium 1,1,2,2-tetrafluoroethanesulfonate in 75 ml of dry acetone. The mixture was heated at 60 degrees C. overnight and a dense white precipitate was formed (potassium iodide). The mixture was cooled, filtered, and the solvent from the filtrate was removed using a rotary evaporator. Some further potassium iodide was removed under filtration. The product was further purified by adding 50 g of acetone, 1 g of charcoal, 1 g of celite and 1 g of silica gel. The mixture was stirred for 2 hours, filtered and the solvent removed. This yielded 15 g of a liquid, shown by NMR to be the desired product.

N) Synthesis of 1-butyl-3-methylimidazolium 1,1,2,3,3,3-hexafluoropropanesulfonate (Bmim-HFPS)

1-Butyl-3-methylimidazolium chloride (Bmim-Cl, 50.0 g) and high purity dry acetone (>99.5%, 500 ml) were combined in a 1 l flask and warmed to reflux with magnetic stirring until the solid all dissolved. At room temperature in a separate 1 l flask, potassium-1,1,2,3,3,3-hexafluoropropanesulfonte (HFPS-K) was dissolved in high purity dry acetone (550 ml). These two solutions were combined at room temperature and allowed to stir magnetically for 12 hr under positive nitrogen pressure. The stirring was stopped, and the KCl precipitate was allowed to settle. This solid was removed by suction filtration through a fritted glass funnel with a celite pad. The acetone was removed in vacuo to give a yellow oil. The oil was further purified by diluting with high purity acetone (100 ml) and stirring with decolorizing carbon (5 g). The mixture was suction filtered and the acetone removed in vacuo to give a colorless oil. This was further dried at 4 Pa and 25 degrees C. for 2 hr to provide 68.6 g of product.

$^{19}$F NMR (DMSO-d$_6$) δ −73.8 (s, 3F); −114.5, −121.0 (ABq, J=258 Hz, 2F); −210.6 (m, J=42 Hz, 1F).

$^{1}$H NMR (DMSO-d$_6$) δ 0.9 (t, J=7.4 Hz, 3H); 1.3 (m, 2H); 1.8 (m, 2H); 3.9 (s, 3H); 4.2 (t, J=7 Hz, 2H); 5.8 (dm, J=42 Hz, 1H); 7.7 (s, 1H); 7.8 (s, 1H); 9.1 (s, 1H).

% Water by Karl-Fisher titration: 0.12%.

Analytical calculation for C$_9$H$_{12}$F$_6$N$_2$O$_3$S: C, 35.7: H, 4.4: N, 7.6. Experimental Results: C, 34.7: H, 3.8: N, 7.2.

TGA (air): 10% wt. loss @ 340 degrees C., 50% wt. loss @ 367 degrees C.

TGA (N$_2$): 10% wt. loss @ 335 degrees C., 50% wt. loss @ 361 degrees C.

Extractable chloride by ion chromatography: 27 ppm.

O) Synthesis of 1-butyl-3-methylimidazolium 1,1,2-trifluoro-2-(trifluoromethoxy)ethanesulfonate (Bmim-TTES)

1-Butyl-3-methylimidazolium chloride (Bmim-Cl, 10.0 g) and deionized water (15 ml) were combined at room temperature in a 200 ml flask. At room temperature in a separate 200 ml flask, potassium 1,1,2-trifluoro-2-(trifluoromethoxy)ethanesulfonate (TTES-K, 16.4 g) was dissolved in deionized water (90 ml). These two solutions were combined at room temperature and allowed to stir magnetically for 30 min. under positive nitrogen pressure to give a biphasic mixture with the desired ionic liquid as the bottom phase. The layers were separated, and the aqueous phase was extracted with 2×50 ml portions of methylene chloride. The combined organic layers were dried over magnesium sulfate and concentrated in vacuo. The colorless oil product was dried at for 4 hr at 5 Pa and 25 degrees C. to afford 15.0 g of product.

$^{19}$F NMR (DMSO-d$_6$) δ −56.8 (d, J$_{FH}$=4 Hz, 3F); −119.5, −119.9 (subsplit ABq, J=260 Hz, 2F); −142.2 (dm, J$_{FH}$=53 Hz, 1F).

$^{1}$H NMR (DMSO-d$_6$) δ 0.9 (t, J=7.4 Hz, 3H); 1.3 (m, 2H); 1.8 (m, 2H); 3.9 (s, 3H); 4.2 (t, J=7.0 Hz, 2H); 6.5 (dt, J=53 Hz, J=7 Hz, 1H); 7.7 (s, 1H); 7.8 (s, 1H); 9.1 (s, 1H).

% Water by Karl-Fisher titration: 613 ppm.

Analytical calculation for C11H16F6N2O4S: C, 34.2: H, 4.2: N, 7.3.

Experimental Results: C, 34.0: H, 4.0: N, 7.1.

TGA (air): 10% wt. loss @ 328 degrees C., 50% wt. loss @ 354 degrees C.

TGA (N$_2$): 10% wt. loss @ 324 degrees C., 50% wt. loss @ 351 degrees C.

Extractable chloride by ion chromatography: <2 ppm.

P) Synthesis of 1-butyl-3-methylimidazolium 1,1,2-trifluoro-2-(perfluoroethoxy)ethanesulfonate (Bmim-TPES)

1-Butyl-3-methylimidazolium chloride (Bmim-Cl, 7.8 g) and dry acetone (150 ml) were combined at room temperature in a 500 ml flask. At room temperature in a separate 200 ml flask, potassium 1,1,2-trifluoro-2-(perfluoroethoxy)ethanesulfonate (TPES-K, 15.0 g) was dissolved in dry acetone (300 ml). These two solutions were combined and allowed to stir magnetically for 12 hr under positive nitrogen pressure. The KCl precipitate was then allowed to settle leaving a colorless solution above it. The reaction mixture was filtered once through a celite/acetone pad and again through a fitted glass funnel to remove the KCl. The acetone was removed in vacuo first on a rotovap and then on a high vacuum line (4 Pa, 25 degrees C.) for 2 hr. Residual KCl was still precipitating out of the solution, so methylene chloride (50 ml) was added to the crude product, which was then washed with deionized water (2×50 ml). The solution was dried over magnesium sulfate, and the solvent was removed in vacuo to give the product as a viscous light yellow oil (12.0 g, 62% yield).

$^{19}$F NMR (CD$_3$CN) δ −85.8 (s, 3F); −87.9, −90.1 (subsplit ABq, J$_{FF}$=147 Hz, 2F); −120.6, −122.4 (subsplit ABq, J$_{FF}$=258 Hz, 2F); −142.2 (dm, J$_{FH}$=53 Hz, 1F).

$^{1}$H NMR (CD$_3$CN) δ 1.0 (t, J=7.4 Hz, 3H); 1.4 (m, 2H); 1.8 (m, 2H); 3.9 (s, 3H); 4.2 (t, J=7.0 Hz, 2H); 6.5 (dm, J=53 Hz, 1H); 7.4 (s, 1H); 7.5 (s, 1H); 8.6 (s, 1H).

% Water by Karl-Fisher titration: 0.461.

Analytical calculation for C12H16F8N2O4S: C, 33.0: H, 3.7. Experimental

Results: C, 32.0: H, 3.6.

TGA (air): 10% wt. loss @ 334 degrees C., 50% wt. loss @ 353 degrees C.

TGA (N$_2$): 10% wt. loss @ 330 degrees C., 50% wt. loss @ 365 degrees C.

Q) Synthesis of tetradecyl(tri-n-butyl)phosphonium 1,1,2,3,3,3-hexafluoropropanesulfonate ([4.4.4.14]P-HFPS)

To a 4 l round bottomed flask was added the ionic liquid tetradecyl(tri-n-butyl)phosphonium chloride (Cyphos® IL 167, 345 g) and deionized water (1000 ml). The mixture was magnetically stirred until it was one phase. In a separate 2 l flask, potassium 1,1,2,3,3,3-hexafluoropropanesulfonate (HFPS-K, 214.2 g) was dissolved in deionized water (1100 ml). These solutions were combined and stirred under positive N$_2$ pressure at 26 degrees C. for 1 hr producing a milky white oil. The oil slowly solidified (439 g) and was removed by suction filtration and then dissolved in chloroform (300 ml). The remaining aqueous layer (pH=2) was extracted once with chloroform (100 ml). The chloroform layers were combined and washed with an aqueous sodium carbonate solution (50 ml) to remove any acidic impurity. They were then dried over magnesium sulfate, suction filtered, and reduced in vacuo first on a rotovap and then on a high vacuum line (4 Pa, 100 degrees C.) for 16 hr to yield the final product as a white solid (380 g, 76% yield).

$^{19}$F NMR (DMSO-d$_6$) δ −73.7 (s, 3F); −114.6, −120.9 (ABq, J=258 Hz, 2F); −210.5 (m, J$_{HF}$=41.5 Hz, 1F).

$^1$H NMR (DMSO-d$_6$) δ 0.8 (t, J=7.0 Hz, 3H); 0.9 (t, J=7.0 Hz, 9H); 1.3 (br s, 20H); 1.4 (m, 16H); 2.2 (m, 8H); 5.9 (m, J$_{HF}$=42 Hz, 1H).

% Water by Karl-Fisher titration: 895 ppm.

Analytical calculation for C29H57F6O3PS: C, 55.2: H, 9.1: N, 0.0.

Experimental Results: C, 55.1: H, 8.8: N, 0.0.

TGA (air): 10% wt. loss @ 373 degrees C., 50% wt. loss @ 421 degrees C.

TGA (N$_2$): 10% wt. loss @ 383 degrees C., 50% wt. loss @ 436 degrees C.

R) Synthesis of Tetradecyl(tri-n-hexyl)phosphonium 1,1,2-trifluoro-2-(perfluoroethoxy)ethanesulfonate ([6.6.6.14]P-TPES)

To a 500 ml round bottomed flask was added acetone (Spectroscopic grade, 50 ml) and ionic liquid tetradecyl(tri-n-hexyl)phosphonium chloride (Cyphos® IL 101, 33.7 g). The mixture was magnetically stirred until it was one phase. In a separate 1 l flask, potassium 1,1,2-trifluoro-2-(perfluoroethoxy)ethanesulfonate (TPES-K, 21.6 g) was dissolved in acetone (400 ml). These solutions were combined and stirred under positive N$_2$ pressure at 26 degrees C. for 12 hr producing a white precipitate of KCl. The precipitate was removed by suction filtration, and the acetone was removed in vacuo on a rotovap to produce the crude product as a cloudy oil (48 g). Chloroform (100 ml) was added, and the solution was washed once with deionized water (50 ml). It was then dried over magnesium sulfate and reduced in vacuo first on a rotovap and then on a high vacuum line (8 Pa, 24 degrees C.) for 8 hr to yield the final product as a slightly yellow oil (28 g, 56% yield).

$^{19}$F NMR (DMSO-d$_6$) δ −86.1 (s, 3F); −88.4, −90.3 (subsplit ABq, J$_{FF}$=147 Hz, 2F); −121.4, −122.4 (subsplit ABq, J$_{FF}$=258 Hz, 2F); −143.0 (dm, J$_{FH}$=53 Hz, 1F).

$^1$H NMR (DMSO-d$_6$) δ 0.9 (m, 12H); 1.2 (m, 16H); 1.3 (m, 16H); 1.4 (m, 8H);

1.5 (m, 8H); 2.2 (m, 8H); 6.3 (dm, J$_{FH}$=54 Hz, 1H).

% Water by Karl-Fisher titration: 0.11.

Analytical calculation for C36H69F8O4PS: C, 55.4: H, 8.9: N, 0.0.

Experimental Results: C, 55.2: H, 8.2: N, 0.1.

TGA (air): 10% wt. loss @ 311 degrees C., 50% wt. loss @ 339 degrees C.

TGA (N$_2$): 10% wt. loss @ 315 degrees C., 50% wt. loss @ 343 degrees C.

S) Synthesis of tetradecyl(tri-n-hexyl)phosphonium 1,1,2-trifluoro-2-(trifluoromethoxy)ethanesulfonate ([6.6.6.14]P-TTES)

To a 100 ml round bottomed flask was added acetone (Spectroscopic grade, 50 ml) and ionic liquid tetradecyl(tri-n-hexyl)phosphonium chloride (Cyphos® IL 101, 20.2 g). The mixture was magnetically stirred until it was one phase. In a separate 100 ml flask, potassium 1,1,2-trifluoro-2-(trifluoromethoxy)ethanesulfonate (TTES-K, 11.2 g) was dissolved in acetone (100 ml). These solutions were combined and stirred under positive N$_2$ pressure at 26 degrees C. for 12 hr producing a white precipitate of KCl.

The precipitate was removed by suction filtration, and the acetone was removed in vacuo on a rotovap to produce the crude product as a cloudy oil. The product was diluted with ethyl ether (100 ml) and then washed once with deionized water (50 ml), twice with an aqueous sodium carbonate solution (50 ml) to remove any acidic impurity, and twice more with deionized water (50 ml). The ether solution was then dried over magnesium sulfate and reduced in vacuo first on a rotovap and then on a high vacuum line (4 Pa, 24 degrees C.) for 8 hr to yield the final product as an oil (19.0 g, 69% yield).

$^{19}$F NMR (CD$_2$Cl$_2$) δ −60.2 (d, J$_{FH}$=4 Hz, 3F); −120.8, −125.1 (subsplit ABq, J=260 Hz, 2F); −143.7 (dm, J$_{FH}$=53 Hz, 1F).

$^1$H NMR (CD$_2$Cl$_2$) δ 0.9 (m, 12H); 1.2 (m, 16H); 1.3 (m, 16H); 1.4 (m, 8H); 1.5 (m, 8H); 2.2 (m, 8H); 6.3 (dm, J$_{FH}$=54 Hz, 1H).

% Water by Karl-Fisher titration: 412 ppm.

Analytical calculation for C35H69F6O4PS: C, 57.5: H, 9.5: N, 0.0.

Experimental results: C, 57.8: H, 9.3: N, 0.0.

TGA (air): 10% wt. loss @ 331 degrees C., 50% wt. loss @ 359 degrees C.

TGA (N$_2$): 10% wt. loss @ 328 degrees C., 50% wt. loss @ 360 degrees C.

T) Synthesis of 1-ethyl-3-methylimidazolium 1,1,2, 2-tetrafluoro-2-(pentafluoroethoxy)sulfonate (Emim-TPENTAS)

To a 500 ml round bottomed flask was added 1-ethyl-3-methylimidazolium chloride (Emim-Cl, 98%, 18.0 g) and reagent grade acetone (150 ml). The mixture was gently warmed (50 degrees C.) until all of the Emim-Cl dissolved. In a separate 500 ml flask, potassium 1,1,2,2-tetrafluoro-2-(pentafluoroethoxy)sulfonate (TPENTAS-K, 43.7 g) was dissolved in reagent grade acetone (450 ml).

These solutions were combined in a 1 l flask producing a white precipitate (KCl). The mixture was stirred at 24 degrees C. for 8 hr. The KCl precipitate was then allowed to settle leaving a clear yellow solution above it. The KCl was removed by filtration through a celite/acetone pad. The acetone was removed in vacuo to give a yellow oil, which was then diluted with chloroform (100 ml). The chloroform was washed three times with deionized water (50 ml), dried over magnesium sulfate, filtered, and reduced in vacuo first on a rotovap and then on a high vacuum line (4 Pa, 25 degrees C.) for 8 hr. The product was a light yellow oil (22.5 g).

$^{19}$F NMR (DMSO-d$_6$) δ −82.9 (m, 2F); −87.3 (s, 3F); −89.0 (m, 2F); −118.9 (s, 2F).

$^1$H NMR (DMSO-d$_6$) δ 1.5 (t, J=7.3 Hz, 3H); 3.9 (s, 3H); 4.2 (q, J=7.3 Hz, 2H);

7.7 (s, 1H); 7.8 (s, 1H); 9.1 (s, 1H).

% Water by Karl-Fisher titration: 0.17%.

Analytical calculation for C10H11N2O4F9S: C, 28.2: H, 2.6: N, 6.6

Experimental results: C, 28.1: H, 2.9: N, 6.6.

TGA (air): 10% wt. loss @ 351 degrees C., 50% wt. loss @ 401 degrees C.

TGA (N$_2$): 10% wt. loss @ 349 degrees C., 50% wt. loss @ 406 degrees C.

U) Synthesis of tetrabutylphosphonium 1,1,2-trifluoro-2-(perfluoroethoxy)ethanesulfonate (TBP-TPES)

To a 200 ml round bottomed flask was added deionized water (100 ml) and tetra-n-butylphosphonium bromide (Cytec Canada Inc., 20.2 g). The mixture was magnetically stirred until the solid all dissolved. In a separate 300 ml flask, potassium 1,1,2-trifluoro-2-(perfluoroethoxy)ethanesulfonate (TPES-K, 20.0 g) was dissolved in deionized water (400 ml) heated to 70 degrees C. These solutions were combined and stirred under positive $N_2$ pressure at 26 degrees C. for 2 hr producing a lower oily layer. The product oil layer was separated and diluted with chloroform (30 ml), then washed once with an aqueous sodium carbonate solution (4 ml) to remove any acidic impurity, and three times with deionized water (20 ml). It was then dried over magnesium sulfate and reduced in vacuo first on a rotovap and then on a high vacuum line (8 Pa, 24 degrees C.) for 2 hr to yield the final product as a colorless oil (28.1 g, 85% yield).

$^{19}$F NMR ($CD_2Cl_2$) δ −86.4 (s, 3F); −89.0, −90.8 (subsplit ABq, $J_{FF}$=147 Hz, 2F); −119.2, −125.8 (subsplit ABq, $J_{FF}$=254 Hz, 2F); −141.7 (dm, $J_{FH}$=53 Hz, 1F).

$^1$H NMR ($CD_2Cl_2$) δ 1.0 (t, J=7.3 Hz, 12H); 1.5 (m, 16H); 2.2 (m, 8H); 6.3 (dm, $J_{FH}$=54 Hz, 1H).

% Water by Karl-Fisher titration: 0.29.

Analytical calculation for C20H37F8O4PS: C, 43.2: H, 6.7: N, 0.0.

Experimental results: C, 42.0: H, 6.9: N, 0.1.

Extractable bromide by ion chromatography: 21 ppm.

The gas solubility and diffusivity measurements were made using a gravimetric microbalance (Hiden Isochema Ltd, IGA 003, Warrington, UK). The IGA design integrates precise computer-control and measurement of weight change, pressure and temperature to enable fully automatic and reproducible determination of gas adsorption-desorption isotherms and isobars. The microbalance consists of an electrobalance with sample and counterweight components inside a stainless steel pressure-vessel as shown in FIG. 18 and described in Example 38, Table 31. The balance has a weigh range of 0-100 mg with a resolution of 0.1 μg. An enhanced pressure stainless steel (SS316LN) reactor capable of operation to 20.0 bar and 100° C. was installed. Approximately 60 mg of ionic liquid sample was added to the sample container and the reactor was sealed. The sample was dried and degassed by first pulling a course vacuum on the sample with a diaphragm pump (Pfeiffer, model MVP055-3, Asslar, Germany) and then fully evacuating the reactor to $10^{-8}$ bar with a turbopump (Pfeiffer, model TSH-071). While under deep vacuum, the sample was heated to 75° C. for 10 hr with an external water jacket connected to a remote-controlled constant-temperature bath (Huber Ministat, model cc-S3, Offenburg, Germany). A 30 percent ethylene glycol and 70 percent water mixture by volume was used as the recirculating fluid with a temperature range of 5 to 90° C. The sample mass slowly decreased as residual water and gases were removed. Once the mass had stabilized for at least 60 min, the sample dry mass was recorded. The percent weight loss for the various ionic liquids tested was in the range of 1 to 3%.

The IGA003 can operate in both dynamic and static mode. Dynamic mode operation provides a continuous flow of gas (max. 500 $cm^3$ $min^{-1}$) past the sample and the exhaust valve controls the set-point pressure. Static mode operation introduces gas into the top of the balance away from the sample and both the admittance and exhaust valves control the set-point pressure. All absorption measurements were performed in static mode. The sample temperature was measured with a type K thermocouple with an accuracy of ±0.1° C. The thermocouple was located inside the reactor next to the sample container. The water jacket maintained the set-point temperature automatically to within a typical regulation accuracy of ±0.1° C. Four isotherms (at 10, 25, 50, and 75° C.) were measured beginning with 10° C. Once the desired temperature was achieved and stable, the admittance and exhaust valves automatically opened and closed to adjust the pressure to the first set-point. Pressures from $10^{-9}$ to $10^{-1}$ bar were measured using a capacitance manometer (Pfeiffer, model PKR251), and pressures from $10^{-1}$ to 20.0 bar were measured using a piezo-resistive strain gauge (Druck, model PDCR4010, New Fairfield, Conn.). Regulation maintained the reactor pressure set-point to within ±4 to 8 mbar. The pressure ramp rate was set at 200 mbar $min^{-1}$ and the temperature ramp rate was set at 1° C. $min^{-1}$. The upper pressure limit of the stainless steel reactor was 20.0 bar, and several isobars up to 10 bar (i.e., 0.1, 0.5, 1, 4, 7, 10 bar) were measured. To ensure sufficient time for gas-liquid equilibrium, the ionic liquid samples were maintained at set-point for a minimum of 3 hr with a maximum time-out of 8 hr.

The IGA method exploits the relaxation behavior following pressure and temperature changes to simultaneously evaluate the time-dependent absorption and asymptotic uptake. The real-time processor was used to determine the end-point for each isotherm. The percent relaxation used as an end point for the real-time analysis was 99 percent. The minimum weight change for real-time analysis was set at 1 μg, the acceptable average deviation of the model from the acquired data was set at 7 μg, and the target interval for weight acquisition was set at a typical value of 1 μg. The temperature variation during an isotherm was maintained less than 0.1° C. $min^{-1}$.

Safety features of the IGA003 included a pressure relief valve and over-temperature control for the reactor. The factory-installed relief valve was replaced with a DuPont guideline relief valve (Circle-Seal, set-point pressure 24.5 bar; DuPont, Wilmington, Del.). To further protect the microbalance system from over-pressure, additional relief valves were installed on the custom gas manifold and on each gas cylinder; these relief valves were set to open if the pressure exceeded 25 bar. The reactor over-temperature interlock controller that comes standard on the IGA003 was set to turn off the water bath if the temperature exceeded 100° C. Due to the fact that some of the gases tested were flammable (i.e. HFC-32, HFC-143a, and HFC-152a), the IGA003 was mounted inside a custom stainless steel cabinet purged with nitrogen that would minimize the possibility of a flame.

Thermogravimetric measurements were corrected for a number of gravitational balance forces introduced at high pressure as described by Pinkerton, E. P., et al. (High-pressure gravimetric measurement of hydrogen capacity in vapor-grown carbon nanofibers and related materials. Proceedings of the 11$^{th}$ Canadian Hydrogen Conference, Victoria, BC (2001) pages 633-642). These included:

(1) Changes in the buoyant forces due to changes in pressure and temperature.
(2) Aerodynamic drag forces created by the flow of gases.
(3) Changes in the balance sensitivity due to changes in temperature and pressure.
(4) Volumetric changes in the samples due to expansivity.

The gravitational balance forces previously described are often of the same order of magnitude (0.1 to 5 mg) as the overall weight change in the sample and can lead to inaccurate results if not accounted for precisely. Distinguishing mass changes with an accuracy of 0.01 wt. % on small and sometimes limited sample quantities requires knowledge of the sample weight to within about 5 to 10 μg.

The buoyancy correction follows from Archimedes' principal: there is an upward force exerted on an object equivalent to the mass of fluid displaced. The upward force ($C_b$) due to buoyancy is calculated using eq 1 where the mass of the gas displaced is equivalent to the volume of the submersed object ($V_i$) times the density ($\rho_g$) of the gas at a given (T,P) and the gravitational acceleration (g). If the volume of the object remains constant, $V_i$ can be calculated by knowing the mass ($m_i$) and density ($\rho_i$) of the object.

$$C_b = \text{Buoyancy} = gV_i\rho_g(T, P) = g\frac{m_i}{\rho_i}\rho_g(T, P) \quad (1)$$

Instead of using the gas densities provided in the Hiden Isochema IGA software, the gas density for each gas was calculated using a computer program (REFPROP v.7) developed by the National Institute of Standards and Technology (NIST) (Lemmon E W, et al. [NIST reference fluid thermodynamic and transport properties—REFPROP, version 7.0 user's guide, U.S. Department of Commerce, Technology Administration, National Institute of Standards and Technology, Standard Reference Data Program, Gaithersburg, Md., 2002]).

The buoyancy correction using the IGA003 system involves many additional objects for weighing the sample. Table 31 provides a list of each critical component along with the objects weight, material, density, and temperature. The component arrangement in FIG. 18 leads to a mass balance as shown by eq 2. This expression accounts for the summation of all components as well as the contribution of the absorbed gas mass ($m_a$) and a correction factor ($C_f$) which accounts for the balance sensitivity to T, P. The density of air ($\rho_{air}$) at ambient temperature and pressure was subtracted from $\rho_i$ and $\rho_j$ because the components were initially weighed in air.

$$\sum_{i=1} m_i - \sum_{j=1} m_j - \sum_{i=1} \frac{m_i}{\rho_i}\rho_g(T_i, P) + \sum_{j=1} \frac{m_j}{\rho_j}\rho_g(T_j, P) + m_{IL} + m_a - \quad (2)$$

$$\frac{m_{IL}}{\rho_s(T_s)}\rho_g(T_s, P) - \frac{m_a}{\rho_a(T_s)}\rho_g(T_s, P) - C_f(T_s, P) = \text{reading}$$

The largest contributions in eq 2 are typically those of the sample container, sample, and counter weight; the other referenced objects in Table 31 contribute less because of their larger densities (denominators in eq 2). Physical densities of ionic liquids were measured using a Micromeritics Accupyc 1330 helium pycnometer with an accuracy of ±0.001 g cm$^{-3}$ (Micromeritics Instrument Corp., Norcross, Ga.). Initially, the volume ($V_{IL}$) of each sample was calculated from its pycnometric density ($\rho_s$) and dry mass sample weight ($\rho_s$), but volumetric expansion ($\Delta\tilde{V}/\tilde{V}_0$) due to the gas absorption was later taken into account as described below to more accurately determine the buoyancy effect.

The system was operated in static mode that essentially eliminates any aerodynamic drag forces due to flowing gases. Electrobalances are sensitive to temperature and pressure fluctuations on the beam arm and internal electronics. To minimize this effect, the balance electronics are heated externally with a band heater to a temperature of 45±0.1° C. In addition, the component temperatures provided in Table 31 are measured for the sample ($T_s$) and all others are estimated. Therefore, a correction factor ($C_f$) was determined as a function of T, P by measuring the buoyancy effect without a sample and calculating a least-squares fit to tare the balance. The correction factor was on the order of 0.1 to 0.3 mg and increased as expected with decreasing temperature and increasing pressure.

Initially the ionic liquid sample volume was considered to be constant and the mole fraction solubility calculated without taking into account buoyancy effects due to sample expansivity. In order to make a proper buoyancy correction due to the liquid volume change, a simple mole fraction average for the molar volume, $\tilde{V}_m$, was used.

$$\tilde{V}_m(T, P) = \tilde{V}_{IL}(1-x) + \tilde{V}_g x, \quad (3)$$

where $\tilde{V}_i = MW_i/\rho_i$ and x represents the molar fraction of gas in the solution.

$$V_m(T, P) = \tilde{V}_m(T, P)\left[\left(\frac{m_{IL}}{MW_{IL}}\right) + \left(\frac{m_g}{MW_g}\right)\right] \quad (4)$$

$$\frac{m_s}{\rho_s(T_s)}\rho_g(T_s, P) + \frac{m_a}{\rho_a(T_s)}\rho_g(T_s, P) = V_m(T, P)\rho_g(T, P) \quad (5)$$

As a first approximation, eqs 3 and 4 were used to estimate the change in the liquid sample volume, $V_m$, at the measured T, P conditions. Eq 5 can be substituted into eq 2 to account for the buoyancy change with respect to sample expansivity.

Besides the equilibrium solubility, time-dependent absorption data were also gathered using the Hiden gravimetric microbalance for each T, P set-point. In order to understand the time-dependent behavior of gas dissolving in liquid, we applied a mathematical model based on a simplified mass diffusion process. Imagine a flat-bottom sample container filled with ionic liquid at a certain liquid level height (L). The height is determined by knowing the cylindrical geometry of the sample container, dry sample weight after evacuation and heating, and the ionic liquid density at the proper temperature. After evacuation, the gas is introduced into the Pyrex® sample container with a constant pressure at a given temperature. A small amount of gas will start dissolving into the ionic liquid, and after a sufficient time it will reach a thermodynamic equilibrium, that is the solubility limit of the gas in the ionic liquid at the given T and P. This transient behavior with time is modeled as described by Shiflett, M. B. and Yokozeki, A. (*Ind. Eng. Chem. Research,* 2005, 44, 4453-4464) and Yokozeki, A. (*Int. J. Refrigeration,* 2002, 22, 695-704).

Processes of gas dissolving in liquid may be highly complex phenomena because of a possible evolution of heat of mixing, the subsequent liquid convection due to the local temperature difference, as well as the free convection due to the density difference, and the possible change in thermophysical properties of the liquid. The following assumptions were made for the dissolving gas (Shiflett, M. B., and Yokozeki, A. (supra); and Yokozeki, A (Time-dependent behavior of gas absorption in lubricant oil [*Int. J. Refrigeration* (2002), 22, 695-704]):

(1) Gas dissolves through a one-dimensional (vertical) diffusion process, in which there is no convective flow in the liquid.
(2) A thin boundary layer between the gas and liquid phases exists, where the thermodynamic equilibrium is instantly established with the saturation concentration ($C_S$), and where the concentration is constant all the time at a given temperature and pressure.
(3) Temperature and pressure are kept constant.
(4) The gas-dissolved liquid is a highly dilute solution, and so the relevant thermophysical properties of the solution do not change.

The process may then be described by one-dimensional mass diffusion due to the local concentration difference. The governing differential equations are:

$$\frac{\partial C}{\partial t} = D\frac{\partial^2 C}{\partial z^2} \quad (6)$$

Initial Condition: $C = C_0$ when $t = 0$ and $0 < z < L$ \quad (7)

Boundary Conditions: $C = C_S$ when $t > 0$ and $z = 0$ \quad (8)

-continued $$\frac{\partial C}{\partial z} = 0 \text{ at } z = L \quad (9)$$

where C is the concentration of a dissolving substance in ionic liquid as a function of time, t and vertical location, z, where L is the depth of ionic liquid in the container, and z=0 corresponds to the vapor-liquid boundary. $C_o$ is an initial homogenous concentration of the dissolving gas, and is zero (initially) or a small finite amount at t>0. D is the diffusion coefficient that is assumed to be constant.

Eq 6 can be solved analytically for the initial and boundary conditions eqs 7-9 by a standard method such as separation variables or Laplace transform and yields:

$$C = C_S \left[ 1 - 2\left(1 - \frac{C_0}{C_S}\right) \sum_{n=0}^{\infty} \frac{\exp(-\lambda_n^2 Dt)\sin\lambda_n z}{L\lambda_n} \right], \quad (10)$$

where $\lambda_n = \left(n + \frac{1}{2}\right)\frac{\pi}{L}$.

An experimentally observed quantity at a specified time is the total concentration (or mass) of dissolved gas in ionic liquid, and not the concentration profile in z. This space-averaged concentration at a given time, <C>, can be calculated from eq 11.

$$\langle C \rangle = \int_0^L C dz/L \quad (11)$$

$$\langle C \rangle = C_S \left[ 1 - 2\left(1 - \frac{C_0}{C_S}\right) \sum_{n=0}^{\infty} \frac{\exp(-\lambda_n^2 Dt)}{L^2 \lambda_n^2} \right] \quad (12)$$

Although eq 12 contains an infinite summation, only the first few terms, except for initial small time periods, are sufficient in practical applications. In this work, the summation was terminated after ten terms when the numerical contribution to the summation in <C> became less than $10^{-12}$. By analyzing experimental data with this equation, we obtained the saturation concentration ($C_S$) and diffusion constant (D) at given T and P, when $C_o$ was known.

EXAMPLE 1

Selectivity Ratio

Infinite activity coefficients and selectivities are shown for several refrigerants in Table 2. The selectivity is calculated relative to HFC-32 in 1-butyl-3-methylimidazolium hexafluorophosphate, [bmim][PF$_6$]. Standard activity coefficient models (S. I., Sandler, Chemical and Engineering Thermodynamics, 3rd Edition (1999) John Wiley and Sons, Inc., New York, Chapter 7) were used to fit solubility data in order to calculate the infinite activity coefficients.

As shown, HFC-134a, HFC-152a, HFC-125 and HFC-143a have selectivity values well above 2.0, which suggest that a separation of these compounds from HFC-32 by extractive distillation is feasible using [bmim][PF$_6$] as the entrainer.

The solubility curves for these refrigerant pairs are shown in FIGS. 3 to 8 at constant T of 10, 25, 50, and 75° C. The differences in the solubility curves for each hydrofluorocarbon tested can be described by plotting the pressure (P) divided by the saturation pressure at a constant temperature (Po) versus mole fraction of the hydrofluorocarbon absorbed in the ionic liquid. The large differences shown in FIG. 17 indicate that ionic liquids such as [bmim][PF$_6$] in this example can effectively separate these hydrofluorocarbons.

In addition, selectivities for $O_2$ and hydrocarbons can be calculated using known solubilities as found in D. Camper, et al. (Eng. Chem. Res. (2004) 43:3049-3054), J. L. Anthony, et al. (J. Phys. Chem. B (2002) 106:7315-7320), and P. Husson-Borg, et al. (J. Chem. Eng. Data (2003) 48:480-485).

TABLE 2

Selectivity Ratio based on Infinite Activity Coefficient

| Refrigerant | Ionic liquid | Temperature ° C. | Infinite Activity Coefficient | Selectivity |
|---|---|---|---|---|
| HFC-32 | [bmim][PF$_6$] | 10 | 0.696166 | 1.0000 |
|  |  | 25 | 0.609595 | 1.0000 |
|  |  | 50 | 0.799270 | 1.0000 |
|  |  | 75 | 1.032475 | 1.0000 |
| HFC-32 | [bmim][BF$_4$] | 10 | 0.854236 | — |
|  |  | 25 | 0.944715 | — |
|  |  | 50 | 1.095222 | — |
|  |  | 75 | 1.329155 | — |
| HFC-134a | [bmim][PF$_6$] | 10 | 1.667320 | 2.3950 |
|  |  | 25 | 1.827300 | 2.9976 |
|  |  | 50 | 2.439530 | 3.0522 |
|  |  | 75 | 3.093420 | 2.9961 |
| HFC-152a | [bmim][PF$_6$] | 10 | 0.844508 | 1.2131 |
|  |  | 25 | 1.018130 | 1.6702 |
|  |  | 50 | 1.641290 | 2.0535 |
|  |  | 75 | 1.782670 | 1.7266 |
| HFC-125 | [bmim][PF$_6$] | 10 | 3.294988 | 4.7330 |
|  |  | 25 | 3.588462 | 5.8866 |
|  |  | 50 | 4.318588 | 5.4032 |
|  |  | 75 | 4.870422 | 4.7172 |
| HFC-143a | [bmim][PF$_6$] | 10 | 3.977224 | 5.7130 |
|  |  | 25 | 4.137623 | 6.7875 |
|  |  | 50 | 4.473862 | 5.5974 |
|  |  | 75 | 4.691909 | 4.5443 |

EXAMPLE 2

Separation of a Mixture Comprising Difluoromethane and Pentafluoroethane

Figure 2:
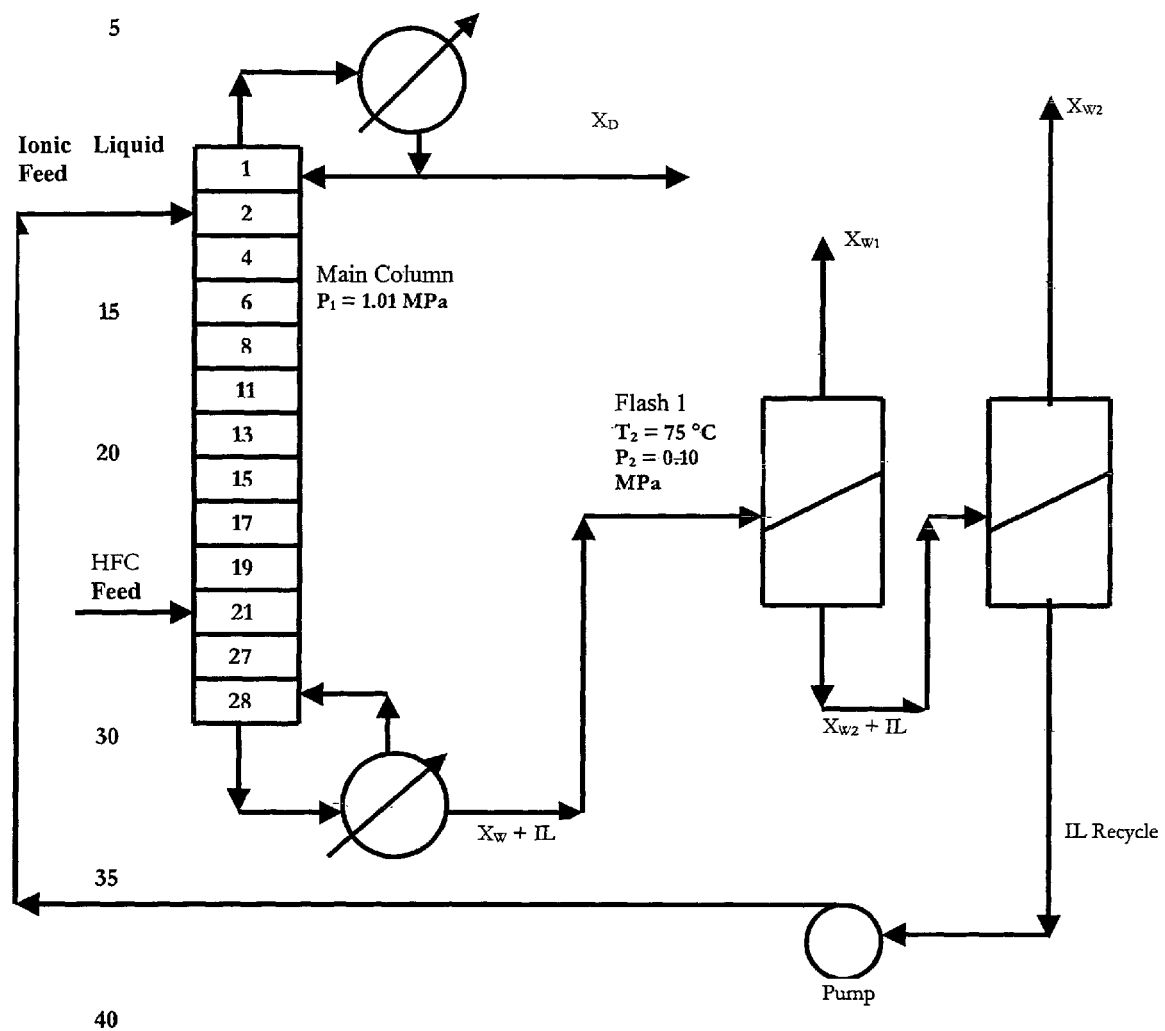
FIG. 2 is a schematic diagram of a simple ASPEN extractive distillation process.
Figure 3:
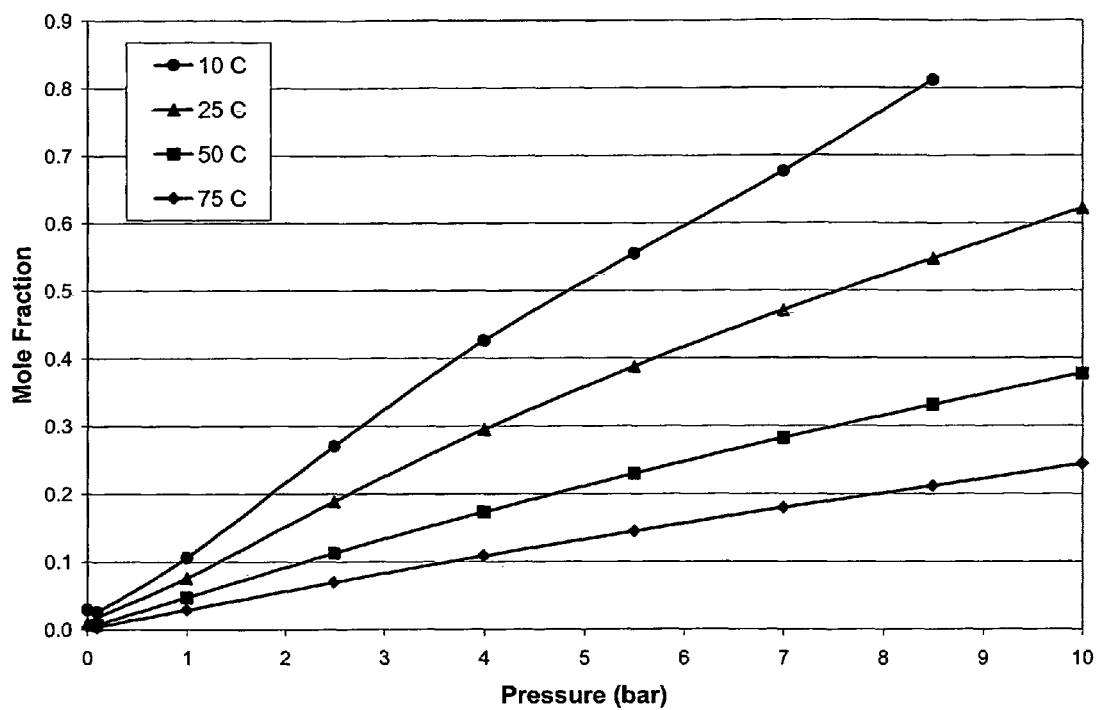
FIG. 3 shows measured isothermal solubility data (in mole fraction) of the system HFC-32+[bmim][$PF_6$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 4:
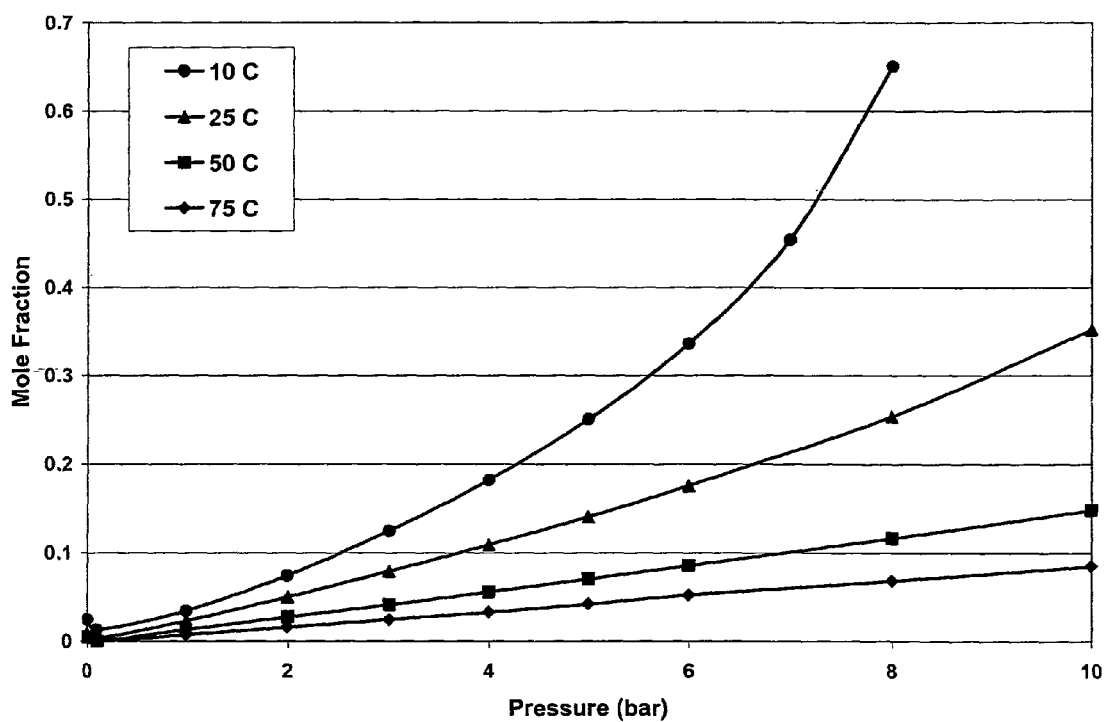
FIG. 4 shows measured isothermal solubility data (in mole fraction) of the system HFC-125+[bmim][$PF_6$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 5:
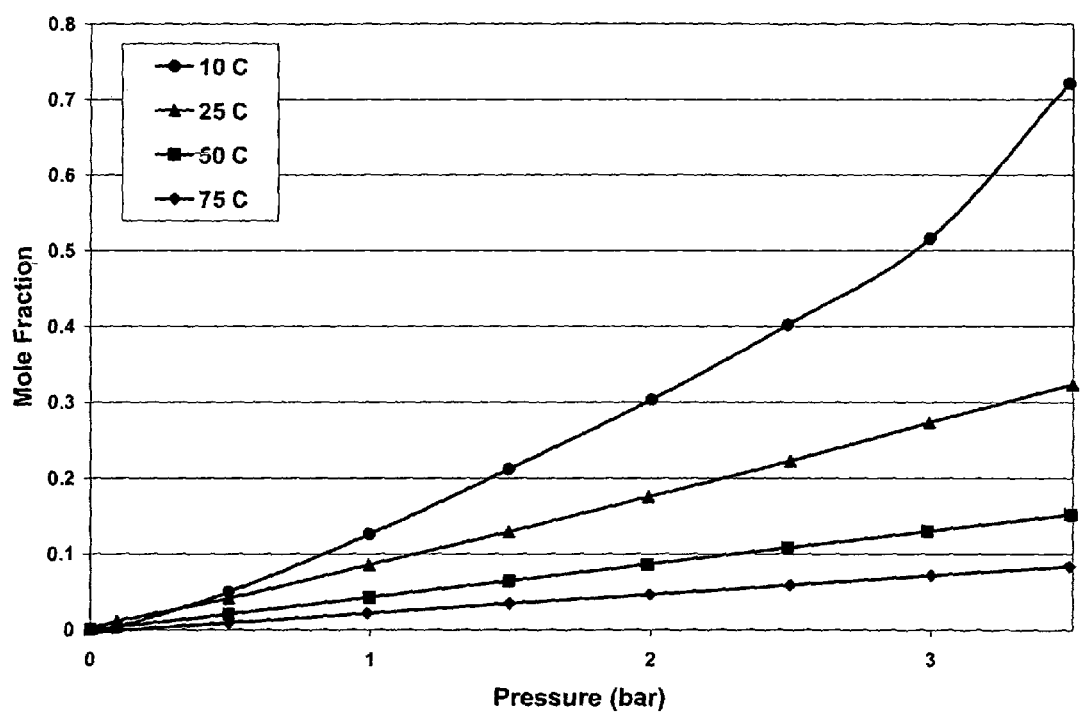
FIG. 5 shows measured isothermal solubility data (in mole fraction) of the system HFC-134a+[bmim][$PF_6$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 6:
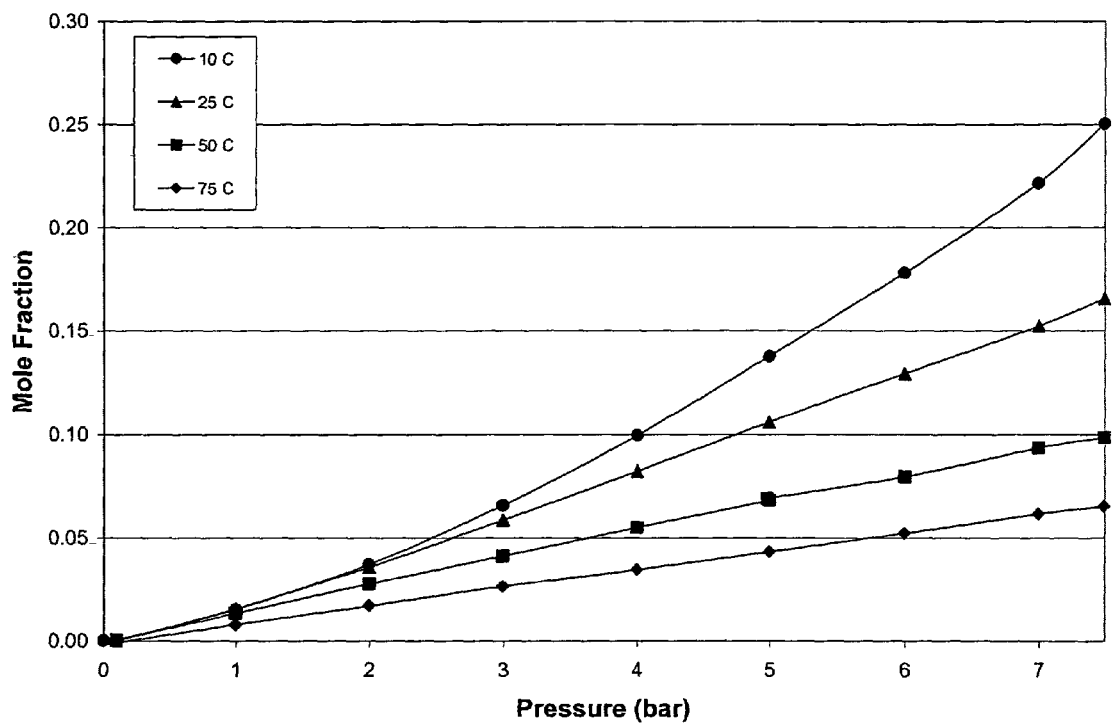
FIG. 6 shows measured isothermal solubility data (in mole fraction) of the system HFC-143a+[bmim][$PF_6$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 7:
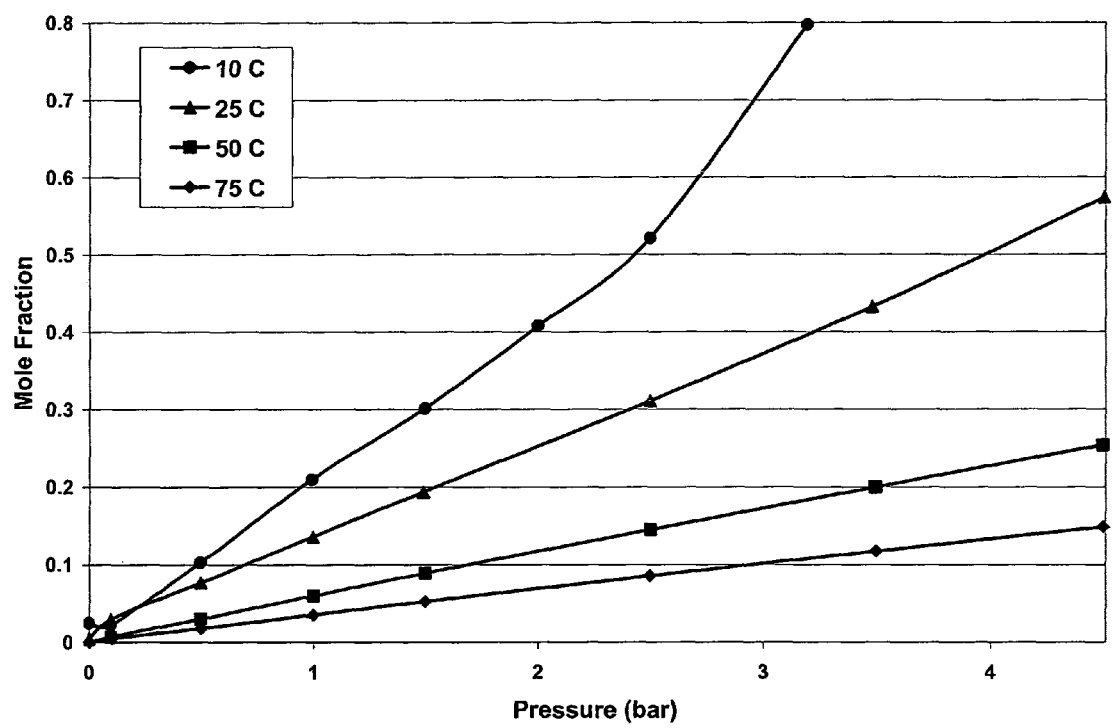
FIG. 7 shows measured isothermal solubility data (in mole fraction) of the system HFC-152a+[bmim][$PF_6$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 8:
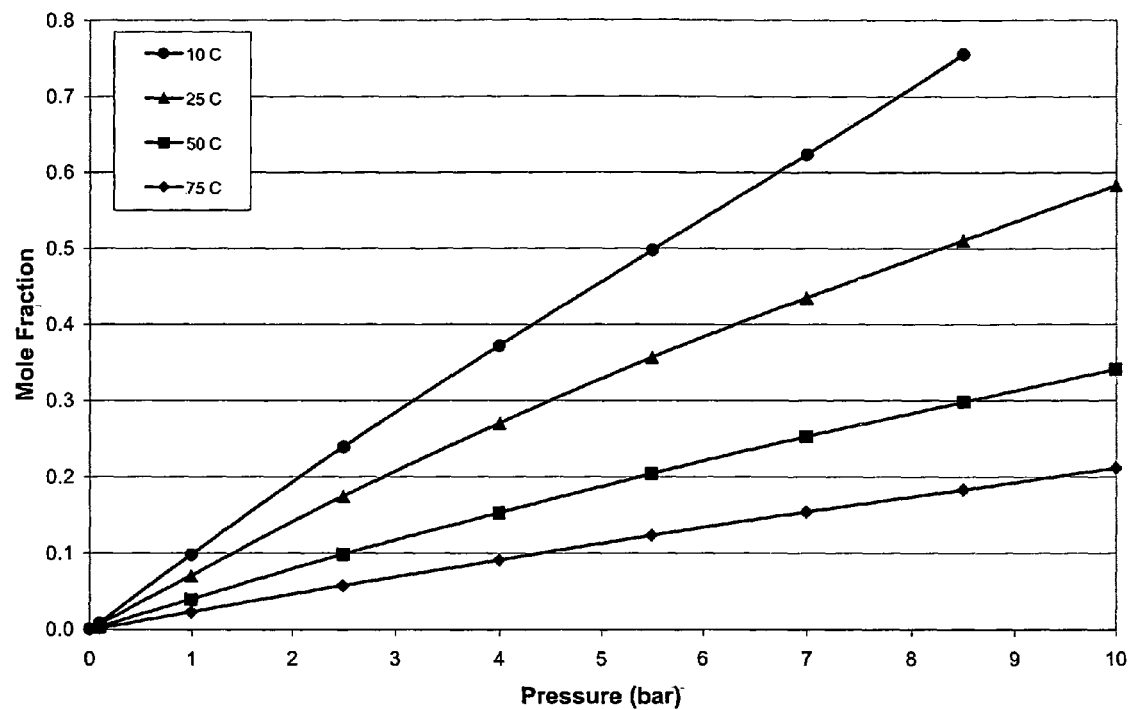
FIG. 8 shows measured isothermal solubility data (in mole fraction) of the system HFC-32+[bmim][$BF_4$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.

An Aspen Plus® process simulation was used to model the extractive distillation process for the separation of a mixture consisting of difluoromethane and pentafluoroethane using [bmim][PF$_6$] as the entrainer. The Aspen flowsheet used for this simulation consists of a main column modeled with Rad-Frac and two outlet flash drums for the regeneration of the ionic liquid (IL), which is recycled back into the main column as shown in FIG. 2. The immeasurable vapor pressure of the ionic liquid was taken into consideration by fitting the Extended Antoine equation value close to zero. The ionic liquid was treated as a non-dissociating component and assumption of an ideal vapor phase was made, therefore, the investigated Vapor-Liquid Equilibrium (VLE) data could be described by the liquid concentration and activity coefficient. Nonrandom two-liquid (NRTL) binary interaction parameters (S. I., Sandler, Chemical and Engineering Thermodynamics, 3$^{rd}$ Edition (1999) John Wiley and Sons, Inc., New York, Chapter 7) between the hydrofluorocarbons and the ionic liquid were generated using (P, T, x) data obtained from solubility experiments (see Examples 3 and 4 for solubility data for HFC-32 and HFC-125, respectively, in bmim[PF$_6$]). Table 3 shows the modeling results for the separation of the mixture comprising HFC-32 and HFC-125 using bmim[PF$_6$]. Two cases were evaluated. The first case consists of a mixture of 95.11 mol % HFC-32 and 4.78 mol % HFC-125, which forms an azeotrope at 10° C. The second case is a mixture of 50 mol % HFC-32 and 50 mol % HFC-125 at room temperature (25° C.). For the first case, the hydrofluorocarbon mixture (feed) is fed into the main column through stage 13 at 10° C. The ionic liquid is fed through the $2^{nd}$ stage of the main column at 0° C. For the second case, the hydrofluorocarbon mixture is fed into the main column at stage 21 at room temperature. The ionic liquid is also fed into the column at room temperature.

As shown in Table 3, over 98 percent of the overhead product (HFC-125) fed into the main column is recovered in the first and second cases, respectively. The purity in both cases is over 99.2%. A higher purity HFC-125 is produced in the overhead product when the azeotropic feed composition (95.11 mol % HFC-32/4.78 mol % HFC-125) is fed into the main column via stage 13 as compared to the 50:50 mixture fed at stage 21. The advantage of using two flash drums for the regeneration of the ionic liquid can also be seen in both cases. When the azeotropic composition (case 1) is fed into the column, 92.1% (0.2531 kg/s) of the 0.2749 kg/s HFC-32 fed into the main column is recovered in the first flash; when the mixture of 50 mol % HFC-32 and 50 mol % HFC-125 is fed into the column, 91.0% (0.1315 kg/s) of the 0.1445 kg/s HFC-32 fed into the main column is recovered. In both cases, the remaining HFC-32 is recovered in the second flash drum overhead. This reduces the amount of impurities in the ionic liquid being recycled to less than 0.3 mol %.

TABLE 3

Aspen Results

| | $1^{st}$ Case | $2^{nd}$ Case |
|---|---|---|
| Feed Flow | | |
| Ionic Liquid (IL) (kg/s) | 3.9472 | 3.9472 |
| HFC-32 (kg/s) | 0.2749 | 0.1445 |
| HFC-125 (kg/s) | 0.0326 | 0.3334 |
| HFC gas mixture Temp. (K.) | 283.15 | 298.15 |
| Ionic Liquid (IL) Temp. (K.) | 273.15 | 298.15 |
| Main Column | | |
| HFC-125, overhead (kg/s) | 0.0323 | 0.3323 |
| HFC-125 purity ($x_D$) | 99.1% | 99.7% |
| IL + HFC-32, bottoms (kg/s) | 4.2244 | 4.0927 |
| Theoretical stages | 28 | 28 |
| Operating pressure (Pa) | $10^6$ | $10^6$ |
| Reflux ratio | 0.25 | 0.25 |
| Ionic Liquid stage | 2 | 2 |
| Feed stage | 13 | 21 |
| Condenser Temperature (K.) | 286.33 | 286.38 |
| Reboiler Temperature (K.) | 346.97 | 398.56 |
| Condenser duty (kW) | −1.43 | −14.47 |
| Reboiler duty (kW) | 358.01 | 714.62 |
| Flash drum 1 | | |
| Operating pressure (Pa) | $10^5$ | $10^5$ |
| Operating Temperature (K.) | 348.15 | 398.56 |
| HFC-32, Overhead (kg/s) | 0.2531 | 0.1315 |
| HFC-32, Overhead purity ($x_{w1}$) | 99.9% | 99.6% |
| Heat duty (kW) | 76.31 | 23.10 |
| Flash drum 2 | | |
| Operating pressure (Pa) | $10^4$ | $10^4$ |
| Operating Temperature (K.) | 348.15 | 398.56 |
| HFC-32, Overhead (kg/s) | 0.0217 | 0.0125 |
| HFC-32, Overhead purity ($x_{w2}$) | 99.9% | 99.8% |
| Ionic Liquid, Recycle (kg/s) | 3.9472 | 3.9472 |
| Ionic Liquid, Recycle purity | 99.7% | 99.8% |
| Heat duty (kW) | 5.59 | 2.21 |
| Overall heat duty (kW) | 441.34 | 754.40 |

Examples 3-35 provide solubility and diffusivity results for several hydrofluorocarbon compounds. These data are used for selectivity determinations (as shown in Example 1) and for Aspen® modeling (as shown in Example 2).

Examples 3-7 and FIGS. 3-7 show solubility and diffusivity results for several hydrofluorocarbons (HFC-32, HFC-125, HFC-134a, HFC-143a, and HFC-152a) in one ionic liquid, [bmim][$PF_6$], at 10, 25, 50, and 75° C. Compositions were prepared that consisted of HFC-32 and [bmim][$PF_6$] from about 0.3 to about 81.2 mole percent of HFC-32 over a temperature range from 10 to 75° C. at a pressure from about 0.1 to 10 bar. Compositions were prepared that consisted of HFC-125 and [bmim][$PF_6$] from about 0.1 to about 65.1 mole percent of HFC-125 over a temperature range from 10 to 75° C. at a pressure from about 0.1 to 10 bar. Compositions were prepared that consisted of HFC-134a and [bmim][$PF_6$] from about 0.1 to about 72.1 mole percent of HFC-134a over a temperature range from 10 to 75° C. at a pressure from about 0.1 to 3.5 bar. Compositions were prepared that consisted of HFC-143a and [bmim][$PF_6$] from about 0.1 to about 26.5 mole percent of HFC-143a over a temperature range from 10 to 75° C. at a pressure from about 0.1 to 7.5 bar. Compositions were prepared that consisted of HFC-152a and [bmim][$PF_6$] from about 0.5 to about 79.7 mole percent of HFC-152a over a temperature range from 10 to 75° C. at a pressure from about 0.1 to 4.5 bar.

Examples 8-14 and 17-29 and FIGS. 8, 11-16 show solubility and diffusivity results for HFC-32 in several additional ionic liquids.

Examples 30-35 show solubility and diffusivity results for HFC-134a in several ionic liquids.

Figure 9:
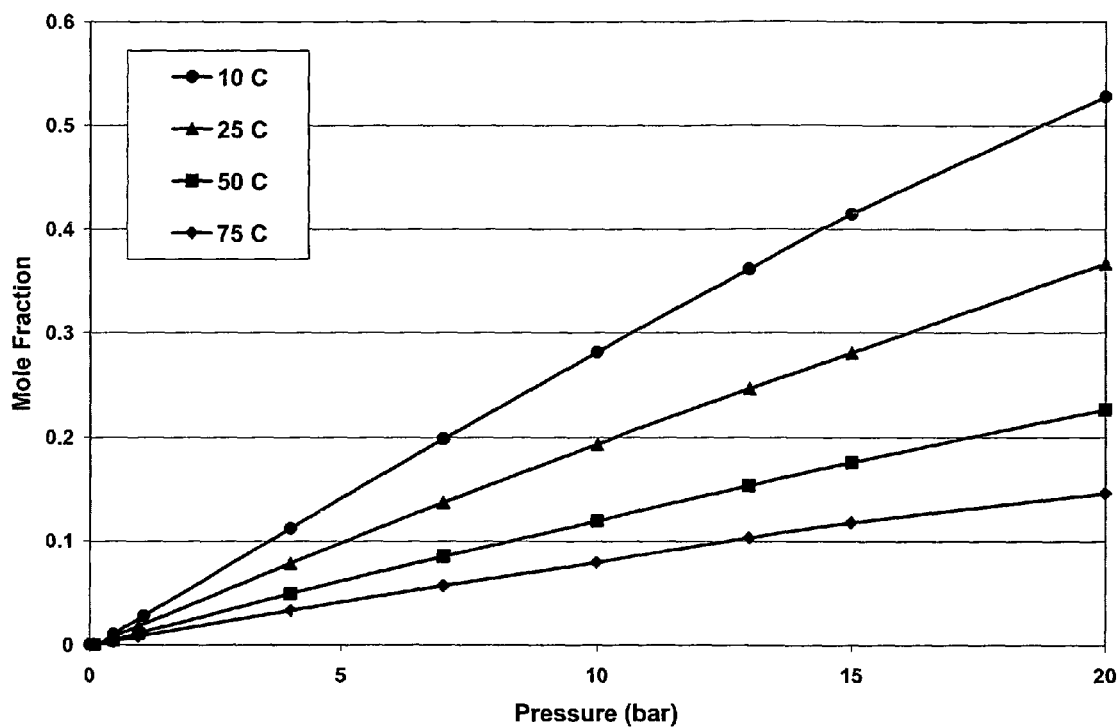
FIG. 9 shows measured isothermal solubility data (in mole fraction) of the system HFC-23+[bmim][$PF_6$] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 10:
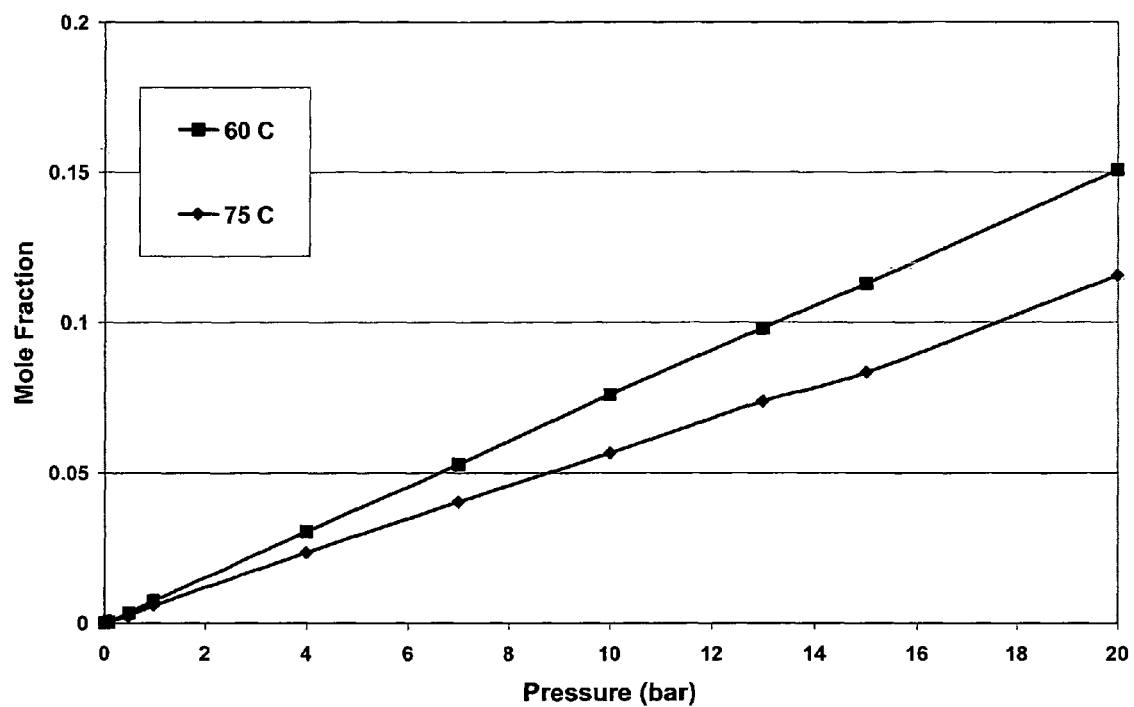
FIG. 10 shows measured isothermal solubility data (in mole fraction) of the system HFC-23+[emim][PF$_6$] as a function of pressure. Filled squares (■) represent measured isothermal data at 60° C., and filled diamonds (♦) represent measured isothermal data at 75° C. Solid lines represent data trends.
Figure 11:
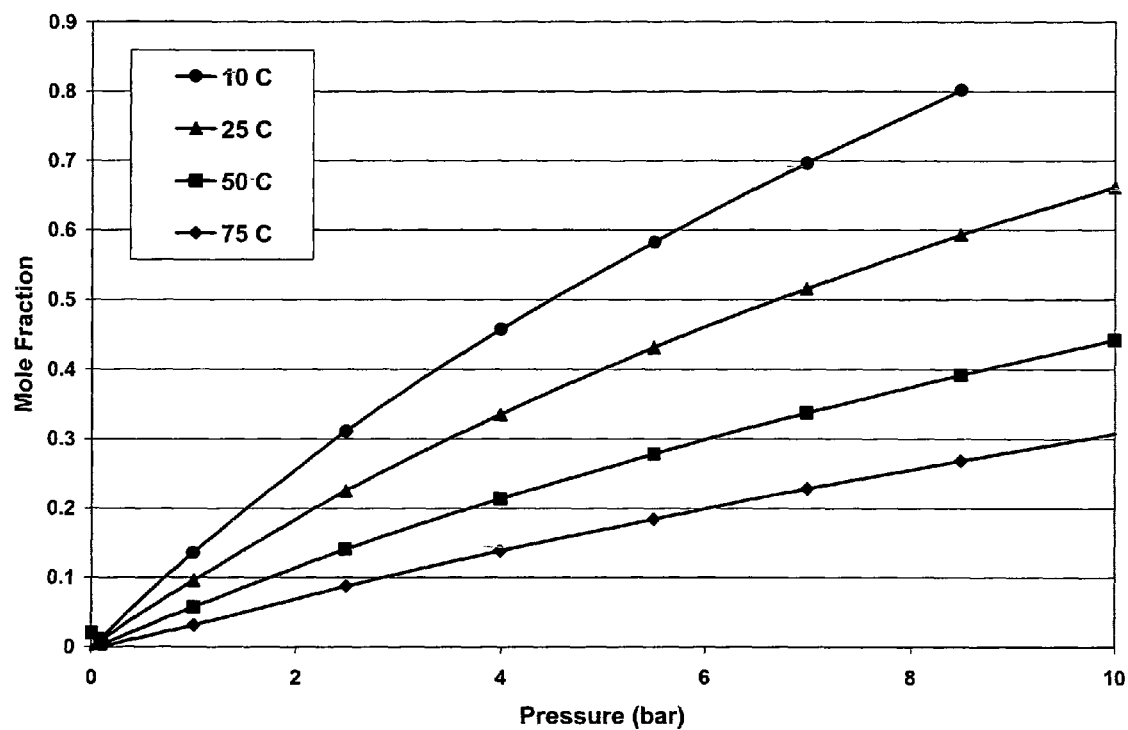
FIG. 11 shows measured isothermal solubility data (in mole fraction) of the system HFC-32+[dmpim][TMeM] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 12:
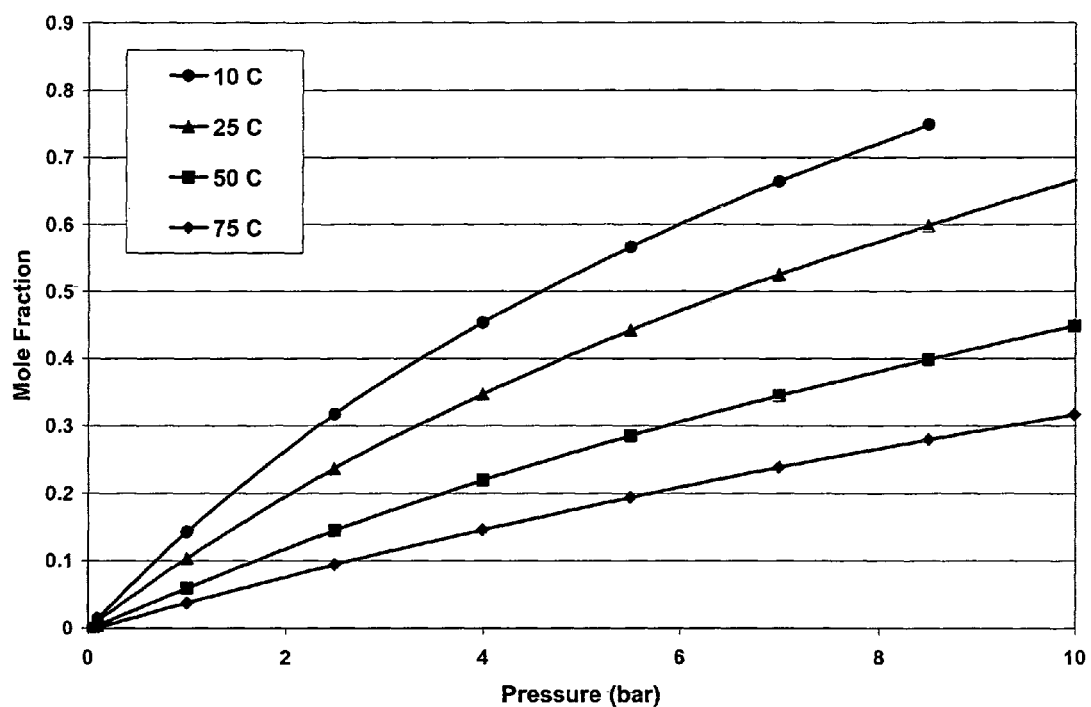
FIG. 12 shows measured isothermal solubility data (in mole fraction) of the system HFC-32+[emim][BEI] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 13:
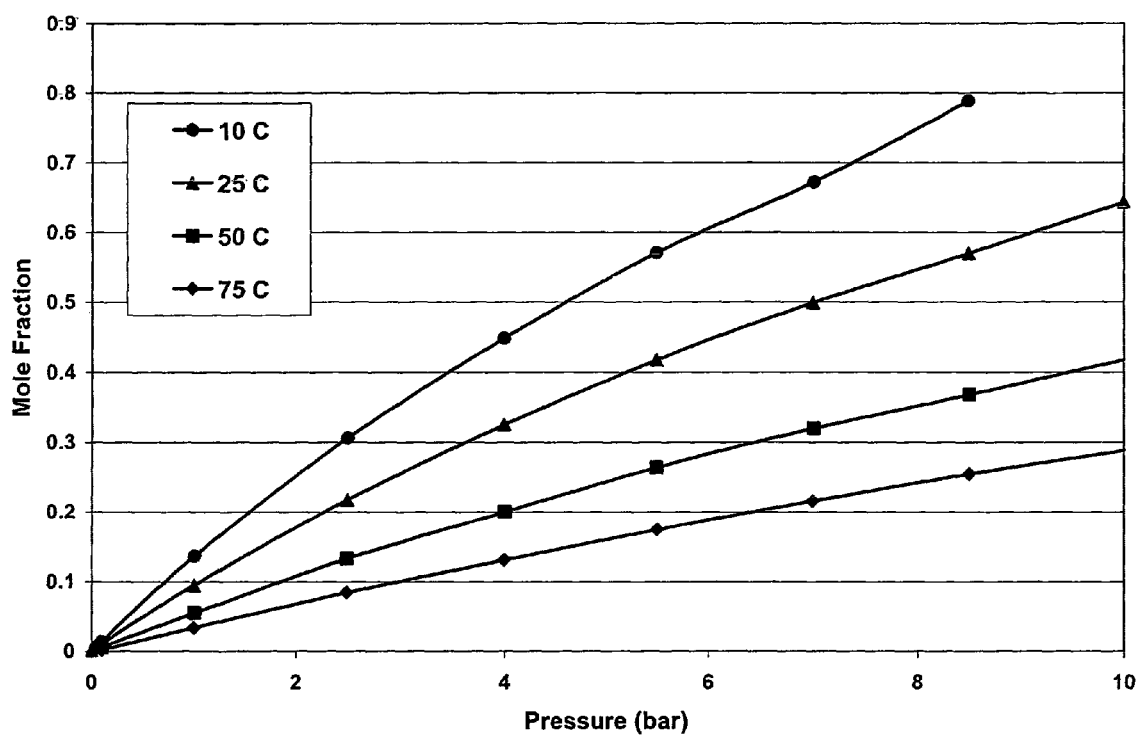
FIG. 13 shows measured isothermal solubility data (in mole fraction) of the system HFC-32+[emim][BMeI] as a function of pressure. Filled circles (●) represent measured isothermal data at 10° C., filled triangles (▲) represent measured isothermal data at 25° C., filled squares (■) represent measured isothermal data at 50° C., and filled diamonds (▲) represent measured isothermal data at 75° C. Solid lines represent data trends.
Figure 14:
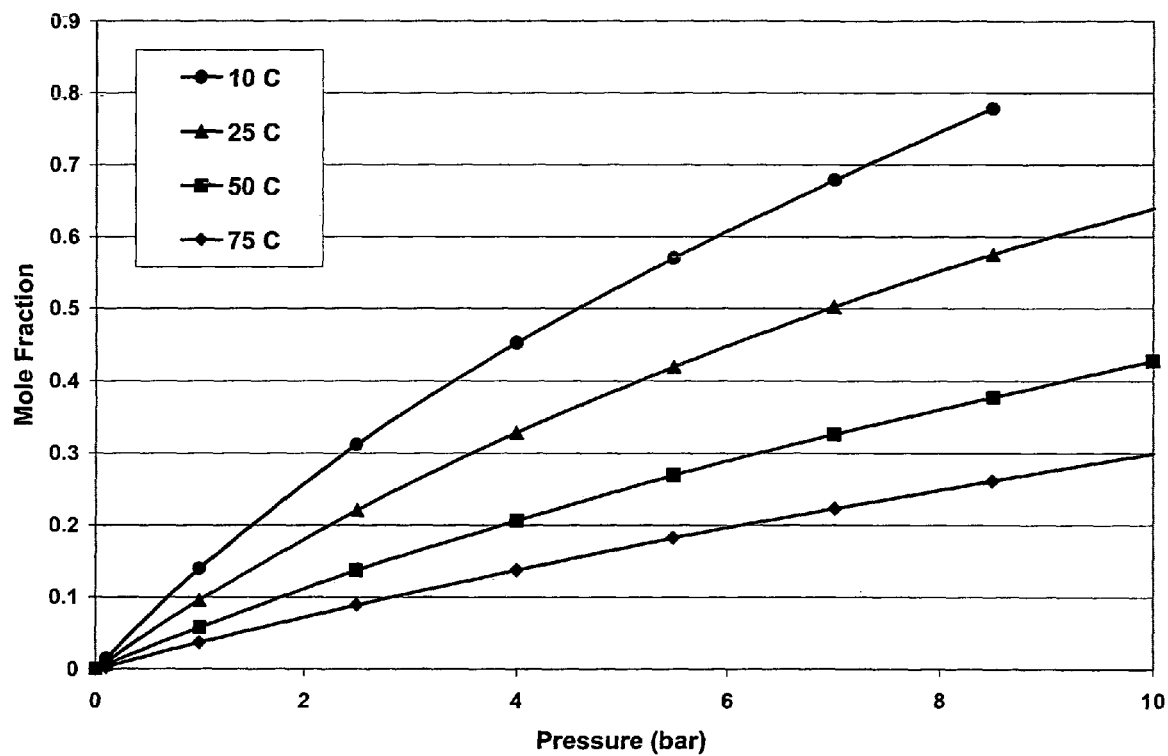
FIG. 14 shows measured isothermal solubility data (in mole fraction) of the system HFC-32+[pmpy][BMeI] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 15:
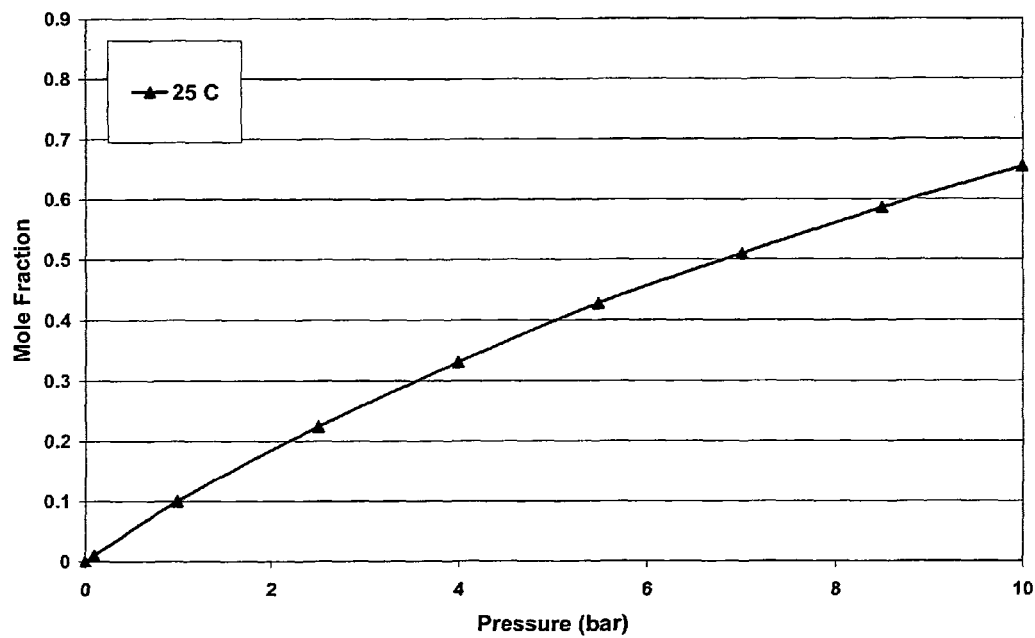
FIG. 15 shows measured isothermal solubility data (in mole fraction) of the system HFC-32+[bmpy][BMeI] as a function of pressure. Filled circles (●) represent measured isothermal data at 10° C., filled triangles (▲) represent measured isothermal data at 25° C., filled squares (■) represent measured isothermal data at 50° C., and filled diamonds (♦) represent measured isothermal data at 75° C. Solid lines represent data trends.
Figure 16:
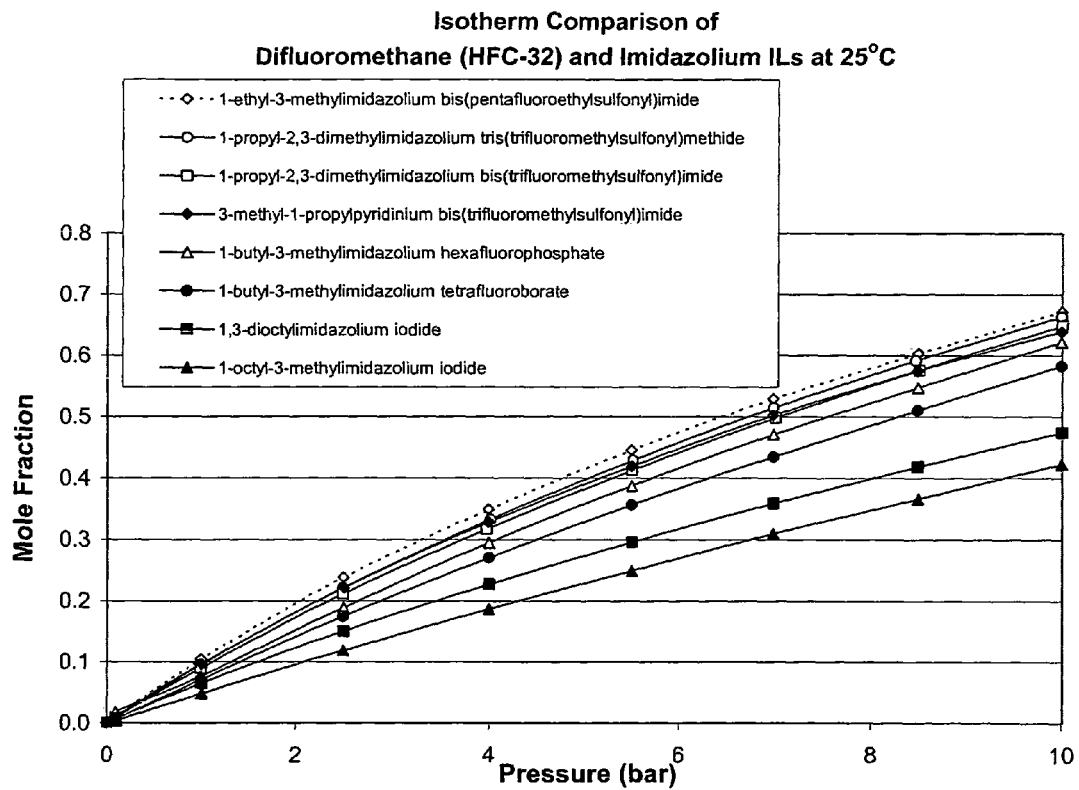
FIG. 16 shows measured isothermal solubility data at 25° C. of the systems HFC-32+eight different ionic liquids as a function of pressure for comparison. Open diamonds (◇) represent measured isothermal data for HFC-32+1-ethyl-3-methylimidazolium bis(pentafluoroethylsulfonyl)imide, open circles (○) represent measured isothermal data for HFC-32+1-propyl-2,3-dimethylimidazolium tris(trifluoromethylsulfonyl)methide at 25° C., open squares (□) represent measured isothermal data for HFC-32+1-propyl-2,3-dimethylimidazolium bis(trifluoromethylsulfonyl)imide at 25° C., closed diamonds (♦) represent measured isothermal data for HFC-32+3-methyl-1-propylpyridinium bis(trifluoromethylsulfonyl)imide, open triangles (△) represent measured isothermal data for HFC-32+1-butyl-3-methylimidazolium hexafluorophosphate at 25° C., filled circles (●) represent measured isothermal data for HFC-32+1-butyl-3-methylimidazolium tetrafluoroborate at 25° C., filled squares (■) represent measured isothermal data for HFC-32+1,3-dioctylimidazolium iodide at 25° C., and filled triangles (▲) represent measured isothermal data for HFC-32+1-octyl-3-methylimidazolium iodide at 25° C. Solid lines represent data trends.

Examples 15 and 16 and FIGS. 9 and 10 show solubility and diffusivity results for HFC-23 in the ionic liquids [bmim][$PF_6$] and [emim][$PF_6$].

Compositions were prepared that consisted of HFC-32 and [bmim][$BF_4$] from about 0.1 to about 76.5 mole percent of HFC-32 over a temperature range from 10 to 75° C. at a pressure from about 0.1 to 10 bar. Compositions were prepared that consisted of HFC-32 and [dmpim][TMeM] from about 0.9 to about 66 mole percent of HFC-32 at a temperature of 25° C. and a pressure from about 0.1 to 10 bar. Compositions were prepared that consisted of HFC-32 and [omim][I] from about 0.4 to about 41.6 mole percent of HFC-32 at a temperature of 25° C. and a pressure from about 0.1 to 10 bar. Compositions were prepared that consisted of HFC-32 and [doim][I] from about 0.7 to about 46.8 mole percent of HFC-32 at a temperature of 25° C. and a pressure from about 0.1 to 10 bar. Compositions were prepared that consisted of HFC-32 and [emim][BEI] from about 1.0 to about 66.6 mole percent of HFC-32 at a temperature of 25° C. and a pressure from about 0.1 to 10 bar. Compositions were prepared that consisted of HFC-32 and [dmpim][TMeM] from about 0.8 to about 64.5 mole percent of HFC-32 at a temperature of 25° C. and a pressure from about 0.1 to 10 bar. Compositions were prepared that consisted of HFC-32 and [pmpy][BMeI] from about 1.0 to about 63.9 mole percent of HFC-32 at a temperature of 25° C. and a pressure from about 0.1 to 10 bar. Compositions were prepared that consisted of HFC-32 and [emim][BMeI] from about 0.1 to about 78.5 mole percent of HFC-32 over a temperature range from 10 to 75° C. at a pressure from about 0.1 to 10 bar. Compositions were prepared that consisted of HFC-32 and [bmpy][BMeI] from about 1.0 to about 64.8 mole percent of HFC-32 at a temperature of 25° C. and a pressure from about 0.1 to 10 bar. Compositions were prepared that consisted of HFC-32 and [emim][TFES] from about 1.0 to about 47.1 mole percent of HFC-32 at a temperature of 25° C. and a pressure from about 0.1 to 10 bar. Compositions were prepared that consisted of HFC-32 and [bmim][TFES] from about 1.0 to about 55.0 mole percent of HFC-32 at a temperature of 25° C. and a pressure from about 0.1 to 10 bar. Compositions were prepared that consisted of HFC-32 and [odmim][TFES] from about 1.0 to about 56.2 mole percent of HFC-32 at a temperature of 25° C. and a pressure from about 0.1 to 10 bar. Compositions were prepared that consisted of HFC-32 and [hmim][TFES] from about 1.0 to about 58.6 mole percent of HFC-32 at a temperature of 25° C. and a pressure from about 0.1 to 10 bar. Compositions were prepared that consisted of HFC-23 and [bmim][PF$_6$] from about 0.1 to about 52.8 mole percent of HFC-23 over a temperature range from 10 to 75° C. at a pressure from about 0.1 to 20 bar. Compositions were prepared that consisted of HFC-23 and [emim][PF$_6$] from about 0.1 to about 15.1 mole percent of HFC-23 over a temperature range from 60 to 75° C. at a pressure from about 0.1 to 20 bar.

Figure 17:
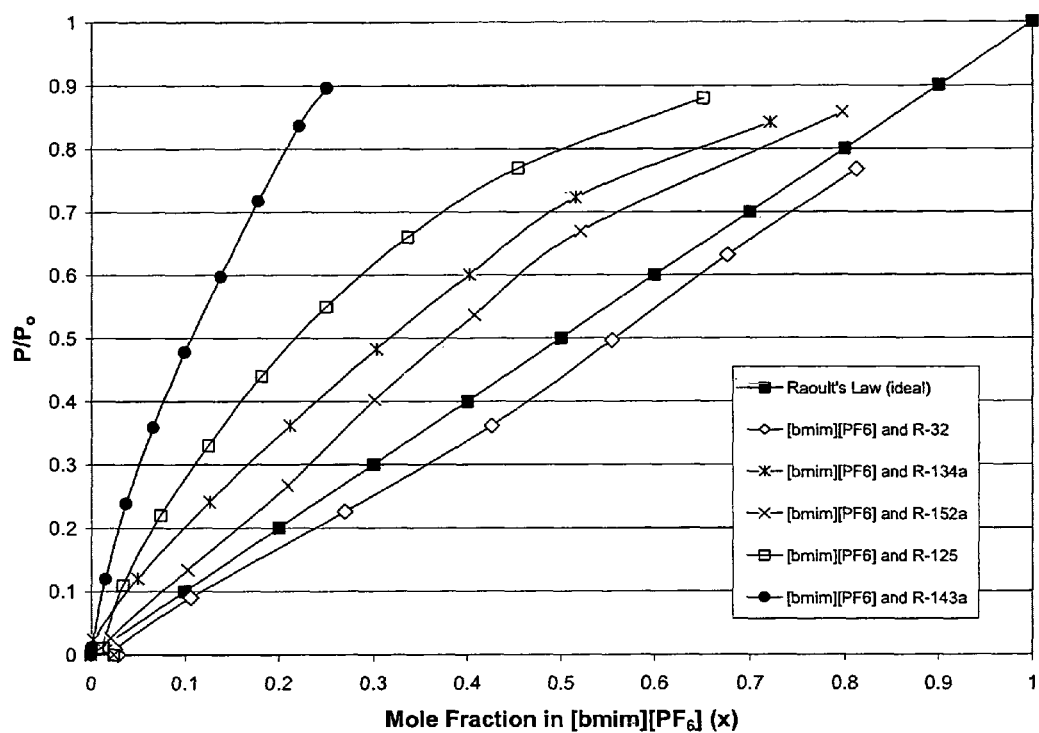
FIG. 17 shows measured isothermal solubility data (in mole fraction) at 10° C. of the systems HFC-32, HFC-152a, HFC-134a, HFC-125, and HFC-143a+[bmim][PF$_6$] in terms of absolute pressure divided by the gas saturation pressure at 10° C. shown by ratio (P/P$_0$). Open diamonds (◇) represent measured isothermal data for HFC-32 at 10° C. with P$_0$=11.069 bar, open cross hatch (X) represents measured isothermal data for HFC-152a at 10° C. with P$_0$=3.7277 bar, filled circles (●) represent measured isothermal data for HFC-134a at 10° C. with P$_0$=4.1461 bar, open squares (□) represent measured isothermal data for HFC-125 at 10° C. with P$_0$=9.0875 bar, filled circles (●) represent measured isothermal data for HFC-143a at 10° C. with P$_0$=8.3628 bar. Solid lines represent data trend and dashed line represents Raoult's Law.

FIG. 17 shows measured isothermal solubility data (in mole fraction) at 10° C. of the systems HFC-32, HFC-152a, HFC-134a, HFC-125, and HFC-143a+[bmim][PF$_6$] in terms of absolute pressure divided by the gas saturation pressure ($P_0$) at 10° C. shown by ratio ($P/P_0$). The saturation pressures for HFC-32, HFC-125, HFC-134a, HFC-143a, and HFC-152a at 10° C. are $P_0$=11.069 bar, $P_0$=3.7277 bar, $P_0$=4.1461 bar, $P_0$=9.0875, and $P_0$=8.3628 bar, respectively. Negative deviations from Raoult's law (i.e. curvature below the dashed line) indicate strong interaction between the refrigerant and the ionic liquid, which indicates high solubility. In particular HFC-32 has negative deviation from Raoult's law as shown in FIG. 17. Compositions comprise HFC-32 and [bmim][PF$_6$] from about 0.1 to 63 mole percent of HFC-32 at 10° C. and $P/P_0$ from about 0.1 to about 0.63. Strong positive deviations from Raoult's law (i.e. curvature above the dashed line) are more typical and indicate refrigerant and ionic liquids are less soluble and eventually may form a liquid-liquid phase separation. Compositions comprise HFC-152a and [bmim][PF$_6$] from about 0.1 to about 80 mole percent of HFC-152a at 10° C. and $P/P_0$ from 0.1 to about 0.86. Compositions comprise HFC-134a and [bmim][PF$_6$] from about 0.1 to about 72 mole percent of HFC-134a at 10° C. and $P/P_0$ from about 0.1 to about 0.84. Compositions comprise HFC-125 and [bmim][PF$_6$] from about 0.1 mole to about 65 mole percent of HFC-125 at 10° C. and $P/P_0$ from about 0.1 to about 0.88. Compositions comprise HFC-143a and [bmim][PF$_6$] from about 0.1 to about 25 mole percent at 10° C. and $P/P_0$ from about 0.1 to about 0.90.

Example 36 provides a description of the microbalance components.

EXAMPLE 3

Solubility of difluoromethane (HFC-32) in 1-butyl-3-methylimidazolium hexafluorophosphate A solubility and diffusivity study was made at temperatures of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 4a, 4b, 4c and 4d provide data for $C_o$, $C_s$, D, $X_{calc}$, and $X_{meas}$ at temperatures of 10, 25, 50 and 75° C., respectively.

TABLE 4a

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 10.0 | 0.0979 | 0.52 | 0.54 | 1.54E−09 | 0.029 | 0.026 |
| 10.0 | 0.9957 | 0.82 | 2.53 | 1.94E−11 | 0.124 | 0.106 |
| 10.0 | 2.4967 | 3.32 | 7.56 | 1.71E−11 | 0.309 | 0.270 |
| 10.0 | 3.9964 | 8.18 | 12.38 | 3.65E−11 | 0.436 | 0.426 |
| 10.0 | 5.4975 | 14.44 | 18.71 | 6.34E−11 | 0.557 | 0.555 |
| 10.0 | 6.9965 | 22.12 | 27.85 | 7.42E−11 | 0.678 | 0.676 |
| 10.0 | 8.4954 | — | — | — | — | 0.812 |

TABLE 4b

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 24.9 | 0.0965 | 0.16 | 0.21 | 1.84E−10 | 0.012 | 0.018 |
| 25.0 | 0.9952 | 0.49 | 1.69 | 2.45E−11 | 0.086 | 0.076 |
| 25.0 | 2.4965 | 2.22 | 4.53 | 2.44E−11 | 0.206 | 0.189 |
| 25.0 | 3.9979 | 5.05 | 7.37 | 3.51E−11 | 0.303 | 0.295 |
| 24.9 | 5.4969 | 8.23 | 10.47 | 5.41E−11 | 0.390 | 0.387 |
| 24.9 | 6.9950 | 11.82 | 14.09 | 6.75E−11 | 0.473 | 0.471 |
| 25.0 | 8.5012 | 15.75 | 18.26 | 8.33E−11 | 0.550 | 0.548 |
| 24.9 | 9.9994 | 20.38 | 23.31 | 8.84E−11 | 0.624 | 0.622 |

TABLE 4c

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 49.6 | 0.0992 | 0.00 | 0.12 | 4.76E−11 | 0.007 | 0.006 |
| 49.9 | 0.9954 | 0.33 | 0.92 | 5.28E−11 | 0.048 | 0.047 |
| 49.9 | 2.4963 | 1.43 | 2.31 | 5.29E−11 | 0.115 | 0.113 |
| 49.9 | 3.9949 | 2.84 | 3.72 | 5.98E−11 | 0.174 | 0.173 |
| 49.9 | 5.4966 | 4.41 | 5.22 | 5.99E−11 | 0.231 | 0.229 |
| 49.9 | 6.9965 | 5.81 | 6.72 | 7.69E−11 | 0.282 | 0.282 |
| 50.0 | 8.4959 | 7.37 | 8.32 | 8.54E−11 | 0.331 | 0.331 |
| 50.0 | 9.9959 | 9.78 | 10.05 | 4.04E−11 | 0.379 | 0.377 |

TABLE 4d

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 75.0 | 0.0988 | 0.00 | 0.06 | 7.12E−11 | 0.003 | 0.003 |
| 75.0 | 0.9968 | 0.30 | 0.56 | 8.19E−11 | 0.030 | 0.029 |
| 75.0 | 2.4950 | 0.96 | 1.38 | 8.14E−11 | 0.071 | 0.069 |
| 75.0 | 3.9944 | 1.74 | 2.19 | 9.82E−11 | 0.109 | 0.108 |
| 74.9 | 5.4983 | 2.60 | 3.03 | 9.70E−11 | 0.146 | 0.145 |
| 74.9 | 6.9966 | 3.42 | 3.89 | 9.58E−11 | 0.181 | 0.180 |
| 75.0 | 8.4958 | 4.28 | 4.77 | 9.56E−11 | 0.215 | 0.212 |
| 75.0 | 9.9989 | 5.12 | 5.62 | 1.18E−10 | 0.245 | 0.244 |

EXAMPLE 4

Solubility of pentafluoroethane (HFC-125) in 1-butyl-3-methylimidazolium hexafluorophosphate A solubility and diffusivity study was made at temperatures of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 5a, 5b, 5c and 5d provide data for $C_o$, $C_s$, D, $X_{calc}$, and $X_{meas}$ at temperatures of 10, 25, 50 and 75° C., respectively.

TABLE 5a

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 9.9 | 0.0992 | 0.0 | 0.12 | 2.52E−12 | 0.003 | 0.013 |
| 10.0 | 0.9964 | 0.73 | 1.50 | 1.83E−11 | 0.035 | 0.034 |
| 10.1 | 1.9959 | 1.72 | 3.96 | 6.36E−12 | 0.089 | 0.074 |
| 10.0 | 2.9960 | 3.55 | 6.25 | 9.31E−12 | 0.136 | 0.125 |
| 10.1 | 3.9964 | 6.03 | 8.88 | 1.56E−11 | 0.187 | 0.182 |
| 9.9 | 4.9965 | 9.10 | 12.52 | 2.44E−11 | 0.253 | 0.250 |
| 10.0 | 5.9965 | 13.18 | 17.56 | 4.05E−11 | 0.335 | 0.336 |
| 9.9 | 6.9962 | 19.19 | 26.04 | 6.12E−11 | 0.455 | 0.454 |
| 10.0 | 7.9979 | — | — | — | — | 0.651 |

TABLE 5b

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0977 | 0.0 | 0.09 | 3.29E−12 | 0.002 | 0.003 |
| 25.0 | 0.9963 | 0.23 | 0.09 | 1.81E−11 | 0.002 | 0.023 |
| 25.0 | 1.9982 | 1.05 | 2.12 | 1.50E−11 | 0.049 | 0.050 |
| 24.9 | 2.9949 | 2.13 | 3.11 | 2.15E−11 | 0.071 | 0.079 |
| 25.0 | 3.9982 | 3.50 | 4.71 | 2.03E−11 | 0.105 | 0.109 |
| 25.0 | 4.9947 | 4.84 | 6.18 | 2.39E−11 | 0.135 | 0.140 |
| 25.0 | 5.9951 | 6.38 | 7.91 | 2.65E−11 | 0.169 | 0.176 |
| 25.0 | 7.9955 | 8.96 | 12.10 | 4.81E−11 | 0.246 | 0.254 |
| 24.9 | 9.9977 | 14.20 | 18.16 | 7.82E−11 | 0.344 | 0.352 |

TABLE 5c

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 49.9 | 0.1003 | 0.0 | 0.02 | 1.96E−10 | 0.000 | 0.000 |
| 49.9 | 0.9963 | 0.18 | 0.55 | 4.29E−11 | 0.013 | 0.013 |
| 49.9 | 1.9983 | 0.73 | 1.17 | 4.59E−11 | 0.027 | 0.027 |
| 50.0 | 2.9996 | 1.34 | 1.78 | 5.19E−11 | 0.041 | 0.041 |
| 49.9 | 3.9969 | 1.96 | 2.44 | 4.75E−11 | 0.056 | 0.056 |
| 50.0 | 4.9993 | 2.60 | 3.10 | 5.38E−11 | 0.070 | 0.070 |
| 49.9 | 5.9961 | 3.29 | 3.80 | 5.14E−11 | 0.086 | 0.085 |
| 49.9 | 7.9970 | 4.38 | 5.25 | 5.55E−11 | 0.116 | 0.116 |
| 49.9 | 9.9958 | 5.85 | 6.82 | 5.87E−11 | 0.148 | 0.148 |

TABLE 5d

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 75.0 | 0.1021 | 0.0 | 0.03 | 6.85E−11 | 0.001 | 0.001 |
| 74.9 | 0.9965 | 0.07 | 0.28 | 7.49E−11 | 0.007 | 0.007 |
| 75.0 | 1.9961 | 0.36 | 0.60 | 9.46E−11 | 0.014 | 0.016 |
| 75.1 | 2.9967 | 0.70 | 0.93 | 7.04E−11 | 0.022 | 0.025 |
| 75.0 | 3.9971 | 1.04 | 1.27 | 7.96E−11 | 0.030 | 0.033 |
| 75.0 | 4.9983 | 1.36 | 1.61 | 9.86E−11 | 0.037 | 0.042 |
| 75.0 | 5.9980 | 1.75 | 1.97 | 7.12E−11 | 0.045 | 0.052 |
| 75.1 | 7.9997 | 2.26 | 2.65 | 1.14E−10 | 0.061 | 0.068 |
| 75.0 | 9.9959 | 3.00 | 3.33 | 8.89E−11 | 0.075 | 0.085 |

EXAMPLE 5

Solubility of 1,1,1,2-tetrafluoroethane (HFC-134a) in 1-butyl-3-methylimidazolium hexafluorophosphate A solubility and diffusivity study was made at temperatures of 10, 25, 50, and 75° C. over a pressure range from 0 to 3.5 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 6a, 6b, 6c and 6d provide data for $C_o$, $C_s$, D, $X_{calc}$, and $X_{meas}$ at temperatures of 10, 25, 50 and 75° C., respectively.

TABLE 6a

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 9.8 | 0.0999 | 0.0 | 0.23 | 4.21E−12 | 0.006 | 0.003 |
| 10.0 | 0.4981 | 0.35 | 2.20 | 6.46E−12 | 0.059 | 0.050 |
| 9.9 | 0.9986 | 2.25 | 5.73 | 5.78E−12 | 0.145 | 0.126 |
| 9.9 | 1.4981 | 5.40 | 9.15 | 1.01E−11 | 0.219 | 0.212 |
| 9.9 | 2.0024 | 9.50 | 13.64 | 1.48E−11 | 0.306 | 0.303 |
| 9.9 | 2.4907 | 14.39 | 19.36 | 2.67E−11 | 0.401 | 0.402 |
| 9.9 | 2.9974 | 20.96 | 27.51 | 5.33E−11 | 0.514 | 0.516 |
| 9.9 | 3.4900 | — | — | — | — | 0.721 |

TABLE 6b

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 25.0 | 0.1002 | 0.17 | 0.29 | 4.36E−12 | 0.008 | 0.011 |
| 24.9 | 0.4981 | 0.57 | 1.52 | 1.89E−11 | 0.041 | 0.042 |
| 25.0 | 0.9972 | 1.82 | 3.26 | 1.71E−11 | 0.086 | 0.085 |
| 25.0 | 1.4987 | 3.60 | 5.09 | 2.00E−11 | 0.130 | 0.130 |
| 25.0 | 1.9930 | 5.43 | 7.09 | 2.27E−11 | 0.175 | 0.175 |
| 24.9 | 2.4996 | 7.53 | 9.31 | 2.59E−11 | 0.222 | 0.222 |
| 25.0 | 2.9952 | 9.78 | 11.82 | 2.82E−11 | 0.272 | 0.273 |
| 24.9 | 3.5000 | 12.51 | 14.62 | 3.99E−11 | 0.323 | 0.323 |

TABLE 6c

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 49.9 | 0.0992 | 0.07 | 0.13 | 2.44E−11 | 0.004 | 0.004 |
| 50.0 | 0.4984 | 0.25 | 0.75 | 4.39E−11 | 0.021 | 0.021 |
| 49.9 | 0.9971 | 1.00 | 1.57 | 3.94E−11 | 0.043 | 0.043 |
| 49.9 | 1.4989 | 1.79 | 2.42 | 4.48E−11 | 0.064 | 0.065 |
| 50.0 | 1.9895 | 2.65 | 3.28 | 4.38E−11 | 0.086 | 0.086 |
| 50.0 | 2.4900 | 3.75 | 4.23 | 2.33E−11 | 0.110 | 0.108 |
| 50.0 | 2.9897 | 4.43 | 5.10 | 4.90E−11 | 0.130 | 0.130 |
| 50.0 | 3.4933 | 5.39 | 6.06 | 5.00E−11 | 0.152 | 0.152 |

TABLE 6d

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 75.0 | 0.0970 | 0.00 | 0.03 | 6.45E−11 | 0.001 | 0.001 |
| 74.9 | 0.4984 | 0.09 | 0.32 | 7.49E−11 | 0.009 | 0.009 |
| 74.9 | 0.9934 | 0.51 | 0.79 | 7.93E−11 | 0.022 | 0.022 |
| 74.9 | 1.5010 | 0.98 | 1.27 | 7.78E−11 | 0.035 | 0.035 |

TABLE 6d-continued

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 75.0 | 1.9983 | 1.44 | 1.73 | 8.37E−11 | 0.047 | 0.046 |
| 75.0 | 2.5014 | 1.89 | 2.21 | 8.37E−11 | 0.059 | 0.059 |
| 75.0 | 3.0022 | 2.39 | 2.71 | 8.26E−11 | 0.072 | 0.072 |
| 75.0 | 3.4897 | 2.95 | 3.21 | 5.53E−11 | 0.085 | 0.084 |

EXAMPLE 6

Solubility of 1,1,1-trifluoroethane (HFC-143a) in 1-butyl-3-methylimidazolium hexafluorophosphate A solubility and diffusivity study was made at temperatures of 10, 25, 50, and 75° C. over a pressure range from 0 to 7.5 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 7a, 7b, 7c and 7d provide data for $C_o$, $C_s$, D, $X_{calc}$, and $X_{meas}$ at temperatures of 10, 25, 50 and 75° C., respectively.

TABLE 7a

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 11.7 | 0.0956 | 0.03 | 0.10 | 8.10E−12 | 0.003 | 0.003 |
| 12.0 | 0.9970 | 0.22 | 0.92 | 8.51E−12 | 0.031 | 0.029 |
| 11.9 | 1.9830 | 0.99 | 1.93 | 8.11E−12 | 0.064 | 0.060 |
| 12.0 | 2.9740 | 1.95 | 2.39 | 3.21E−12 | 0.078 | 0.093 |
| 12.3 | 3.9808 | 3.06 | 4.03 | 1.04E−11 | 0.127 | 0.124 |
| 12.0 | 4.9975 | 4.16 | 5.23 | 1.10E−11 | 0.161 | 0.156 |
| 12.0 | 5.9821 | 5.30 | 6.42 | 1.44E−11 | 0.192 | 0.188 |
| 12.2 | 6.9975 | 6.54 | 7.63 | 1.94E−11 | 0.223 | 0.219 |
| 12.2 | 7.4832 | 7.80 | 8.31 | 2.03E−11 | 0.239 | 0.235 |

TABLE 7b

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 25.0 | 0.0951 | 0.00 | 0.01 | 1.53E−11 | 0.001 | 0.004 |
| 24.9 | 0.9970 | 0.24 | 0.69 | 2.05E−11 | 0.023 | 0.023 |
| 24.9 | 2.0054 | 0.84 | 1.33 | 2.56E−11 | 0.045 | 0.042 |
| 24.9 | 2.9895 | 1.40 | 2.10 | 1.83E−11 | 0.069 | 0.068 |
| 24.9 | 4.0147 | 2.26 | 2.89 | 1.77E−11 | 0.093 | 0.090 |
| 24.9 | 4.9886 | 2.95 | 3.60 | 2.24E−11 | 0.114 | 0.112 |
| 24.9 | 5.9855 | 3.71 | 4.33 | 2.73E−11 | 0.136 | 0.134 |
| 24.9 | 7.0019 | 4.47 | 5.12 | 2.83E−11 | 0.157 | 0.155 |
| 24.9 | 7.5011 | 5.14 | 5.53 | 3.61E−11 | 0.169 | 0.165 |

TABLE 7c

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 49.9 | 0.1050 | 0.00 | 0.03 | 1.51E−10 | 0.000 | 0.001 |
| 49.9 | 1.0023 | 0.16 | 0.40 | 4.47E−11 | 0.014 | 0.013 |
| 50.1 | 2.0045 | 0.61 | 0.84 | 3.41E−11 | 0.028 | 0.027 |
| 50.0 | 3.0002 | 1.03 | 1.26 | 2.90E−11 | 0.042 | 0.040 |
| 50.0 | 4.0021 | 1.39 | 1.65 | 5.08E−11 | 0.055 | 0.054 |
| 50.0 | 5.0046 | 1.81 | 2.08 | 4.10E−11 | 0.069 | 0.067 |
| 50.0 | 6.0039 | 2.29 | 2.50 | 3.75E−11 | 0.082 | 0.079 |
| 50.0 | 7.0029 | 2.63 | 2.90 | 5.57E−11 | 0.094 | 0.092 |
| 50.0 | 10.0030 | 3.56 | 4.16 | 5.51E−11 | 0.131 | 0.127 |

TABLE 7d

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 75.0 | 0.0995 | 0.00 | 0.01 | 3.86E−12 | 0.000 | 0.001 |
| 74.9 | 1.0005 | 0.18 | 0.26 | 7.38E−11 | 0.009 | 0.009 |
| 74.8 | 1.9960 | 0.38 | 0.54 | 1.04E−10 | 0.018 | 0.018 |
| 74.9 | 3.0001 | 0.67 | 0.81 | 1.07E−10 | 0.028 | 0.027 |
| 74.9 | 4.0015 | 0.91 | 1.08 | 1.32E−10 | 0.037 | 0.036 |
| 74.9 | 5.0027 | 1.18 | 1.36 | 1.20E−10 | 0.045 | 0.044 |
| 75.0 | 5.9979 | 1.44 | 1.63 | 1.40E−10 | 0.054 | 0.053 |
| 75.0 | 7.0026 | 1.92 | 1.94 | 3.79E−09 | 0.064 | 0.061 |
| 74.9 | 10.0035 | 2.65 | 2.76 | 1.90E−09 | 0.089 | 0.083 |

EXAMPLE 7

Solubility of 1,1-difluoroethane (HFC-152a) in 1-butyl-3-methylimidazolium hexafluorophosphate A solubility and diffusivity study was made at temperatures of 10, 25, 50, and 75° C. over a pressure range from 0 to 4.5 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 8a, 8b, 8c and 8d provide data for $C_o$, $C_s$, D, $X_{calc}$, and $X_{meas}$ at temperatures of 10, 25, 50 and 75° C., respectively.

TABLE 8a

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 10.0 | 0.0973 | 0.10 | 0.73 | 2.13E−12 | 0.031 | 0.021 |
| 10.0 | 0.4994 | 1.23 | 2.90 | 1.14E−11 | 0.114 | 0.103 |
| 10.0 | 0.9933 | 3.58 | 6.11 | 1.56E−11 | 0.219 | 0.210 |
| 10.0 | 1.4985 | 6.91 | 9.60 | 3.09E−11 | 0.314 | 0.301 |
| 9.9 | 2.0011 | 10.40 | 14.00 | 3.60E−11 | 0.412 | 0.407 |
| 9.9 | 2.4952 | 15.52 | 20.42 | 6.44E−11 | 0.525 | 0.521 |
| 9.9 | 3.1963 | — | — | — | — | 0.797 |

TABLE 8b

| T (° C.) | P (bar) | $C_o$ (mass %) | $C_s$ (mass %) | D ($m^2$/sec) | $X_{calc.}$ (mol. fraction) | $X_{meas.}$ (mol. fraction) |
|---|---|---|---|---|---|---|
| 25.0 | 0.1002 | 0.16 | 0.66 | 2.00E−11 | 0.028 | 0.030 |
| 25.0 | 0.5006 | 1.02 | 1.92 | 2.01E−11 | 0.078 | 0.077 |
| 24.9 | 0.9982 | 2.34 | 3.55 | 2.64E−11 | 0.137 | 0.136 |
| 25.0 | 1.4924 | 4.20 | 5.35 | 2.89E−11 | 0.196 | 0.194 |
| 25.0 | 2.4969 | 6.74 | 9.52 | 4.96E−11 | 0.312 | 0.311 |
| 25.0 | 3.4818 | 11.59 | 15.05 | 7.73E−11 | 0.433 | 0.432 |
| 25.0 | 4.5051 | 18.83 | 23.81 | 1.04E−10 | 0.573 | 0.574 |

TABLE 8c

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 50.1 | 0.9921 | 0.03 | 0.15 | 5.73E−11 | 0.007 | 0.007 |
| 50.0 | 1.0017 | 0.88 | 1.46 | 5.52E−11 | 0.060 | 0.060 |
| 50.0 | 1.5020 | 1.63 | 2.22 | 5.94E−11 | 0.089 | 0.089 |
| 50.0 | 2.4969 | 2.72 | 3.81 | 6.43E−11 | 0.145 | 0.145 |
| 50.0 | 4.5051 | 6.31 | 7.33 | 7.88E−11 | 0.254 | 0.254 |

TABLE 8d

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 74.9 | 0.1032 | 0.04 | 0.11 | 1.38E−10 | 0.005 | 0.005 |
| 74.9 | 0.5019 | 0.19 | 0.42 | 1.25E−10 | 0.018 | 0.018 |
| 74.9 | 1.0023 | 0.57 | 0.84 | 1.21E−10 | 0.035 | 0.035 |
| 74.9 | 1.5014 | 0.99 | 1.27 | 1.25E−10 | 0.052 | 0.052 |
| 75.0 | 2.4964 | 1.63 | 2.12 | 1.42E−10 | 0.085 | 0.085 |
| 75.0 | 3.4970 | 2.57 | 2.98 | 1.48E−10 | 0.117 | 0.117 |
| 74.8 | 4.5003 | 3.51 | 3.89 | 1.21E−10 | 0.148 | 0.149 |

EXAMPLE 8

Solubility of difluoromethane (HFC-32) in 1-butyl-3-methylimidazolium tetrafluoroborate A solubility and diffusivity study was made at temperatures of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 9a, 9b, 9c and 9d provide data for $C_o$, $C_s$, D, $X_{calc}$, and $X_{meas}$ at temperatures of 10, 25, 50 and 75° C., respectively.

TABLE 9a

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 9.9 | 0.1002 | 8.35 | 9.20 | 1.76E−11 | 0.008 | 0.009 |
| 9.9 | 0.9985 | 10.08 | 13.74 | 1.72E−11 | 0.100 | 0.108 |
| 10.0 | 2.4995 | 15.10 | 18.94 | 3.29E−11 | 0.239 | 0.254 |
| 10.0 | 3.9954 | 21.28 | 25.08 | 4.53E−11 | 0.376 | 0.396 |
| 9.8 | 5.4992 | 28.16 | 33.17 | 8.48E−11 | 0.499 | 0.519 |
| 9.9 | 6.9988 | 37.79 | 46.86 | 1.08E−10 | 0.625 | 0.636 |
| 9.9 | 8.4966 | 52.61 | 52.61 | 1.01E−10 | 0.766 | 0.765 |

TABLE 9b

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0969 | 0.01 | 0.15 | 3.37E−11 | 0.007 | 0.006 |
| 25.0 | 0.9968 | 0.59 | 1.81 | 3.36E−11 | 0.074 | 0.070 |
| 25.0 | 2.4955 | 2.75 | 4.79 | 3.70E−11 | 0.180 | 0.174 |
| 25.0 | 3.9989 | 5.87 | 7.95 | 4.62E−11 | 0.273 | 0.270 |
| 25.0 | 5.4977 | 9.23 | 11.36 | 5.98E−11 | 0.358 | 0.356 |
| 25.0 | 6.9955 | 12.90 | 15.12 | 7.44E−11 | 0.436 | 0.434 |
| 25.0 | 8.4945 | 17.08 | 19.33 | 9.10E−11 | 0.510 | 0.510 |
| 25.0 | 9.9985 | 21.83 | 24.46 | 9.94E−11 | 0.585 | 0.583 |

TABLE 9c

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 50.0 | 0.0977 | 0.01 | 0.07 | 8.71E−11 | 0.003 | 0.003 |
| 49.9 | 0.9961 | 0.37 | 0.95 | 7.56E−11 | 0.040 | 0.039 |
| 50.0 | 2.4967 | 1.67 | 2.47 | 7.40E−11 | 0.099 | 0.099 |
| 50.0 | 3.9964 | 3.16 | 4.01 | 8.23E−11 | 0.154 | 0.153 |
| 49.9 | 5.4956 | 4.75 | 5.59 | 8.95E−11 | 0.205 | 0.204 |
| 49.9 | 6.9953 | 6.38 | 7.22 | 9.88E−11 | 0.253 | 0.253 |
| 49.8 | 8.4986 | 8.05 | 8.91 | 1.06E−10 | 0.298 | 0.298 |
| 50.0 | 9.9963 | 9.75 | 10.64 | 1.11E−10 | 0.341 | 0.341 |

TABLE 9d

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 75.0 | 0.0971 | 0.0 | 0.03 | 1.26E−10 | 0.001 | 0.001 |
| 74.9 | 0.9956 | 0.26 | 0.54 | 1.28E−10 | 0.023 | 0.023 |
| 74.9 | 2.4948 | 1.03 | 1.40 | 1.25E−10 | 0.058 | 0.058 |
| 75.0 | 3.9950 | 1.92 | 2.27 | 1.22E−10 | 0.092 | 0.091 |
| 74.9 | 5.4951 | 2.75 | 3.14 | 1.45E−10 | 0.124 | 0.123 |
| 75.0 | 6.9955 | 3.64 | 4.03 | 1.59E−10 | 0.154 | 0.154 |
| 74.9 | 8.4964 | 4.54 | 4.94 | 1.42E−10 | 0.184 | 0.183 |
| 74.9 | 9.9994 | 5.44 | 5.82 | 1.89E−10 | 0.212 | 0.212 |

EXAMPLE 9

Solubility of difluoromethane (HFC-32) in 1,2-dimethyl-3-propylimidazolium tris(trifluoromethylsulfonyl)methide A solubility and diffusivity study was made at temperatures of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 10a, 10b, 10c and 10d provide data for $C_o$, $C_s$, D, $X_{calc}$, and $X_{meas}$ at temperatures of 10, 25, 50 and 75° C., respectively.

TABLE 10a

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 10.0 | 0.1010 | 0.03 | 0.11 | 1.71E−11 | 0.012 | 0.012 |
| 10.0 | 0.9964 | 0.43 | 1.44 | 1.39E−11 | 0.134 | 0.136 |
| 10.0 | 2.4970 | 2.39 | 4.13 | 2.52E−11 | 0.313 | 0.311 |
| 10.0 | 3.9969 | 5.57 | 7.39 | 5.04E−11 | 0.458 | 0.457 |
| 10.0 | 5.4947 | 9.70 | 11.67 | 8.93E−11 | 0.583 | 0.583 |
| 10.0 | 6.9966 | 15.43 | 17.70 | 1.37E−10 | 0.695 | 0.696 |
| 10.0 | 8.4959 | 24.33 | 28.09 | 1.56E−10 | 0.805 | 0.802 |

TABLE 10b

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 24.9 | 0.0998 | 0.01 | 0.09 | 2.71E−11 | 0.010 | 0.010 |
| 24.9 | 0.9997 | 0.42 | 1.01 | 2.52E−11 | 0.098 | 0.096 |
| 24.9 | 2.4956 | — | — | — | — | 0.225 |
| 24.9 | 3.9958 | 3.61 | 4.55 | 5.46E−11 | 0.336 | 0.335 |

TABLE 10b-continued

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 24.9 | 5.4927 | 5.76 | 6.69 | 7.98E−11 | 0.432 | 0.431 |
| 24.9 | 6.9955 | 8.15 | 9.13 | 1.10E−10 | 0.516 | 0.515 |
| 24.9 | 8.4948 | 11.02 | 12.07 | 1.34E−10 | 0.593 | 0.593 |
| 24.9 | 10.0000 | 14.52 | 15.59 | 1.83E−10 | 0.662 | 0.662 |

TABLE 10c

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 50.0 | 0.0991 | 0.21 | 0.04 | 6.45E−11 | 0.004 | 0.004 |
| 50.0 | 0.9995 | 0.29 | 0.57 | 6.75E−11 | 0.058 | 0.057 |
| 50.0 | 2.4945 | 1.11 | 1.52 | 7.87E−11 | 0.141 | 0.141 |
| 50.0 | 3.9947 | 2.10 | 2.50 | 9.56E−11 | 0.213 | 0.213 |
| 50.0 | 5.4954 | 3.15 | 3.51 | 1.15E−10 | 0.278 | 0.278 |
| 50.0 | 6.9968 | 4.24 | 4.59 | 1.33E−10 | 0.338 | 0.338 |
| 50.0 | 8.4944 | 5.37 | 5.73 | 1.51E−10 | 0.392 | 0.392 |
| 50.0 | 9.9952 | 6.61 | 6.96 | 1.68E−10 | 0.442 | 0.442 |

TABLE 10d

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 75.0 | 0.0940 | 0.0 | 0.0 | 5.75E−11 | 0.000 | 0.000 |
| 74.9 | 1.0018 | 0.06 | 0.31 | 6.06E−11 | 0.032 | 0.031 |
| 75.0 | 2.5040 | 0.71 | 0.89 | 1.23E−10 | 0.087 | 0.087 |
| 74.9 | 3.9958 | 1.32 | 1.49 | 1.26E−10 | 0.138 | 0.138 |
| 74.9 | 5.4938 | 1.92 | 2.09 | 1.59E−10 | 0.184 | 0.184 |
| 74.9 | 7.0051 | 2.58 | 2.72 | 1.35E−10 | 0.229 | 0.229 |
| 74.9 | 8.4954 | 3.24 | 3.37 | 1.19E−10 | 0.270 | 0.268 |
| 74.9 | 10.0046 | 3.89 | 4.05 | 2.10E−10 | 0.309 | 0.308 |

EXAMPLE 10

Solubility of difluoromethane (HFC-32) in 1-octyl-3-methylimidazolium iodide

A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Table 11 provides data for $C_o$, $C_s$, D, $X_{calc}$, and $X_{meas}$ at a temperature of 25° C.

TABLE 11

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.1007 | 0.01 | 0.06 | 1.75E−11 | 0.004 | 0.004 |
| 25.2 | 1.0021 | 0.23 | 0.80 | 1.77E−11 | 0.048 | 0.048 |
| 25.0 | 2.4971 | 1.20 | 2.13 | 1.86E−11 | 0.119 | 0.118 |
| 25.0 | 3.9999 | 2.58 | 3.55 | 2.27E−11 | 0.186 | 0.185 |
| 25.0 | 5.5008 | 4.07 | 5.04 | 3.13E−11 | 0.247 | 0.246 |
| 25.0 | 6.9964 | 5.64 | 6.64 | 3.81E−11 | 0.306 | 0.306 |
| 25.0 | 8.5027 | 7.52 | 8.33 | 2.86E−11 | 0.360 | 0.362 |
| 25.0 | 10.0022 | 9.27 | 10.35 | 6.37E−11 | 0.417 | 0.416 |

EXAMPLE 11

Solubility of difluoromethane (HFC-32) in 1,3-dioctylimidazolium iodide

A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Table 12 provides data for $C_o$, $C_s$, D, $X_{calc}$, and $X_{means}$ at a temperature of 25° C.

TABLE 12

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.1002 | 0.03 | 0.11 | 1.78E−11 | 0.009 | 0.007 |
| 25.0 | 1.0010 | 0.29 | 0.87 | 2.11E−11 | 0.066 | 0.064 |
| 25.0 | 2.5003 | 1.29 | 2.17 | 2.35E−11 | 0.152 | 0.150 |
| 25.0 | 4.0024 | 2.62 | 3.51 | 2.91E−11 | 0.227 | 0.225 |
| 25.0 | 5.5024 | 4.03 | 4.93 | 3.54E−11 | 0.295 | 0.293 |
| 25.0 | 7.0010 | 5.51 | 6.43 | 4.25E−11 | 0.357 | 0.355 |
| 24.9 | 8.4988 | 7.12 | 8.07 | 5.00E−11 | 0.415 | 0.413 |
| 25.0 | 10.0024 | 8.83 | 9.85 | 5.77E−11 | 0.469 | 0.468 |

EXAMPLE 12

Solubility of difluoromethane (HFC-32) in 1-ethyl-3-methylimidazolium bis(pentafluoroethylsulfonyl)imide A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 13a, 13b, 13c and 13d provide data for $C_o$, $C_s$, D, $X_{calc}$, and $X_{meas}$ at a temperature of 10° C., 25° C., 50° C., and 75° C., respectively.

TABLE 13a

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 10.0 | 0.101 | 0.06 | 0.15 | 3.79E−11 | 0.014 | 0.014 |
| 10.0 | 1.000 | 1.06 | 1.78 | 4.78E−11 | 0.146 | 0.144 |
| 10.0 | 2.495 | 3.58 | 4.83 | 7.37E−11 | 0.324 | 0.323 |
| 10.0 | 3.995 | 7.14 | 8.52 | 1.17E−10 | 0.468 | 0.467 |
| 10.0 | 5.496 | 11.75 | 13.23 | 1.51E−10 | 0.590 | 0.590 |
| 10.0 | 6.994 | 17.76 | 19.75 | 1.72E−10 | 0.699 | 0.699 |
| 10.0 | 8.505 | 26.95 | 30.37 | 1.67E−10 | 0.805 | 0.799 |

TABLE 13b

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.096 | 0.03 | 0.11 | 7.5E−11 | 0.010 | 0.010 |
| 25.0 | 0.997 | 0.71 | 1.22 | 7.9E−11 | 0.104 | 0.104 |

TABLE 13b-continued

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 2.496 | 2.49 | 3.19 | 1.1E−10 | 0.237 | 0.237 |
| 25.0 | 3.996 | 4.61 | 5.33 | 1.3E−10 | 0.347 | 0.347 |
| 25.0 | 5.493 | 7.03 | 7.75 | 1.6E−10 | 0.443 | 0.442 |
| 25.0 | 6.993 | 9.70 | 10.49 | 1.8E−10 | 0.525 | 0.525 |
| 25.0 | 8.503 | 12.87 | 13.71 | 2.1E−10 | 0.600 | 0.598 |
| 25.0 | 10.005 | 16.49 | 17.56 | 1.7E−10 | 0.668 | 0.666 |

TABLE 13c

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 50.0 | 0.100 | 0.00 | 0.04 | 1.66E−10 | 0.004 | 0.004 |
| 50.0 | 0.997 | 0.49 | 0.65 | 1.34E−10 | 0.058 | 0.059 |
| 50.0 | 2.497 | 1.46 | 1.73 | 1.79E−10 | 0.142 | 0.145 |
| 50.0 | 3.996 | 2.61 | 2.83 | 1.92E−10 | 0.216 | 0.219 |
| 50.0 | 5.495 | 3.82 | 3.98 | 2.19E−10 | 0.281 | 0.285 |
| 50.0 | 6.995 | 4.92 | 5.19 | 2.28E−10 | 0.341 | 0.345 |
| 50.0 | 8.504 | 6.20 | 6.46 | 2.73E−10 | 0.395 | 0.399 |
| 50.0 | 9.993 | 7.54 | 7.81 | 1.62E−10 | 0.444 | 0.449 |

TABLE 13d

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 74.9 | 0.101 | 0.00 | 0.01 | 3.92E−10 | 0.001 | 0.001 |
| 74.9 | 1.000 | 0.32 | 0.41 | 2.60E−10 | 0.038 | 0.038 |
| 74.9 | 2.501 | 0.99 | 1.10 | 3.32E−10 | 0.095 | 0.095 |
| 74.9 | 3.992 | 1.72 | 1.79 | 3.96E−10 | 0.147 | 0.146 |
| 74.9 | 5.496 | 2.39 | 2.49 | 3.53E−10 | 0.194 | 0.194 |
| 74.9 | 6.996 | 3.08 | 3.22 | 3.41E−10 | 0.239 | 0.239 |
| 74.9 | 8.504 | 3.87 | 3.96 | 3.48E−10 | 0.280 | 0.280 |
| 74.9 | 9.994 | 4.55 | 4.70 | 1.92E−10 | 0.318 | 0.317 |

EXAMPLE 13

Solubility of difluoromethane (HFC-32) in 1,2-dimethyl-3-propylimidazolium bis(trifluoromethylsulfonyl)imide A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Table 14 provides data for $C_o$, $C_s$, D, $X_{calc}$, and $X_{meas}$ at a temperature of 25° C.

TABLE 14

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 24.9 | 0.0989 | 0.02 | 0.11 | 6.31E−11 | 0.008 | 0.008 |
| 25.0 | 0.9951 | 0.65 | 1.22 | 6.60E−11 | 0.091 | 0.090 |
| 25.0 | 2.4949 | 2.44 | 3.25 | 8.94E−11 | 0.213 | 0.212 |
| 25.0 | 3.9762 | 4.62 | 5.46 | 1.21E−10 | 0.317 | 0.317 |
| 25.0 | 5.5013 | 7.08 | 8.00 | 1.46E−10 | 0.412 | 0.412 |
| 25.0 | 7.0174 | 10.02 | 10.92 | 1.75E−10 | 0.497 | 0.496 |
| 25.0 | 8.5131 | 13.56 | 14.29 | 2.23E−10 | 0.573 | 0.573 |
| 25.0 | 10.0108 | 17.55 | 18.41 | 2.33E−10 | 0.645 | 0.645 |

EXAMPLE 14

Solubility of difluoromethane (HFC-32) in 3-methyl-1-propylpyridinium bis(trifluoromethylsulfonyl)imide A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 15a, 15b, 15c, and 15d provide data for $C_o$, $C_s$, D, $X_{calc}$, and $X_{meas}$ at a temperature of 10° C., 25° C., 50° C., and 75° C., respectively.

TABLE 15a

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 10.0 | 0.1021 | 0.08 | 0.02 | 5.76E−11 | 0.002 | 0.015 |
| 10.0 | 1.0001 | 1.03 | 2.01 | 5.72E−11 | 0.141 | 0.140 |
| 10.0 | 2.4942 | 3.95 | 5.31 | 1.05E−10 | 0.310 | 0.311 |
| 10.0 | 3.9963 | 7.78 | 9.35 | 1.28E−10 | 0.452 | 0.452 |
| 10.0 | 5.4935 | 12.68 | 14.05 | 2.89E−10 | 0.567 | 0.570 |
| 10.0 | 6.9960 | 18.73 | 20.79 | 2.01E−10 | 0.678 | 0.679 |
| 10.0 | 8.4951 | 27.80 | 30.88 | 2.71E−10 | 0.781 | 0.778 |

TABLE 15b

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 24.9 | 0.0951 | 0.02 | 0.12 | 9.96E−11 | 0.010 | 0.010 |
| 24.9 | 1.0020 | 0.74 | 1.32 | 1.00E−10 | 0.097 | 0.096 |
| 24.9 | 2.5034 | 2.67 | 3.44 | 1.20E−10 | 0.222 | 0.221 |
| 24.9 | 3.9959 | 4.93 | 5.73 | 1.52E−10 | 0.327 | 0.328 |
| 24.9 | 5.4973 | 7.52 | 8.30 | 1.92E−10 | 0.420 | 0.419 |
| 24.9 | 6.9923 | 10.35 | 11.16 | 2.20E−10 | 0.501 | 0.502 |
| 24.9 | 8.4965 | 13.61 | 14.48 | 2.41E−10 | 0.575 | 0.575 |
| 24.9 | 10.0044 | 17.35 | 18.06 | 6.21E−10 | 0.638 | 0.639 |

TABLE 15c

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 50.0 | 0.1025 | 0.04 | 0.08 | 2.10E−10 | 0.007 | 0.007 |
| 50.0 | 1.0031 | 0.59 | 0.76 | 1.86E−10 | 0.058 | 0.058 |
| 50.0 | 2.4979 | 1.64 | 1.93 | 2.01E−10 | 0.136 | 0.137 |
| 50.0 | 4.0004 | 2.82 | 3.11 | 2.80E−10 | 0.205 | 0.206 |
| 50.0 | 5.4945 | 4.05 | 4.36 | 2.37E−10 | 0.268 | 0.270 |
| 50.0 | 6.9935 | 5.39 | 5.64 | 3.50E−10 | 0.323 | 0.326 |
| 50.0 | 8.5031 | 6.71 | 6.97 | 3.95E−10 | 0.375 | 0.378 |
| 50.0 | 9.9939 | 8.06 | 8.44 | 2.30E−10 | 0.425 | 0.427 |

TABLE 15d

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 74.9 | 0.1026 | 0.03 | 0.04 | 3.94E-10 | 0.003 | 0.003 |
| 74.9 | 1.0023 | 0.04 | 0.46 | 3.89E-10 | 0.036 | 0.037 |
| 74.9 | 2.5020 | 1.06 | 1.19 | 3.96E-10 | 0.088 | 0.089 |
| 74.9 | 4.0021 | 1.77 | 1.91 | 4.00E-10 | 0.135 | 0.138 |
| 74.9 | 5.4931 | 2.53 | 2.65 | 3.62E-10 | 0.179 | 0.183 |
| 74.9 | 7.0026 | 3.27 | 3.39 | 4.62E-10 | 0.219 | 0.223 |
| 74.9 | 8.4935 | 4.04 | 4.15 | 4.76E-10 | 0.257 | 0.262 |
| 74.9 | 10.0019 | 4.76 | 4.91 | 5.48E-10 | 0.293 | 0.300 |

EXAMPLE 15

Solubility of trifluoromethane (HFC-23) in 1-butyl-3-methylimidazolium hexafluorophosphate A solubility and diffusivity study was made at a temperature of 10, 25, 50, and 75° C. over a pressure range from 0 to 20 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 16a, 16b, 16c, and 16d provide data for $C_o$, $C_s$, D, $X_{calc}$, and $X_{meas}$ at a temperature of 10° C., 25° C., 50° C., and 75° C., respectively.

TABLE 16a

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 9.4 | 0.0962 | — | — | — | — | 0.000 |
| 9.4 | 0.5000 | 0.00 | 0.25 | 1.54E-11 | 0.010 | 0.010 |
| 9.6 | 1.0979 | — | — | — | — | 0.028 |
| 9.5 | 4.0003 | 1.56 | 3.05 | 1.54E-11 | 0.113 | 0.113 |
| 9.4 | 7.0000 | 4.14 | 5.76 | 2.17E-11 | 0.199 | 0.198 |
| 9.5 | 9.9934 | 7.15 | 8.81 | 2.89E-11 | 0.282 | 0.281 |
| 9.5 | 12.9972 | 10.59 | 12.22 | 4.26E-11 | 0.361 | 0.361 |
| 9.5 | 14.9964 | 13.48 | 14.81 | 5.68E-11 | 0.414 | 0.414 |
| 10.0 | 20.0017 | — | — | — | — | 0.528 |

TABLE 16b

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 24.9 | 0.0991 | — | — | — | — | 0.000 |
| 24.9 | 0.4972 | 0.03 | 0.19 | 2.56E-11 | 0.008 | 0.008 |
| 24.9 | 0.9994 | 0.24 | 0.44 | 3.22E-11 | 0.018 | 0.018 |
| 24.9 | 3.9934 | 1.17 | 2.08 | 2.37E-11 | 0.080 | 0.079 |
| 24.9 | 6.9953 | 2.86 | 3.79 | 3.01E-11 | 0.138 | 0.137 |
| 24.9 | 10.0041 | 4.68 | 5.59 | 3.95E-11 | 0.194 | 0.193 |
| 24.9 | 13.0056 | 6.66 | 7.52 | 3.89E-11 | 0.248 | 0.247 |
| 25.0 | 15.0000 | 8.09 | 8.80 | 5.73E-11 | 0.281 | 0.281 |
| 24.9 | 19.9990 | 11.36 | 12.49 | 7.12E-11 | 0.367 | 0.367 |

TABLE 16c

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 50.0 | 0.0981 | 0.00 | 0.01 | 6.34E-11 | 0.000 | 0.000 |
| 50.0 | 0.4984 | 0.03 | 0.11 | 6.26E-11 | 0.005 | 0.005 |
| 50.0 | 0.9961 | 0.17 | 0.27 | 7.35E-11 | 0.011 | 0.011 |
| 50.0 | 3.9965 | 0.89 | 1.27 | 5.88E-11 | 0.049 | 0.049 |
| 50.0 | 7.0036 | 1.90 | 2.25 | 6.74E-11 | 0.085 | 0.085 |
| 50.0 | 10.0041 | 2.92 | 3.27 | 8.02E-11 | 0.121 | 0.120 |
| 50.0 | 12.9931 | 3.95 | 4.29 | 7.47E-11 | 0.154 | 0.154 |
| 50.0 | 15.0015 | 4.69 | 5.01 | 1.16E-10 | 0.176 | 0.176 |
| 50.0 | 19.9932 | 6.41 | 6.78 | 1.08E-10 | 0.228 | 0.227 |

TABLE 16d

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 75.0 | 0.0965 | — | — | — | — | 0.001 |
| 74.9 | 0.4973 | 0.03 | 0.08 | 8.13E-11 | 0.003 | 0.003 |
| 74.9 | 0.9975 | 0.12 | 0.21 | 1.22E-10 | 0.008 | 0.008 |
| 74.9 | 3.9971 | 0.63 | 0.84 | 1.04E-10 | 0.033 | 0.033 |
| 74.9 | 7.0016 | 1.45 | 1.42 | 2.86E-12 | 0.055 | 0.057 |
| 75.0 | 9.9934 | 1.92 | 2.08 | 1.08E-10 | 0.079 | 0.080 |
| 74.9 | 13.0031 | 2.55 | 2.72 | 2.23E-10 | 0.102 | 0.103 |
| 74.9 | 14.9943 | 2.98 | 3.17 | 1.09E-10 | 0.117 | 0.118 |
| 74.9 | 19.9998 | 4.00 | 4.22 | 2.31E-10 | 0.152 | 0.146 |

EXAMPLE 16

Solubility of trifluoromethane (HFC-23) in 1-ethyl-3-methylimidazolium hexafluorophosphate A solubility and diffusivity study was made at a temperature of 60, and 75° C. over a pressure range from 0 to 20 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 17a, and 17b provide data for $C_o$, $C_s$, D, $X_{calc}$, and $X_{meas}$ at a temperature of 60° C., and 75° C., respectively.

TABLE 17a

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 59.9 | 0.0992 | — | — | — | — | 0.000 |
| 59.9 | 0.4997 | 0.03 | 0.09 | 1.23E-10 | 0.003 | 0.003 |
| 59.9 | 0.9973 | 0.13 | 0.20 | 1.28E-10 | 0.007 | 0.007 |
| 59.9 | 4.0026 | 0.76 | 0.86 | 1.21E-10 | 0.031 | 0.030 |
| 59.9 | 6.9974 | 1.30 | 1.50 | 1.58E-10 | 0.053 | 0.053 |
| 59.9 | 10.0001 | 2.02 | 2.18 | 1.12E-10 | 0.075 | 0.076 |
| 60.0 | 12.9920 | 2.71 | 2.86 | 2.55E-10 | 0.097 | 0.098 |
| 59.9 | 15.0002 | 3.20 | 3.35 | 1.68E-10 | 0.113 | 0.113 |
| 59.9 | 19.9990 | 4.39 | 4.54 | 3.12E-10 | 0.148 | 0.151 |

TABLE 17b

| T (°C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 75.0 | 0.0965 | 0.02 | 0.02 | 1.12E-10 | 0.001 | 0.001 |
| 74.9 | 0.4982 | — | — | — | — | 0.002 |
| 74.9 | 0.9998 | 0.12 | 0.16 | 1.94E-10 | 0.006 | 0.006 |
| 74.9 | 4.0035 | 0.56 | 0.65 | 2.18E-10 | 0.023 | 0.024 |

TABLE 17b-continued

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 74.9 | 6.9933 | 1.06 | 1.14 | 1.17E−10 | 0.040 | 0.040 |
| 74.9 | 10.0041 | 1.56 | 1.65 | 2.73E−10 | 0.058 | 0.057 |
| 75.0 | 12.9969 | 2.00 | 2.16 | 1.02E−10 | 0.075 | 0.074 |
| 74.9 | 15.0041 | 2.47 | 2.49 | 7.22E−10 | 0.085 | 0.083 |
| 75.0 | 19.9939 | — | — | — | — | 0.116 |

EXAMPLE 17

Solubility of difluoromethane (HFC-32) in 1-ethyl-3-methylimidazolium bis(trifluoroethylsulfonyl)imide A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 18a, 18b, 18c, and 18d provide data for $C_o$, $C_s$, D, $X_{calc}$, and $X_{meas}$ at a temperature of 10° C., 25° C., 50° C., and 75° C., respectively.

TABLE 18a

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 10.0 | 0.1015 | 0.11 | 0.19 | 6.94E−11 | 0.014 | 0.014 |
| 10.0 | 1.0012 | 1.12 | 2.06 | 8.72E−11 | 0.137 | 0.136 |
| 10.0 | 2.5030 | 4.25 | 5.55 | 1.18E−10 | 0.306 | 0.305 |
| 10.0 | 3.9929 | 8.20 | 9.58 | 1.50E−10 | 0.444 | 0.446 |
| 10.0 | 5.4925 | 13.38 | 14.83 | 1.78E−10 | 0.567 | 0.567 |
| 10.0 | 7.0043 | 19.75 | 21.63 | 2.36E−10 | 0.675 | 0.668 |
| 10.0 | 8.4935 | 27.92 | 31.92 | 1.24E−10 | 0.779 | 0.785 |

TABLE 18b

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0959 | 0.09 | 0.13 | 8.36E−11 | 0.010 | 0.010 |
| 25.0 | 0.9981 | 0.86 | 1.38 | 1.22E−10 | 0.095 | 0.095 |
| 25.0 | 2.5024 | 2.88 | 3.56 | 1.61E−10 | 0.217 | 0.217 |
| 25.0 | 3.9937 | 5.27 | 5.97 | 1.56E−10 | 0.323 | 0.323 |
| 25.0 | 5.4940 | 7.90 | 8.60 | 2.00E−10 | 0.414 | 0.414 |
| 25.0 | 6.9946 | 10.77 | 11.53 | 2.33E−10 | 0.495 | 0.495 |
| 25.0 | 8.4952 | 14.06 | 14.80 | 3.24E−10 | 0.566 | 0.565 |
| 25.0 | 9.9967 | 17.74 | 18.58 | 3.20E−10 | 0.632 | 0.637 |

TABLE 18c

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 50.0 | 0.1022 | 0.04 | 0.07 | 3.03E−10 | 0.005 | 0.005 |
| 50.0 | 1.0029 | 0.55 | 0.77 | 2.18E−10 | 0.055 | 0.055 |
| 50.0 | 2.4972 | 1.71 | 1.98 | 2.19E−10 | 0.132 | 0.132 |
| 50.0 | 4.0011 | 2.95 | 3.21 | 2.86E−10 | 0.199 | 0.199 |
| 50.0 | 5.4949 | 4.22 | 4.50 | 2.47E−10 | 0.261 | 0.262 |
| 50.0 | 7.0033 | 5.52 | 5.80 | 3.97E−10 | 0.316 | 0.316 |

TABLE 18c-continued

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 50.0 | 8.5044 | 6.93 | 7.20 | 2.90E−10 | 0.368 | 0.364 |
| 50.0 | 10.0038 | 8.22 | 8.51 | 3.43E−10 | 0.411 | 0.412 |

TABLE 18d

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 74.9 | 0.1028 | 0.01 | 0.03 | 6.36E−10 | 0.002 | 0.002 |
| 74.9 | 0.9981 | 0.36 | 0.46 | 3.41E−10 | 0.034 | 0.034 |
| 74.9 | 2.4971 | 1.09 | 1.21 | 4.21E−10 | 0.084 | 0.084 |
| 74.9 | 3.9948 | 1.82 | 1.96 | 5.11E−10 | 0.130 | 0.130 |
| 74.9 | 5.5026 | 2.60 | 2.71 | 5.24E−10 | 0.173 | 0.173 |
| 74.9 | 6.9919 | 3.37 | 3.49 | 3.22E−10 | 0.213 | 0.213 |
| 74.9 | 8.5039 | 4.16 | 4.28 | 4.63E−10 | 0.252 | 0.251 |
| 74.9 | 10.0045 | 5.10 | 5.10 | 4.75E−09 | 0.288 | 0.284 |

EXAMPLE 18

Solubility of difluoromethane (HFC-32) in 1-butyl-3-methylpyridinium bis(trifluoromethylsulfonyl)imide A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 19.

TABLE 19

| T (°C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0961 | 0.04 | 0.12 | 6.81E−11 | 0.010 | 0.010 |
| 25.0 | 0.9950 | 0.66 | 1.32 | 7.82E−11 | 0.097 | 0.100 |
| 25.0 | 2.4949 | 2.58 | 3.38 | 1.21E−10 | 0.219 | 0.223 |
| 25.0 | 3.9948 | 4.76 | 5.59 | 1.49E−10 | 0.321 | 0.329 |
| 25.0 | 5.4962 | 7.25 | 8.10 | 1.53E−10 | 0.414 | 0.424 |
| 25.0 | 7.0055 | — | — | — | — | 0.505 |
| 25.0 | 8.5057 | 13.03 | 14.47 | 1.15E−11 | 0.575 | 0.580 |
| 25.0 | 10.0002 | 17.06 | 18.28 | 2.31E−10 | 0.642 | 0.648 |

EXAMPLE 19

Solubility of difluoromethane (HFC-32) in 1-ethyl-3-methylimidazolium 1,1,2,2-tetrafluoroethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 20.

TABLE 20

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0987 | 0.01 | 0.10 | 4.12E−11 | 0.006 | 0.006 |
| 24.9 | 0.9910 | 0.40 | 1.03 | 3.25E−11 | 0.055 | 0.054 |
| 24.9 | 2.4841 | 2.48 | 2.65 | 2.94E−11 | 0.133 | 0.132 |
| 24.9 | 3.9945 | 3.66 | 4.45 | 4.93E−11 | 0.207 | 0.207 |
| 24.9 | 5.4957 | 5.78 | 6.37 | 5.92E−11 | 0.276 | 0.277 |
| 24.9 | 7.0221 | — | — | — | — | 0.344 |
| 24.9 | 8.4832 | 9.79 | 10.90 | 1.04E−10 | 0.407 | 0.407 |
| 24.9 | 10.0160 | 12.55 | 13.66 | 1.21E−10 | 0.470 | 0.471 |

EXAMPLE 20

Solubility of difluoromethane (HFC-32) in 1-butyl-3-methylimidazolium 1,1,2,2-tetrafluoroethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 21.

TABLE 21

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0967 | 0.02 | 0.12 | 2.37E−11 | 0.007 | 0.007 |
| 25.0 | 0.9986 | 0.99 | 1.29 | 1.47E−11 | 0.075 | 0.072 |
| 25.0 | 2.4997 | 2.19 | 3.31 | 2.67E−11 | 0.174 | 0.171 |
| 25.0 | 3.9716 | 4.33 | 5.40 | 3.95E−11 | 0.260 | 0.261 |
| 25.0 | 5.4838 | 6.84 | 7.78 | 4.76E−11 | 0.342 | 0.342 |
| 25.0 | 6.9946 | 8.98 | 10.39 | 7.75E−11 | 0.416 | 0.416 |
| 25.0 | 8.4811 | 11.98 | 13.27 | 8.73E−11 | 0.485 | 0.485 |
| 25.0 | 9.9886 | 15.07 | 16.62 | 1.35E−10 | 0.551 | 0.550 |

EXAMPLE 21

Solubility of difluoromethane (HFC-32) in 1-dodecyl-3-methylimidazolium 1,1,2,2-tetrafluoroethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 22.

TABLE 22

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0963 | 0.00 | 0.06 | 5.01E−11 | 0.005 | 0.006 |
| 25.0 | 0.9950 | 0.35 | 0.95 | 4.72E−11 | 0.072 | 0.074 |
| 25.0 | 2.5100 | 1.63 | 2.56 | 5.06E−11 | 0.175 | 0.178 |
| 25.0 | 3.9971 | 4.15 | 4.30 | 3.01E−11 | 0.266 | 0.271 |
| 25.0 | 5.4807 | 6.06 | 6.16 | 4.74E−11 | 0.346 | 0.353 |
| 25.0 | 7.0007 | 7.98 | 8.29 | 6.81E−11 | 0.421 | 0.429 |
| 25.0 | 8.5003 | 10.50 | 10.66 | 8.17E−11 | 0.490 | 0.497 |
| 25.0 | 10.0101 | 12.09 | 13.39 | 1.25E−10 | 0.555 | 0.562 |

EXAMPLE 22

Solubility of difluoromethane (HFC-32) in 1-heptyl-3-methylimidazolium 1,1,2,2-tetrafluoroethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 23.

TABLE 23

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0988 | 0.01 | 0.11 | 3.86E−11 | 0.008 | 0.008 |
| 25.0 | 1.0023 | 0.47 | 1.25 | 3.87E−11 | 0.081 | 0.081 |
| 25.0 | 2.5100 | 2.18 | 3.30 | 4.35E−11 | 0.192 | 0.190 |
| 25.0 | 3.9884 | 4.39 | 5.44 | 5.84E−11 | 0.286 | 0.286 |
| 25.0 | 5.4973 | 7.25 | 7.82 | 6.41E−11 | 0.371 | 0.371 |
| 25.0 | 6.9871 | 9.99 | 10.43 | 9.01E−11 | 0.448 | 0.448 |
| 25.0 | 8.4785 | 12.28 | 13.40 | 1.30E−10 | 0.518 | 0.518 |
| 25.0 | 9.9795 | 15.45 | 16.83 | 1.56E−10 | 0.585 | 0.586 |

EXAMPLE 23

Solubility of difluoromethane (HFC-32) in 1-butyl-3-methylimidazolium acetate

A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 24.

TABLE 24

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.1 | 0.0985 | 0.09 | 0.25 | 2.19E−11 | 0.010 | 0.010 |
| 25.0 | 0.9968 | 0.72 | 2.17 | 2.64E−11 | 0.078 | 0.077 |
| 25.0 | 2.4979 | 3.25 | 5.30 | 4.05E−11 | 0.176 | 0.174 |
| 25.0 | 4.0040 | 6.59 | 8.59 | 5.64E−11 | 0.264 | 0.258 |
| 25.0 | 5.4984 | 9.83 | 11.70 | 1.02E−10 | 0.335 | 0.333 |
| 25.0 | 6.9974 | 13.24 | 15.00 | 1.46E−10 | 0.402 | 0.397 |
| 24.9 | 8.5016 | 16.74 | 18.36 | 1.83E−10 | 0.462 | 0.456 |
| 25.0 | 10.0044 | 20.30 | 21.89 | 2.10E−10 | 0.516 | 0.511 |

EXAMPLE 24

Solubility of difluoromethane (HFC-32) in 1-butyl-3-methylimidazolium 2-(1,2,2,2-tetrafluoroethoxy)-1,1,2,2-tetrafluoroethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 25.

TABLE 25

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0999 | 0.02 | 0.11 | 4.30E−11 | 0.009 | 0.009 |
| 25.0 | 0.9966 | 0.82 | 1.20 | 4.29E−11 | 0.092 | 0.092 |
| 25.0 | 2.5009 | 2.29 | 3.17 | 5.44E−11 | 0.215 | 0.213 |
| 25.0 | 4.0040 | 4.16 | 5.26 | 9.11E−11 | 0.318 | 0.317 |
| 25.0 | 5.4999 | 6.53 | 7.68 | 1.04E−10 | 0.411 | 0.411 |
| 25.0 | 6.9963 | 9.19 | 10.36 | 1.49E−10 | 0.492 | 0.493 |
| 25.0 | 8.4944 | 12.24 | 13.24 | 1.26E−09 | 0.561 | 0.565 |
| 25.0 | 10.0048 | 15.74 | 17.00 | 2.78E−10 | 0.632 | 0.632 |

EXAMPLE 25

Solubility of difluoromethane (HFC-32) in 1-butyl-3-methylimidazolium 1,1,2,3,3,3-hexafluoropropanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 26.

TABLE 26

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0945 | 0.02 | 0.11 | 3.33E−11 | 0.010 | 0.010 |
| 25.0 | 0.9999 | 0.56 | 1.25 | 3.17E−11 | 0.106 | 0.104 |
| 25.0 | 2.4976 | 2.29 | 3.29 | 3.90E−11 | 0.242 | 0.241 |
| 25.0 | 3.9945 | 4.34 | 5.40 | 6.98E−11 | 0.349 | 0.347 |
| 25.0 | 5.4949 | 6.56 | 7.79 | 6.98E−11 | 0.443 | 0.443 |
| 25.0 | 6.9975 | 9.29 | 10.45 | 1.11E−10 | 0.523 | 0.523 |
| 25.0 | 8.4943 | 12.16 | 13.60 | 1.04E−10 | 0.597 | 0.599 |
| 25.0 | 10.0042 | 15.98 | 17.43 | 1.67E−10 | 0.665 | 0.664 |

EXAMPLE 26

Solubility of difluoromethane (HFC-32) in 1-butyl-3-methylimidazolium methyl sulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 27.

TABLE 27

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0993 | 0.12 | 0.24 | 2.08E−11 | 0.012 | 0.012 |
| 25.0 | 1.0010 | 0.53 | 1.48 | 2.67E−11 | 0.068 | 0.068 |
| 25.0 | 2.4982 | 2.15 | 3.65 | 3.04E−11 | 0.154 | 0.155 |
| 25.0 | 3.9954 | 4.41 | 5.87 | 4.15E−11 | 0.231 | 0.232 |
| 25.1 | 5.5009 | 6.87 | 8.16 | 5.23E−11 | 0.299 | 0.302 |
| 25.0 | 6.9953 | 9.24 | 10.77 | 6.24E−11 | 0.367 | 0.369 |
| 25.0 | 8.5005 | 11.97 | 13.33 | 9.89E−11 | 0.425 | 0.427 |
| 25.0 | 10.0059 | 14.75 | 16.32 | 1.20E−10 | 0.484 | 0.482 |

EXAMPLE 27

Solubility of difluoromethane (HFC-32) in 1-butyl-3-methylimidazolium thiocyanate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 28.

TABLE 28

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0947 | 0.02 | 0.10 | 8.08E−11 | 0.004 | 0.004 |
| 25.0 | 1.0031 | 0.45 | 1.11 | 8.57E−11 | 0.041 | 0.041 |
| 25.0 | 2.5033 | 1.90 | 2.84 | 1.03E−10 | 0.100 | 0.099 |
| 25.0 | 3.9958 | 3.66 | 4.68 | 1.11E−10 | 0.157 | 0.156 |
| 25.0 | 5.4999 | — | — | — | — | 0.212 |
| 25.0 | 6.9966 | 7.62 | 8.73 | 1.42E−10 | 0.266 | 0.267 |
| 25.0 | 8.4947 | 9.93 | 11.01 | 1.83E−10 | 0.319 | 0.320 |
| 25.0 | 9.9919 | 12.30 | 13.55 | 2.05E−10 | 0.373 | 0.373 |

EXAMPLE 28

Solubility of difluoromethane (HFC-32) in 1-butyl-3-methylimidazolium 1,1,2-trifluoro-2-(perfluoroethoxy)ethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 29.

TABLE 29

| T (° C.) | P (bar) | $C_o$ (mass %) | $C_s$ (mass %) | D (m$^2$/sec) | $X_{calc.}$ (mol. fraction) | $X_{meas.}$ (mol. fraction) |
|---|---|---|---|---|---|---|
| 25.0 | 0.0951 | 0.02 | 0.12 | 4.46E−11 | 0.010 | 0.010 |
| 25.0 | 1.0007 | 0.58 | 1.35 | 5.27E−11 | 0.103 | 0.102 |
| 25.0 | 2.4964 | 2.43 | 3.56 | 6.70E−11 | 0.236 | 0.236 |
| 25.0 | 3.9947 | 4.81 | 5.94 | 9.64E−11 | 0.346 | 0.346 |

TABLE 29-continued

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 5.4938 | 7.52 | 8.62 | 1.20E-10 | 0.442 | 0.442 |
| 25.0 | 6.9941 | 10.49 | 11.65 | 1.49E-10 | 0.525 | 0.525 |
| 25.0 | 8.4946 | 13.93 | 15.15 | 1.78E-10 | 0.600 | 0.599 |
| 25.0 | 9.9937 | 18.00 | 19.36 | 2.06E-10 | 0.668 | 0.668 |

EXAMPLE 29

Solubility of difluoromethane (HFC-32) in 1-butyl-3-methylimidazolium 1,1,2-trifluoro-2-(trifluoromethoxy)ethanesulfonate A solubility and diffusivity study was made at a temperature of 25° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided in Table 30.

TABLE 30

| T (° C.) | P (bar) | $C_o$ (mass %) | $C_s$ (mass %) | D (m²/sec) | $X_{calc.}$ (mol. fraction) | $X_{meas.}$ (mol. fraction) |
|---|---|---|---|---|---|---|
| 25.0 | 0.0947 | 0.02 | 0.13 | 4.26E-11 | 0.010 | 0.010 |
| 25.0 | 1.0031 | 0.57 | 1.42 | 4.51E-11 | 0.097 | 0.096 |
| 25.0 | 2.5033 | 2.40 | 3.71 | 5.83E-11 | 0.222 | 0.222 |
| 25.0 | 3.9958 | 4.92 | 6.28 | 7.11E-11 | 0.332 | 0.332 |
| 25.0 | 5.4999 | 7.79 | 9.04 | 9.96E-11 | 0.425 | 0.424 |
| 25.0 | 6.9966 | 10.71 | 12.12 | 1.23E-10 | 0.506 | 0.506 |
| 25.0 | 8.4947 | 14.21 | 15.63 | 1.59E-10 | 0.579 | 0.578 |
| 25.0 | 9.9919 | 18.20 | 19.62 | 2.51E-10 | 0.644 | 0.644 |

EXAMPLE 30

Solubility of 1,1,1,2-tetrafluoroethane (HFC-134a) in 1-butyl-3-methylimidazolium 1,1,2-trifluoro-2-(trifluoromethoxy)ethanesulfonate A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 18a, 18b, 18c, and 18d provide data for $C_o$, $C_s$, D, $X_{calc}$, and $X_{meas}$ at a temperature of 10° C., 25° C., 50° C., and 75° C., respectively.

TABLE 31a

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 10.0 | 0.1025 | 0.08 | 0.66 | 1.04E-11 | 0.025 | 0.026 |
| 10.0 | 0.5002 | 0.97 | 3.29 | 1.25E-11 | 0.114 | 0.117 |
| 10.0 | 1.0027 | 4.03 | 7.05 | 1.62E-11 | 0.223 | 0.225 |
| 10.0 | 1.5018 | 7.93 | 11.31 | 2.16E-11 | 0.326 | 0.326 |
| 9.9 | 2.0022 | 12.23 | 16.25 | 3.26E-11 | 0.424 | 0.424 |
| 10.0 | 2.5048 | 17.58 | 22.11 | 5.31E-11 | 0.518 | 0.514 |
| 10.0 | 2.9946 | 23.87 | 30.15 | 5.28E-11 | 0.620 | 0.628 |
| 10.0 | 3.5047 | 36.32 | 44.43 | 7.71E-11 | 0.752 | 0.745 |

TABLE 31b

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 24.9 | 0.1018 | 1.51 | 0.35 | 1.19E-11 | 0.013 | 0.017 |
| 24.9 | 0.5032 | 0.77 | 2.07 | 2.17E-11 | 0.074 | 0.075 |
| 25.1 | 1.0024 | 2.52 | 4.22 | 2.60E-11 | 0.143 | 0.143 |
| 24.8 | 1.5015 | 4.77 | 6.52 | 3.00E-11 | 0.209 | 0.208 |
| 25.0 | 2.0032 | 7.17 | 9.00 | 3.27E-11 | 0.272 | 0.271 |
| 25.0 | 2.5035 | 9.59 | 11.56 | 4.43E-11 | 0.331 | 0.331 |
| 24.9 | 3.0013 | 12.31 | 14.44 | 5.05E-11 | 0.390 | 0.389 |
| 24.8 | 3.5010 | 15.87 | 17.69 | 4.50E-11 | 0.449 | 0.450 |

TABLE 31c

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 50.0 | 0.1048 | 0.17 | 0.25 | 5.76E-11 | 0.009 | 0.009 |
| 50.0 | 0.5031 | 0.47 | 1.06 | 5.35E-11 | 0.039 | 0.039 |
| 50.0 | 1.0023 | 1.37 | 2.11 | 5.79E-11 | 0.076 | 0.076 |
| 50.0 | 1.5021 | 2.43 | 3.19 | 6.35E-11 | 0.111 | 0.111 |
| 50.0 | 2.0026 | 3.50 | 4.28 | 6.64E-11 | 0.145 | 0.145 |
| 50.0 | 2.5033 | 4.67 | 5.41 | 6.97E-11 | 0.178 | 0.179 |
| 50.0 | 3.0035 | 5.81 | 6.58 | 7.24E-11 | 0.211 | 0.211 |
| 50.0 | 3.5016 | 7.22 | 7.78 | 6.89E-11 | 0.242 | 0.243 |

TABLE 31d

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 75.0 | 0.1031 | 0.06 | 0.13 | 1.04E-10 | 0.005 | 0.005 |
| 74.9 | 0.5054 | 0.31 | 0.62 | 1.18E-10 | 0.023 | 0.023 |
| 74.9 | 1.0049 | 0.85 | 1.23 | 1.22E-10 | 0.045 | 0.045 |
| 74.9 | 1.5029 | 1.49 | 1.85 | 1.21E-10 | 0.067 | 0.067 |
| 74.9 | 2.0041 | 2.10 | 2.46 | 1.25E-10 | 0.087 | 0.087 |
| 74.9 | 2.5042 | 2.71 | 3.08 | 1.26E-10 | 0.107 | 0.108 |
| 74.9 | 3.0024 | 3.33 | 3.72 | 1.38E-10 | 0.128 | 0.128 |
| 74.9 | 3.5039 | 4.19 | 4.36 | 1.09E-10 | 0.147 | 0.147 |

EXAMPLE 31

Solubility of 1,1,1,2-tetrafluoroethane (HFC-134a) in 1-butyl-3-methylimidazolium 1,1,2-trifluoro-2-(perfluoroethoxy)ethanesulfonate A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 32a, 32b, 32c, and 32d provide data for $C_o$, $C_s$, D, $X_{calc}$, and $X_{meas}$ at a temperature of 10° C., 25° C., 50° C., and 75° C., respectively.

TABLE 32a

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 10.0 | 0.1024 | 0.06 | 0.66 | 9.33E−12 | 0.028 | 0.028 |
| 10.0 | 0.5038 | 1.01 | 3.39 | 1.15E−11 | 0.131 | 0.132 |
| 10.0 | 1.0043 | 4.05 | 7.26 | 1.71E−11 | 0.251 | 0.253 |
| 9.9  | 1.5033 | 8.17 | 11.65 | 2.53E−11 | 0.361 | 0.362 |
| 10.0 | 2.0022 | 12.78 | 16.90 | 3.67E−11 | 0.465 | 0.464 |
| 10.0 | 2.5024 | 18.33 | 23.30 | 5.37E−11 | 0.565 | 0.566 |
| 10.0 | 3.0041 | 25.90 | 32.36 | 7.06E−11 | 0.672 | 0.670 |
| 9.9  | 3.5039 | 38.42 | 47.48 | 6.49E−11 | 0.794 | 0.796 |

TABLE 32b

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 24.9 | 0.1026 | 0.11 | 0.45 | 1.80E−11 | 0.019 | 0.018 |
| 24.9 | 0.5031 | 0.72 | 2.09 | 2.32E−11 | 0.084 | 0.084 |
| 24.9 | 1.0018 | 2.62 | 4.33 | 2.59E−11 | 0.162 | 0.162 |
| 24.9 | 1.5015 | 4.92 | 6.70 | 3.23E−11 | 0.235 | 0.235 |
| 24.9 | 2.0029 | 7.33 | 9.23 | 4.14E−11 | 0.303 | 0.303 |
| 24.9 | 2.5038 | 9.92 | 11.93 | 4.99E−11 | 0.367 | 0.366 |
| 24.9 | 3.0034 | 12.73 | 14.93 | 5.74E−11 | 0.429 | 0.428 |
| 24.9 | 3.5012 | 16.44 | 18.40 | 4.94E−11 | 0.491 | 0.490 |

TABLE 32c

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 50.0 | 0.1036 | 0.20 | 0.26 | 8.37E−11 | 0.011 | 0.011 |
| 50.0 | 0.5032 | 0.47 | 1.10 | 5.99E−11 | 0.045 | 0.045 |
| 50.0 | 1.0023 | 1.52 | 2.20 | 5.66E−11 | 0.088 | 0.087 |
| 50.0 | 1.5021 | 2.55 | 3.32 | 6.59E−11 | 0.128 | 0.128 |
| 50.0 | 2.0025 | 3.69 | 4.47 | 6.87E−11 | 0.167 | 0.167 |
| 50.0 | 2.5035 | 4.90 | 5.66 | 7.37E−11 | 0.204 | 0.204 |
| 50.0 | 3.0042 | 6.08 | 6.87 | 8.56E−11 | 0.240 | 0.240 |
| 50.0 | 3.5035 | 7.49 | 8.10 | 8.02E−11 | 0.274 | 0.274 |

TABLE 32d

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 74.9 | 0.1051 | 0.11 | 0.15 | 1.09E−10 | 0.006 | 0.006 |
| 74.9 | 0.5052 | 0.34 | 0.65 | 1.19E−10 | 0.027 | 0.027 |
| 74.9 | 1.0054 | 0.92 | 1.29 | 1.22E−10 | 0.053 | 0.053 |
| 75.0 | 1.5046 | 1.90 | 1.93 | 1.93E−09 | 0.078 | 0.078 |
| 74.7 | 2.0056 | 2.25 | 2.59 | 1.05E−10 | 0.102 | 0.102 |
| 74.9 | 2.5053 | 2.88 | 3.22 | 1.50E−10 | 0.124 | 0.125 |
| 74.9 | 3.0041 | 3.56 | 3.90 | 1.30E−10 | 0.148 | 0.148 |
| 74.9 | 3.5051 | 4.34 | 4.56 | 1.42E−10 | 0.170 | 0.170 |

EXAMPLE 32

Solubility of 1,1,1,2-tetrafluoroethane (HFC-134a) in 1-ethyl-3-methylimidazolium bis(pentafluoroethylsulfonyl)imide A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 33a, 33b, 33c, and 33d provide data for $C_o$, $C_s$, D, $X_{calc}$, and $X_{meas}$ at a temperature of 10° C., 25° C., 50° C., and 75° C., respectively.

TABLE 33a

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 10.0 | 0.1031 | 0.09 | 0.61 | 1.92E−11 | 0.029 | 0.024 |
| 10.0 | 0.5039 | 1.21 | 2.51 | 4.25E−07 | 0.110 | 0.120 |
| 10.0 | 1.0027 | 4.05 | 6.65 | 2.95E−11 | 0.255 | 0.239 |
| 10.0 | 1.5024 | 7.74 | 10.72 | 3.68E−11 | 0.366 | 0.354 |
| 10.0 | 2.0011 | 12.01 | 15.61 | 4.88E−11 | 0.471 | 0.464 |
| 10.0 | 2.5009 | 17.79 | 21.74 | 6.58E−11 | 0.572 | 0.569 |
| 10.0 | 3.0043 | 24.67 | 30.25 | 8.67E−11 | 0.676 | 0.668 |
| 10.0 | 3.5049 | 37.47 | 44.30 | 6.14E−11 | 0.793 | 0.793 |

TABLE 33b

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 24.9 | 0.1054 | 0.21 | 0.42 | 2.60E−11 | 0.020 | 0.019 |
| 24.9 | 0.5052 | 0.82 | 1.92 | 3.76E−11 | 0.086 | 0.086 |
| 24.9 | 1.0046 | 2.55 | 3.90 | 4.22E−11 | 0.163 | 0.163 |
| 24.9 | 1.5040 | 4.69 | 6.02 | 4.77E−11 | 0.236 | 0.235 |
| 24.9 | 2.0037 | 6.73 | 8.29 | 5.70E−11 | 0.303 | 0.304 |
| 24.9 | 2.5031 | 9.15 | 10.79 | 6.65E−11 | 0.368 | 0.368 |
| 24.9 | 3.0043 | 11.73 | 13.53 | 7.90E−11 | 0.430 | 0.429 |
| 24.9 | 3.5054 | 15.15 | 16.56 | 7.29E−11 | 0.489 | 0.488 |

TABLE 33c

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 50.0 | 0.1046 | 0.14 | 0.23 | 5.84E−11 | 0.011 | 0.011 |
| 50.0 | 0.5050 | 0.58 | 1.00 | 6.72E−11 | 0.046 | 0.046 |
| 50.0 | 1.0043 | 1.42 | 1.99 | 8.15E−11 | 0.089 | 0.089 |
| 50.0 | 1.5046 | 2.48 | 3.00 | 7.67E−11 | 0.130 | 0.130 |
| 50.0 | 2.0037 | 3.46 | 4.04 | 8.44E−11 | 0.168 | 0.168 |
| 50.0 | 2.5033 | 4.51 | 5.10 | 8.82E−11 | 0.205 | 0.205 |
| 50.0 | 3.0034 | 5.57 | 6.19 | 9.36E−11 | 0.241 | 0.241 |
| 50.0 | 3.5040 | 6.98 | 7.32 | 8.24E−11 | 0.275 | 0.276 |

TABLE 33d

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 74.9 | 0.1044 | 0.10 | 0.13 | 1.30E−10 | 0.006 | 0.006 |
| 74.9 | 0.5057 | 0.37 | 0.58 | 1.36E−10 | 0.027 | 0.027 |
| 74.9 | 1.0042 | 0.87 | 1.16 | 1.35E−10 | 0.053 | 0.053 |
| 74.9 | 1.5043 | 1.48 | 1.73 | 1.32E−10 | 0.078 | 0.078 |
| 74.9 | 2.0041 | 2.01 | 2.30 | 1.49E−10 | 0.102 | 0.102 |
| 74.9 | 2.4957 | 2.60 | 2.88 | 1.42E−10 | 0.125 | 0.125 |
| 74.9 | 3.0049 | 3.22 | 3.47 | 1.69E−10 | 0.148 | 0.147 |
| 74.9 | 3.5027 | 3.89 | 4.06 | 1.17E−10 | 0.169 | 0.169 |

EXAMPLE 33

Solubility of 1,1,1,2-tetrafluoroethane (HFC-134a) in 1-butyl-3-methylimidazolium 1,1,2,3,3-hexafluoropropanesulfonate A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 34a, 34b, 34c, and 34d provide data for $C_o$, $C_s$, D, $X_{calc}$, and $X_{meas}$ at a temperature of 10° C., 25° C., 50° C., and 75° C., respectively.

TABLE 34a

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 10.0 | 0.0993 | 0.00 | 0.41 | 1.09E−11 | 0.015 | 0.015 |
| 9.9 | 0.5012 | 0.62 | 2.43 | 8.91E−12 | 0.083 | 0.082 |
| 10.0 | 1.0001 | 2.78 | 5.36 | 1.13E−11 | 0.170 | 0.172 |
| 10.0 | 1.4989 | 5.94 | 8.89 | 1.38E−11 | 0.261 | 0.264 |
| 9.9 | 1.9997 | 9.63 | 12.82 | 2.42E−11 | 0.348 | 0.350 |
| 10.0 | 2.4950 | 13.70 | 18.23 | 2.42E−11 | 0.447 | 0.447 |
| 10.0 | 3.0010 | 19.60 | 24.78 | 4.81E−11 | 0.545 | 0.550 |
| 10.1 | 3.4937 | 27.72 | 36.37 | 7.13E−11 | 0.675 | 0.677 |

TABLE 34b

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 24.9 | 0.1007 | −0.02 | 0.26 | 1.61E−11 | 0.009 | 0.011 |
| 24.9 | 0.5000 | 0.50 | 1.75 | 2.46E−11 | 0.061 | 0.055 |
| 24.9 | 1.0002 | 1.80 | 3.22 | 1.51E−10 | 0.108 | 0.109 |
| 24.9 | 1.4995 | 3.60 | 5.07 | 1.50E−11 | 0.162 | 0.163 |
| 24.9 | 1.9931 | 5.36 | 7.12 | 1.78E−11 | 0.218 | 0.220 |
| 25.0 | 2.5041 | 7.52 | 9.10 | 2.66E−11 | 0.267 | 0.269 |
| 24.9 | 3.0042 | 9.65 | 11.44 | 2.46E−11 | 0.319 | 0.322 |
| 24.9 | 3.5020 | 12.23 | 13.92 | 3.10E−11 | 0.370 | 0.374 |

TABLE 34c

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 50.0 | 0.1007 | 0.01 | 0.16 | 3.94E−11 | 0.006 | 0.006 |
| 50.0 | 0.5006 | 0.28 | 0.81 | 3.51E−11 | 0.029 | 0.029 |
| 50.0 | 0.9997 | 1.11 | 1.69 | 2.84E−11 | 0.059 | 0.059 |
| 50.0 | 1.4987 | 1.93 | 2.58 | 3.30E−11 | 0.088 | 0.088 |
| 50.0 | 1.9941 | 2.87 | 3.53 | 2.73E−11 | 0.117 | 0.118 |
| 50.0 | 2.5040 | 3.73 | 4.42 | 4.20E−11 | 0.144 | 0.145 |
| 50.0 | 2.9997 | 4.65 | 5.37 | 4.79E−11 | 0.171 | 0.172 |
| 50.0 | 3.5040 | 5.64 | 6.32 | 4.79E−11 | 0.197 | 0.198 |

TABLE 34d

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 74.9 | 0.0989 | 0.04 | 0.10 | 5.08E−11 | 0.003 | 0.004 |
| 74.9 | 0.5015 | 0.21 | 0.46 | 2.62E−10 | 0.016 | 0.018 |
| 74.9 | 1.0009 | 0.69 | 1.01 | 6.65E−11 | 0.036 | 0.036 |

TABLE 34d-continued

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 74.9 | 1.5002 | 1.17 | 1.51 | 7.55E−11 | 0.053 | 0.053 |
| 74.9 | 2.0006 | 1.67 | 2.03 | 6.73E−11 | 0.070 | 0.070 |
| 74.9 | 2.4996 | 2.18 | 2.53 | 8.11E−11 | 0.086 | 0.087 |
| 74.9 | 3.0020 | 2.70 | 3.06 | 8.14E−11 | 0.103 | 0.104 |

EXAMPLE 34

Solubility of 1,1,1,2-tetrafluoroethane (HFC-134a) in tetradecyl(trihexyl) phosphonium 1,1,2-trifluoro-2-(perfluoroethoxy) ethanesulfonate A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 35a, 35b, 35c, and 35d provide data for $C_o$, $C_s$, D, $X_{calc}$, and $X_{meas}$ at a temperature of 10° C., 25° C., 50° C., and 75° C., respectively.

TABLE 35a

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 10.0 | 0.0993 | 0.10 | 0.52 | 1.65E−11 | 0.038 | 0.038 |
| 9.7 | 0.5001 | 0.87 | 2.99 | 2.04E−11 | 0.190 | 0.190 |
| 9.9 | 1.0005 | 3.55 | 6.26 | 2.72E−11 | 0.338 | 0.338 |
| 9.8 | 1.4988 | 7.01 | 9.95 | 3.28E−11 | 0.458 | 0.452 |
| 10.1 | 1.9940 | 10.46 | 13.72 | 5.63E−11 | 0.549 | 0.551 |
| 9.8 | 2.4956 | 14.69 | 18.30 | 1.01E−10 | 0.631 | 0.634 |
| 9.7 | 2.9998 | 19.78 | 24.52 | 1.23E−10 | 0.713 | 0.718 |
| 9.6 | 3.4947 | 26.93 | 34.29 | 2.24E−10 | 0.800 | 0.799 |

TABLE 35b

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 24.9 | 0.1000 | −0.01 | 0.26 | 2.82E−11 | 0.019 | 0.018 |
| 24.9 | 0.5002 | 0.50 | 1.75 | 4.18E−11 | 0.120 | 0.121 |
| 25.0 | 0.9998 | 2.14 | 3.73 | 4.58E−11 | 0.229 | 0.228 |
| 24.9 | 1.4991 | 4.13 | 5.79 | 5.46E−11 | 0.320 | 0.320 |
| 24.9 | 2.0001 | 6.22 | 7.90 | 6.55E−11 | 0.396 | 0.397 |
| 24.9 | 2.5034 | 8.35 | 10.05 | 8.92E−11 | 0.461 | 0.462 |
| 24.9 | 3.0041 | 10.54 | 12.31 | 9.57E−11 | 0.518 | 0.520 |
| 24.9 | 3.5040 | 12.92 | 14.84 | 1.11E−10 | 0.571 | 0.574 |

TABLE 35c

| T (° C.) | P (bar) | $C_o$ (mass %) | $C_s$ (mass %) | $D_{eff.}$ (m²/sec) | $X_{calc.}$ (mol. fraction) | $X_{meas.}$ (mol. fraction) |
|---|---|---|---|---|---|---|
| 50.0 | 0.1013 | 0.21 | 0.09 | 1.08E−11 | 0.007 | 0.011 |
| 50.0 | 0.5011 | 0.34 | 0.94 | 9.52E−11 | 0.068 | 0.068 |
| 50.0 | 1.0012 | 1.24 | 1.97 | 9.91E−11 | 0.133 | 0.134 |
| 50.0 | 1.4996 | 2.29 | 3.01 | 1.07E−10 | 0.192 | 0.193 |
| 50.0 | 2.0006 | 3.37 | 4.07 | 9.79E−11 | 0.245 | 0.246 |
| 50.0 | 2.5005 | 4.37 | 5.10 | 1.22E−10 | 0.291 | 0.294 |

TABLE 35c-continued

| T (°C.) | P (bar) | $C_o$ (mass %) | $C_s$ (mass %) | $D_{eff}$ (m²/sec) | $X_{calc.}$ (mol. fraction) | $X_{meas.}$ (mol. fraction) |
|---|---|---|---|---|---|---|
| 50.0 | 2.9997 | 5.44 | 6.19 | 1.19E−10 | 0.335 | 0.339 |
| 50.1 | 3.4970 | 6.68 | 7.33 | 1.14E−10 | 0.377 | 0.381 |

TABLE 35d

| T (°C.) | P (bar) | $C_o$ (mass %) | $C_s$ (mass %) | $D_{eff}$ (m²/sec) | $X_{calc.}$ (mol. fraction) | $X_{meas.}$ (mol. fraction) |
|---|---|---|---|---|---|---|
| 74.9 | 0.1011 | 0.00 | 0.03 | 1.84E−10 | 0.002 | 0.003 |
| 74.9 | 0.5019 | 0.22 | 0.52 | 1.81E−10 | 0.039 | 0.039 |
| 74.9 | 1.0009 | 0.77 | 1.16 | 1.97E−10 | 0.082 | 0.083 |
| 74.9 | 1.4959 | 1.41 | 1.77 | 2.08E−10 | 0.121 | 0.122 |
| 74.9 | 2.0012 | 2.03 | 2.40 | 2.27E−10 | 0.158 | 0.160 |
| 74.9 | 2.5033 | 2.65 | 3.03 | 2.28E−10 | 0.193 | 0.194 |
| 74.9 | 3.0034 | 3.30 | 3.65 | 2.05E−10 | 0.225 | 0.227 |
| 74.9 | 3.5051 | 3.96 | 4.27 | 2.13E−10 | 0.254 | 0.256 |

EXAMPLE 35

Solubility of 1,1,1,2-tetrafluoroethane (HFC-134a) in tributyl(tetradecyl)phosphonium 1,1,2,3,3,3-hexafluoropropanesulfonate A solubility and diffusivity study was made at a temperature of 10, 25, 50, and 75° C. over a pressure range from 0 to 10 bar where the solubilities ($X_{meas.}$) were measured using a gravimetric microbalance and the diffusivities (D) were calculated using a one-dimensional diffusion model analysis. The initial concentration ($C_o$), final saturation concentration ($C_s$), and calculated solubility ($X_{calc.}$) are also provided.

Tables 36a, 36b, 36c, and 36d provide data for $C_o$, $C_s$, D, $X_{calc}$, and $X_{meas}$ at a temperature of 10° C., 25° C., 50° C., and 75° C., respectively.

TABLE 36a

| T (°C.) | P (bar) | $C_o$ (mass %) | $C_s$ (mass %) | $D_{eff}$ (m²/sec) | $X_{calc.}$ (mol. fraction) | $X_{meas.}$ (mol. Fraction) |
|---|---|---|---|---|---|---|
| 10.2 | 0.0991 | 0.08 | 0.49 | 2.23E−11 | 0.029 | 0.032 |
| 9.9 | 0.5001 | 0.72 | 2.95 | 1.30E−11 | 0.158 | 0.152 |
| 10.2 | 0.9998 | 3.17 | 6.30 | 1.74E−11 | 0.293 | 0.289 |
| 10.0 | 1.4999 | 6.59 | 9.78 | 2.67E−11 | 0.401 | 0.403 |
| 10.0 | 1.9996 | 10.48 | 13.80 | 4.77E−11 | 0.497 | 0.494 |
| 10.0 | 2.5034 | 14.41 | 18.75 | 5.41E−11 | 0.587 | 0.587 |
| 10.0 | 3.0020 | 19.66 | 24.79 | 1.49E−10 | 0.670 | 0.672 |
| 10.1 | 3.4928 | 27.70 | 34.01 | 2.02E−10 | 0.761 | 0.763 |

TABLE 36b

| T (°C.) | P (bar) | $C_o$ (mass %) | $C_s$ (mass %) | $D_{eff}$ (m²/sec) | $X_{calc.}$ (mol. fraction) | $X_{meas.}$ (mol. Fraction) |
|---|---|---|---|---|---|---|
| 25.0 | 0.0998 | 0.05 | 0.34 | 1.70E−11 | 0.021 | 0.019 |
| 24.9 | 0.5001 | 0.50 | 1.83 | 2.56E−11 | 0.103 | 0.104 |
| 24.9 | 0.9994 | 2.11 | 3.76 | 3.19E−11 | 0.194 | 0.194 |
| 25.0 | 1.4988 | 4.06 | 5.79 | 3.71E−11 | 0.275 | 0.273 |
| 24.9 | 2.0017 | 6.03 | 8.06 | 3.60E−11 | 0.351 | 0.350 |
| 25.0 | 2.5003 | 8.43 | 10.48 | 4.88E−11 | 0.419 | 0.418 |
| 25.0 | 2.9990 | 10.82 | 12.84 | 7.38E−11 | 0.476 | 0.478 |
| 25.0 | 3.5021 | 13.55 | 15.47 | 1.01E−10 | 0.530 | 0.530 |

TABLE 36c

| T (°C.) | P (bar) | $C_o$ (mass %) | $C_s$ (mass %) | $D_{eff}$ (m²/sec) | $X_{calc.}$ (mol. fraction) | $X_{meas.}$ (mol. fraction) |
|---|---|---|---|---|---|---|
| 50.0 | 0.1009 | 0.00 | 0.17 | 6.85E−11 | 0.010 | 0.010 |
| 50.0 | 0.5001 | 0.32 | 0.96 | 6.65E−11 | 0.056 | 0.056 |
| 50.0 | 0.9994 | 1.20 | 1.99 | 6.73E−11 | 0.111 | 0.110 |
| 50.0 | 1.4992 | 2.24 | 3.04 | 6.51E−11 | 0.162 | 0.161 |
| 50.0 | 2.0003 | 3.31 | 4.09 | 7.46E−11 | 0.208 | 0.209 |
| 50.0 | 2.4945 | 4.29 | 5.16 | 8.18E−11 | 0.251 | 0.254 |
| 50.0 | 2.9994 | 5.46 | 6.22 | 1.11E−10 | 0.290 | 0.293 |
| 50.0 | 3.4964 | 7.54 | 8.32 | 7.36E−11 | 0.359 | 0.333 |

TABLE 36d

| T (°C.) | P (bar) | $C_o$ (mass %) | $C_s$ (mass %) | $D_{eff}$ (m²/sec) | $X_{calc.}$ (mol. fraction) | $X_{meas.}$ (mol. fraction) |
|---|---|---|---|---|---|---|
| 75.0 | 0.1006 | 0.08 | 0.14 | 1.36E−10 | 0.009 | 0.009 |
| 74.9 | 0.5041 | 0.30 | 0.63 | 1.39E−10 | 0.037 | 0.037 |
| 74.9 | 1.0014 | 0.83 | 1.25 | 1.37E−10 | 0.072 | 0.072 |
| 74.9 | 1.5002 | 1.47 | 1.87 | 1.43E−10 | 0.105 | 0.105 |
| 74.9 | 2.0014 | 2.07 | 2.47 | 1.63E−10 | 0.135 | 0.136 |
| 74.9 | 2.5044 | 2.66 | 3.08 | 1.70E−10 | 0.164 | 0.165 |
| 74.9 | 3.0037 | 2.75 | 3.15 | 1.51E−10 | 0.167 | 0.194 |
| 74.9 | 3.5039 | 3.44 | 3.79 | 1.70E−10 | 0.196 | 0.221 |

EXAMPLE 36

The description of the microbalance components, shown in FIG. 18, are provided below.

TABLE 37

Microbalance Components Contributing to Buoyancy Calculation

| Subscript | Item | Weight (g) | Material | Density (g·cm⁻³) | Temperature (°C.) |
|---|---|---|---|---|---|
| s | Dry sample | $m_s$ | [bmim][PF$_6$] [bmim][BF$_4$] | $\rho_s$ | Sample Temp. ($T_s$) |
| a | Interacted gas | $m_a$ | $CO_2$ | $\rho_a$ | ($T_s$) |
| $i_1$ | Sample container | 0.5986 | Pyrex | 2.23 | ($T_s$) |
| $i_2$ | Wire | 0.051 | Tungsten | 21.0 | ($T_s$) |
| $i_3$ | Chain | 0.3205 | Gold | 19.3 | 30 |

TABLE 37-continued

Microbalance Components Contributing to Buoyancy Calculation

| Subscript | Item | Weight (g) | Material | Density (g · cm$^{-3}$) | Temperature (° C.) |
|---|---|---|---|---|---|
| $j_1$ | Counter-weight | 0.8054 | Stainless Steel | 7.9 | 25 |
| $j_2$ | Hook | 0.00582 | Tungsten | 21.0 | 25 |
| $j_3$ | Chain | 0.2407 | Gold | 19.3 | 30 |

Where a mixture or material is stated or described herein as comprising, including, containing, having, being composed of or being constituted by certain components or constituents, it is to be understood, unless the statement or description explicitly provides to the contrary, that one or more components or constituents in addition to those explicitly stated or described may be present in the mixture or material. In an alternative embodiment, however, the mixture or material may be stated or described as consisting essentially of certain components or constituents, in which embodiment components or constituents that would substantially alter the principle of operation or the distinguishing characteristics of the mixture or material are not present therein. In a further alternative embodiment, the mixture or material may be stated or described as consisting of certain components or constituents, in which embodiment components or constituents other than those stated or described are not present therein, with the exception of impurities.

Where the indefinite article "a" or "an" is used with respect to a statement or description of the presence of a component or constituent in a mixture or material in this invention, or the presence of a step in a process of this invention, it is to be understood, unless the statement or description explicitly provides to the contrary, that the use of such indefinite article does not limit the presence of the component or constituent in the mixture or material, or the presence of the step in the process, to one in number. The words "include", "includes" and "including" when used herein are to be read and interpreted as if they were followed by the phrase "without limitation" if in fact that is not the case.

What is claimed is:

1. A process for separating one or more components from a multi-component mixture,
   wherein the mixture comprises an azeotropic or close-boiling mixture, and
   wherein the mixture comprises a first hydrofluorocarbon compound and one or more members of the group consisting of:
      a) a second hydrofluorocarbon compound; and
      b) a fluorocarbon compound selected from the group consisting of a compound that consists solely of fluorine and carbon atoms (an "FC-fluorocarbon compound"), a fluoroether compound, a fluoroketone compound, a fluoroaromatic compound, and a fluoroolefin compound;
   wherein the process comprises contacting the mixture with at least one ionic liquid in which one component of the mixture is less soluble than at least one other component of the mixture, and separating the less soluble component from the mixture;
   wherein the at least one ionic liquid comprises both a fluorinated cation and a fluorinated anion; and
   wherein the separation process comprises steps from a process selected from the group consisting of distillation, stripping, rectification, extraction, chromatography and evaporation.

2. The process of claim 1 wherein the first or second hydrofluorocarbon compound is selected from the group consisting of a compound that consists solely of fluorine, carbon and hydrogen atoms (an "HFC-hydrofluorocarbon compound"), a hydrofluoroether compound, a hydrofluoroketone compound, a hydrofluoroaromatic compound, and a hydrofluoroolefin compound.

3. The process of claim 1 wherein the first or second hydrofluorocarbon compound is selected from the group consisting of trifluoromethane (HFC-23), difluoromethane (HFC-32), pentafluoroethane (HFC-125), 1,1,2,2-tetrafluoroethane (HFC-134), 1,1,1,2-tetrafluoroethane (HFC-134a), 1,1,1-trifluoroethane (HFC-143a), 1,1-difluoroethane (HFC-152a), fluoroethane (HFC-161), methyl nonafluoroisobutyl ether, methyl nonafluorobutyl ether, ethyl nonafluoroisobutyl ether, ethyl nonafluorobutyl ether, and 3-ethoxy-1,1,1,2,3,4,4,5,5,6,6,6-dodecafluoro-2-trifluoromethylhexane.

4. The process of claim 1 wherein a fluorocarbon compound is an FC-fluorocarbon compound.

5. The process of claim 1 wherein an FC-fluorocarbon compound, when contained in a multi-component mixture, is selected from the group consisting of perfluoromethane (FC-14), perfluoroethane (FC-116), and perfluoropropane (FC-218).

6. The process of claim 1 wherein the mixture comprises a pair of refrigerants selected from the group of pairs consisting of:
   (i) HFC-32 and HFC-125,
   (ii) HFC-125 and HFC-143a,
   (iii) HFC-32 and HFC-143a,
   (iv) CFC-115 and HFC-125,
   (v) HFC-32 and HFC-134a, and
   (iv) CFC-125 and HFC-134a.

7. The process of any one of claims 1 to 6 wherein a fluorinated cation is selected from the group consisting of the following eleven cations:

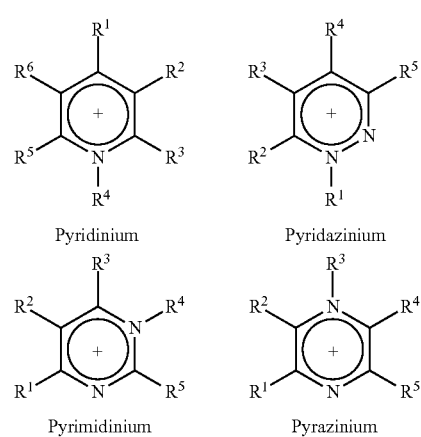

Pyridinium

Pyridazinium

Pyrimidinium

Pyrazinium

-continued

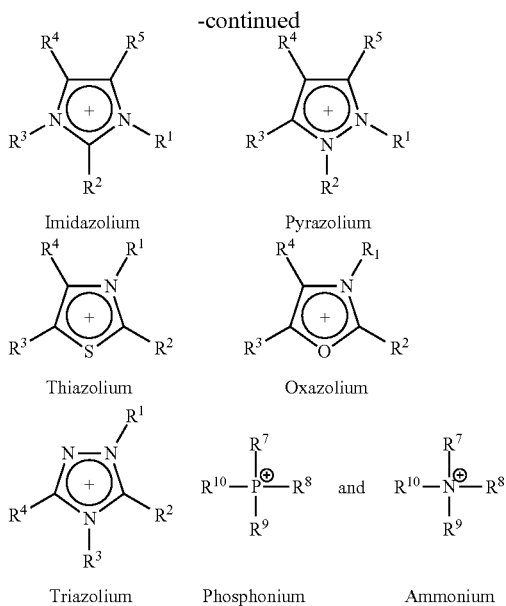

Imidazolium    Pyrazolium

Thiazolium    Oxazolium

Triazolium    Phosphonium    Ammonium wherein $R^1$, $R^2$, $R^3$, $R^4$, $R^5$ and $R^6$ are each independently selected from the group consisting of:
(i) H;
(ii) halogen;
(iii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(iv) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
(v) a $C_6$ to $C_{20}$ unsubstituted aryl, or $C_6$ to $C_{25}$ unsubstituted heteroaryl, group having one to three heteroatoms independently selected from the group consisting of O, N, Si and S; and
(vi) a $C_6$ to $C_{25}$ substituted aryl, or a $C_6$ to $C_{25}$ substituted heteroaryl, group having one to three heteroatoms independently selected from the group consisting of O, N, Si and S;
wherein said substituted aryl or substituted heteroaryl group has one to three substituents independently selected from the group consisting of:
(1) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, NH2 and SH,
(2) OH,
(3) $NH_2$, and
(4) SH; and
wherein $R^7$, $R^8$, $R^9$, and $R^{10}$ are each independently selected from the group consisting of:
(i) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(ii) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
(iii) a $C_6$ to $C_{25}$ unsubstituted aryl, or a $C_6$ to $C_{25}$ unsubstituted heteroaryl, group having one to three heteroatoms independently selected from the group consisting of O, N, Si and S; and
(iv) a $C_6$ to $C_{25}$ substituted aryl, or a $C_6$ to $C_{25}$ substituted heteroaryl, group having one to three heteroatoms independently selected from the group consisting of O, N, Si and S;
wherein said substituted aryl or substituted heteroaryl group has one to three substituents independently selected from the group consisting of:
(1) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH,
(2) OH,
(3) $NH_2$, and
(4) SH; and
wherein optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group; and;
wherein at least one of $R^1$, $R^2$, $R^3$, $R^4$, $R^5$, $R^6$, $R^7$, $R^8$, $R^9$, and $R^{10}$ comprises a fluorine-substituted group, or F—.

8. The process of claim 7 wherein a fluorinated anion, as contained in the at least one ionic liquid, is selected from the group consisting of $[BF_4]$—, $[PF_6]$—, $[SbF_6]$—, $[CF_3SO_3]$—, $[HCF_2CF_2SO_3]$—, $[CF_3HFCCF_2SO_3]$—, $[HCClFCF_2SO_3]$—, $[(CF_3SO_2)_2N]$—, $[(CF_3CF_2SO_2)_2N]$—, $[(CF_3SO_2)_3C]$—, $[CF_3CO_2]$—, $[CF_3OCFHCF_2SO_3]$—, $[CF_3CF_2OCFHCF_2SO_3]$—, $[CF_3CFHOCF_2CF_2SO_3]$—, $[CF_2HCF_2OCF_2CF_2SO_3]$—, $[CF_2ICF_2OCF_2CF_2SO_3]$—, $[CF_3CF_2OCF_2CF_2SO_3]$—, $[(CF_2HCF_2SO_2)_2N]$—, $[(CF_3CFHCF_2SO_2)_2N]$—, and F—.

9. The process of claim 1 wherein a fluorinated anion, as contained in the at least one ionic liquid, is selected from the group consisting of $[BF_4]$—, $[PF_6]$—, $[SbF_6]$—, $[CF_3SO_3]$—, $[HCF_2CF_2SO_3]$—, $[CF_3HFCCF_2SO_3]$—, $[HCClFCF_2SO_3]$—, $[(CF_3SO_2)_2N]$—, $[(CF_3CF_2SO_2)_2N]$—, $[(CF_3SO_2)_3C]$—, $[CF_3CO_2]$—, $[CF_3OCFHCF_2SO_3]$—, $[CF_3CF_2OCFHCF_2SO_3]$—, $[CF_3CFHOCF_2CF_2SO_3]$—, $[CF_2HCF_2OCF_2CF_2SO_3]$—, $[CF_2ICF_2OCF_2CF_2SO_3]$—, $[CF_3CF_2OCF_2CF_2SO_3]$—, $[(CF_2HCF_2SO_2)_2N]$—, $[(CF_3CFHCF_2SO_2)_2N]$—, and F—.

10. The process of claim 1 wherein the mixture comprises both the first and second hydrofluorocarbons.

11. The process of claim 1 wherein the mixture comprises HFC-32 and HFC-125, and HFC-125 is the less soluble component that is separated from the mixture.

12. The process of claim 1 wherein the distillation is performed in a distillation column.

13. The process of claim 12 wherein the less soluble component is removed from the top of the column.

14. The process of claim 12 wherein the at least one ionic liquid and the more soluble component are removed together from the bottom of the column, the at least one ionic liquid and the more soluble component are separated outside the column, and the at least one ionic liquid is returned to the column.

15. The process of claim 12 wherein the mixture comprises a pair of refrigerants selected from the group of pairs consisting of:
(i) HFC-32 and HFC-125,
(ii) HFC-125 and HFC-143a, (iii) HFC-32 and HFC-143a,
(iv) CFC-115 and HFC-125,
(v) HFC-32 and HFC-134a, and
(iv) CFC-125 and HFC-134a.

* * * * *